(12) United States Patent
Moubarak

(10) Patent No.: US 11,974,829 B2
(45) Date of Patent: May 7, 2024

(54) LINK-DRIVEN ARTICULATION DEVICE FOR A SURGICAL DEVICE

(71) Applicant: Cilag GmbH International, Zug (CH)

(72) Inventor: Paul Moubarak, West Chester, OH (US)

(73) Assignee: Cilag GmbH International, Zug (CH)

( * ) Notice: Subject to any disclaimer, the term of this patent is extended or adjusted under 35 U.S.C. 154(b) by 330 days.

(21) Appl. No.: 17/363,573

(22) Filed: Jun. 30, 2021

(65) Prior Publication Data

US 2023/0000578 A1 Jan. 5, 2023

(51) Int. Cl.
*A61B 17/064* (2006.01)
*A61B 34/00* (2016.01)
*A61B 34/35* (2016.01)
*A61B 34/30* (2016.01)

(52) U.S. Cl.
CPC .............. *A61B 34/71* (2016.02); *A61B 34/35* (2016.02); *A61B 2034/301* (2016.02); *A61B 2034/305* (2016.02)

(58) Field of Classification Search
CPC ............ A61B 34/71; A61B 2017/2927; A61B 2017/00367
See application file for complete search history.

(56) References Cited

U.S. PATENT DOCUMENTS

| | | |
|---|---|---|
| 2,366,274 A | 1/1945 | Luth et al. |
| 2,458,152 A | 1/1949 | Eakins |
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |

(Continued)

FOREIGN PATENT DOCUMENTS

| | | |
|---|---|---|
| CN | 201223445 Y | 4/2009 |
| CN | 102274074 A | 12/2011 |

(Continued)

OTHER PUBLICATIONS

"ATM-MPLS Network Interworking Version 2.0, af-aic-0178.001" ATM Standard, The ATM Forum Technical Committee, published Aug. 2003.

(Continued)

*Primary Examiner* — Eyamindae C Jallow

(57) ABSTRACT

Disclosed is a robotic surgical tool, comprising an end effector, an elongate shaft, and an articulation joint. The articulation joint comprises a pivot plate attached to the end effector, a fixed plate attached to the elongate shaft, and a spherical joint coupled to the pivot plate and the fixed plate. The robotic surgical tool further comprises an articulation drive system. The articulation drive system comprises a first rod, a second rod, a third rod, and a fourth rod that extend through the elongate shaft, a first mechanical link pivotably coupled to the first rod and to the pivot plate, a second mechanical link pivotably coupled to the second rod and to the pivot plate, a third mechanical link pivotably coupled to the third rod and to the pivot plate, and a fourth mechanical link pivotably coupled to the fourth rod and to the pivot plate.

20 Claims, 20 Drawing Sheets

(56) References Cited

U.S. PATENT DOCUMENTS

| | | |
|---|---|---|
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,633,874 A | 1/1987 | Chow et al. |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 4,936,842 A | 6/1990 | D'Amelio et al. |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,004 A | 11/1993 | Bales et al. |
| 5,258,006 A | 11/1993 | Rydell et al. |
| 5,285,945 A | 2/1994 | Brinkerhoff et al. |
| 5,290,286 A | 3/1994 | Parins |
| 5,293,863 A | 3/1994 | Zhu et al. |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,860 A | 1/1995 | Lau |
| 5,383,874 A | 1/1995 | Jackson et al. |
| 5,383,880 A | 1/1995 | Hooven |
| 5,383,888 A | 1/1995 | Zvenyatsky et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,524,643 A | 6/1996 | Faries, Jr. et al. |
| 5,529,235 A | 6/1996 | Boiarski et al. |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,615 A | 9/1997 | Blake, III |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,325 A | 3/1999 | Mizuno et al. |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,980,493 A | 11/1999 | Smith et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| 6,113,598 A | 9/2000 | Baker |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |

(56) References Cited

U.S. PATENT DOCUMENTS

| | | |
|---|---|---|
| 6,174,309 B1 | 1/2001 | Wrublewski et al. |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,241,724 B1 | 6/2001 | Fleischman et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,094 B1 | 5/2002 | Eitenmuller |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,458,130 B1 | 10/2002 | Frazier et al. |
| 6,461,363 B1 | 10/2002 | Gadberry et al. |
| 6,464,702 B2 | 10/2002 | Schulze et al. |
| 6,475,211 B2 | 11/2002 | Chess et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,290 B2 | 3/2003 | Adams et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,709,445 B2 | 3/2004 | Boebel et al. |
| 6,719,765 B2 | 4/2004 | Bonutti |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrodinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B2 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,134,587 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,208,005 B2 | 4/2007 | Frecker et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,451,904 B2 | 11/2008 | Shelton, IV |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,491,202 B2 | 2/2009 | Odom et al. |
| 7,494,501 B2 | 2/2009 | Ahlberg et al. |

(56) References Cited

U.S. PATENT DOCUMENTS

| | | |
|---|---|---|
| 7,498,080 B2 | 3/2009 | Tung et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,608,083 B2 | 10/2009 | Lee et al. |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,691,098 B2 | 4/2010 | Wallace et al. |
| 7,703,459 B2 | 4/2010 | Saadat et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,722,527 B2 | 5/2010 | Bouchier et al. |
| 7,722,607 B2 | 5/2010 | Dumbauld et al. |
| 7,727,244 B2 | 6/2010 | Orban, III et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter et al. |
| 7,841,980 B2 | 11/2010 | Minosawa et al. |
| 7,846,159 B2 | 12/2010 | Morrison et al. |
| 7,846,160 B2 | 12/2010 | Payne et al. |
| 7,850,688 B2 | 12/2010 | Hafner |
| 7,867,228 B2 | 1/2011 | Nobis et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,919,184 B2 | 4/2011 | Mohapatra et al. |
| 7,931,649 B2 | 4/2011 | Couture et al. |
| 7,935,114 B2 | 5/2011 | Takashino et al. |
| 7,935,130 B2 | 5/2011 | Williams |
| 7,955,322 B2 | 6/2011 | Devengenzo et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,980,443 B2 | 7/2011 | Scheib et al. |
| 7,981,113 B2 | 7/2011 | Truckai et al. |
| 7,982,776 B2 | 7/2011 | Dunki-Jacobs et al. |
| 7,995,045 B2 | 8/2011 | Dunki-Jacobs |
| 7,997,278 B2 | 8/2011 | Utley et al. |
| 8,016,855 B2 | 9/2011 | Whitman et al. |
| 8,020,743 B2 | 9/2011 | Shelton, IV |
| 8,048,070 B2 | 11/2011 | O'Brien et al. |
| 8,054,184 B2 | 11/2011 | Cline et al. |
| 8,058,771 B2 | 11/2011 | Giordano et al. |
| 8,066,167 B2 | 11/2011 | Measamer et al. |
| 8,070,036 B1 | 12/2011 | Knodel |
| 8,070,731 B2 | 12/2011 | Wenchell et al. |
| 8,075,555 B2 | 12/2011 | Truckai et al. |
| 8,075,558 B2 | 12/2011 | Truckai et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,128,624 B2 | 3/2012 | Couture et al. |
| 8,136,712 B2 | 3/2012 | Zingman |
| 8,141,762 B2 | 3/2012 | Bedi et al. |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,186,560 B2 | 5/2012 | Hess et al. |
| 8,187,267 B2 | 5/2012 | Pappone et al. |
| 8,197,446 B2 | 6/2012 | Beardsley |
| 8,197,472 B2 | 6/2012 | Lau et al. |
| 8,197,479 B2 | 6/2012 | Olson et al. |
| 8,210,411 B2 | 7/2012 | Yates et al. |
| 8,221,415 B2 | 7/2012 | Francischelli |
| 8,241,235 B2 | 8/2012 | Kahler et al. |
| 8,241,283 B2 | 8/2012 | Guerra et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,232 B2 | 10/2012 | Unger |
| 8,303,583 B2 | 11/2012 | Hosier et al. |
| 8,308,040 B2 | 11/2012 | Huang et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,343,146 B2 | 1/2013 | Godara et al. |
| 8,343,171 B2 | 1/2013 | Farritor et al. |
| 8,348,126 B2 | 1/2013 | Olson et al. |
| 8,357,144 B2 | 1/2013 | Whitman et al. |
| 8,357,158 B2 | 1/2013 | McKenna et al. |
| 8,377,059 B2 | 2/2013 | Deville et al. |
| 8,388,646 B2 | 3/2013 | Chojin |
| 8,397,971 B2 | 3/2013 | Yates et al. |
| 8,403,926 B2 | 3/2013 | Nobis et al. |
| 8,414,577 B2 | 4/2013 | Boudreaux et al. |
| 8,423,182 B2 | 4/2013 | Robinson et al. |
| 8,425,410 B2 | 4/2013 | Murray et al. |
| 8,430,811 B2 | 4/2013 | Hess et al. |
| 8,430,876 B2 | 4/2013 | Kappus et al. |
| 8,453,906 B2 | 6/2013 | Huang et al. |
| 8,454,599 B2 | 6/2013 | Inagaki et al. |
| 8,460,288 B2 | 6/2013 | Tamai et al. |
| 8,460,292 B2 | 6/2013 | Truckai et al. |
| 8,484,833 B2 | 7/2013 | Cunningham et al. |
| 8,485,970 B2 | 7/2013 | Widenhouse et al. |
| 8,486,057 B2 | 7/2013 | Behnke |
| 8,491,533 B2 | 7/2013 | Parihar et al. |
| 8,491,625 B2 | 7/2013 | Horner |
| 8,496,682 B2 | 7/2013 | Guerra et al. |
| 8,512,364 B2 | 8/2013 | Kowalski et al. |
| 8,529,437 B2 | 9/2013 | Taylor et al. |

(56) References Cited

U.S. PATENT DOCUMENTS

| | | |
|---|---|---|
| 8,535,311 B2 | 9/2013 | Schall |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,579,176 B2 | 11/2013 | Smith et al. |
| 8,579,937 B2 | 11/2013 | Gresham |
| 8,591,459 B2 | 11/2013 | Clymer et al. |
| 8,591,506 B2 | 11/2013 | Wham et al. |
| 8,613,383 B2 | 12/2013 | Beckman et al. |
| 8,613,727 B2 | 12/2013 | Hart et al. |
| 8,616,431 B2 | 12/2013 | Timm et al. |
| 8,622,274 B2 | 1/2014 | Yates et al. |
| 8,623,016 B2 | 1/2014 | Fischer |
| 8,623,044 B2 | 1/2014 | Timm et al. |
| 8,628,529 B2 | 1/2014 | Aldridge et al. |
| 8,632,461 B2 | 1/2014 | Glossop |
| 8,636,736 B2 | 1/2014 | Yates et al. |
| 8,640,788 B2 | 2/2014 | Dachs, II et al. |
| 8,647,350 B2 | 2/2014 | Mohan et al. |
| 8,652,120 B2 | 2/2014 | Giordano et al. |
| 8,663,222 B2 | 3/2014 | Anderson et al. |
| 8,668,691 B2 | 3/2014 | Heard |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,801,752 B2 | 8/2014 | Fortier et al. |
| 8,814,856 B2 | 8/2014 | Elmouelhi et al. |
| 8,827,995 B2 | 9/2014 | Schaller et al. |
| 8,828,023 B2 | 9/2014 | Neff et al. |
| 8,834,466 B2 | 9/2014 | Cummings et al. |
| 8,834,518 B2 | 9/2014 | Faller et al. |
| 8,851,354 B2 | 10/2014 | Swensgard et al. |
| 8,864,757 B2 | 10/2014 | Klimovitch et al. |
| 8,864,761 B2 | 10/2014 | Johnson et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,912,746 B2 | 12/2014 | Reid et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,961,515 B2 | 2/2015 | Twomey et al. |
| 8,979,843 B2 | 3/2015 | Timm et al. |
| 8,979,844 B2 | 3/2015 | White et al. |
| 8,986,302 B2 | 3/2015 | Aldridge et al. |
| 8,992,422 B2 | 3/2015 | Spivey et al. |
| 8,992,526 B2 | 3/2015 | Brodbeck et al. |
| 9,002,518 B2 | 4/2015 | Manzo et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,333 B2 | 4/2015 | Beale et al. |
| 9,028,494 B2 | 5/2015 | Shelton, IV et al. |
| 9,028,519 B2 | 5/2015 | Yates et al. |
| 9,039,695 B2 | 5/2015 | Giordano et al. |
| 9,039,705 B2 | 5/2015 | Takashino |
| 9,044,243 B2 | 6/2015 | Johnson et al. |
| 9,044,245 B2 | 6/2015 | Condie et al. |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,072,536 B2 | 7/2015 | Shelton, IV et al. |
| 9,089,360 B2 | 7/2015 | Messerly et al. |
| 9,095,362 B2 | 8/2015 | Dachs et al. |
| 9,101,385 B2 | 8/2015 | Shelton, IV et al. |
| 9,106,270 B2 | 8/2015 | Puterbaugh et al. |
| 9,107,684 B2 | 8/2015 | Ma |
| 9,113,900 B2 | 8/2015 | Buysse et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,149,324 B2 | 10/2015 | Huang et al. |
| 9,161,803 B2 | 10/2015 | Yates et al. |
| 9,168,054 B2 | 10/2015 | Turner et al. |
| 9,168,089 B2 | 10/2015 | Buysse et al. |
| 9,179,912 B2 | 11/2015 | Yates et al. |
| 9,192,431 B2 | 11/2015 | Woodruff et al. |
| 9,198,715 B2 | 12/2015 | Livneh |
| 9,204,879 B2 | 12/2015 | Shelton, IV |
| 9,220,559 B2 | 12/2015 | Worrell et al. |
| 9,226,751 B2 | 1/2016 | Shelton, IV et al. |
| 9,237,891 B2 | 1/2016 | Shelton, IV |
| 9,254,165 B2 | 2/2016 | Aronow et al. |
| 9,259,265 B2 | 2/2016 | Harris et al. |
| 9,259,277 B2 | 2/2016 | Rogers et al. |
| 9,265,567 B2 | 2/2016 | Orban, III et al. |
| 9,265,926 B2 | 2/2016 | Strobl et al. |
| 9,282,974 B2 | 3/2016 | Shelton, IV |
| 9,283,027 B2 | 3/2016 | Monson et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,320,563 B2 | 4/2016 | Brustad et al. |
| 9,333,025 B2 | 5/2016 | Monson et al. |
| 9,339,323 B2 | 5/2016 | Eder et al. |
| 9,339,342 B2 | 5/2016 | Prisco et al. |
| 9,345,481 B2 | 5/2016 | Hall et al. |
| 9,364,230 B2 | 6/2016 | Shelton, IV et al. |
| 9,375,232 B2 | 6/2016 | Hunt et al. |
| 9,386,983 B2 | 7/2016 | Swensgard et al. |
| 9,402,682 B2 | 8/2016 | Worrell et al. |
| 9,408,606 B2 | 8/2016 | Shelton, IV |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,864 B2 | 10/2016 | Witt et al. |
| 9,492,224 B2 | 11/2016 | Boudreaux et al. |
| 9,504,524 B2 | 11/2016 | Behnke, II |
| 9,526,407 B2 | 12/2016 | Hoeg et al. |
| 9,526,565 B2 | 12/2016 | Strobl |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,572,552 B1 | 2/2017 | Bodor et al. |
| 9,597,104 B2 | 3/2017 | Nicholas et al. |
| 9,597,143 B2 | 3/2017 | Madan et al. |
| 9,610,091 B2 | 4/2017 | Johnson et al. |
| 9,642,669 B2 | 5/2017 | Takashino et al. |
| 9,649,110 B2 | 5/2017 | Parihar et al. |
| 9,649,111 B2 | 5/2017 | Shelton, IV et al. |

(56) References Cited

U.S. PATENT DOCUMENTS

| | | |
|---|---|---|
| 9,668,806 B2 | 6/2017 | Unger et al. |
| 9,707,027 B2 | 7/2017 | Ruddenklau et al. |
| 9,737,355 B2 | 8/2017 | Yates et al. |
| 9,737,358 B2 | 8/2017 | Beckman et al. |
| 9,757,128 B2 | 9/2017 | Baber et al. |
| 9,757,186 B2 | 9/2017 | Boudreaux et al. |
| 9,763,661 B2 | 9/2017 | Zergiebel et al. |
| 9,782,214 B2 | 10/2017 | Houser et al. |
| 9,795,436 B2 | 10/2017 | Yates et al. |
| 9,808,308 B2 | 11/2017 | Faller et al. |
| 9,814,514 B2 | 11/2017 | Shelton, IV et al. |
| 9,820,740 B2 | 11/2017 | Zemlok et al. |
| 9,820,771 B2 | 11/2017 | Norton et al. |
| 9,861,428 B2 | 1/2018 | Trees et al. |
| 9,877,776 B2 | 1/2018 | Boudreaux |
| 9,888,942 B1 | 2/2018 | Savage et al. |
| 9,913,680 B2 | 3/2018 | Voegele et al. |
| 9,913,694 B2 | 3/2018 | Brisson |
| 9,937,626 B2 | 4/2018 | Rockrohr |
| 9,987,008 B2 | 6/2018 | Scirica et al. |
| 10,016,207 B2 | 7/2018 | Suzuki et al. |
| 10,070,916 B2 | 9/2018 | Artale |
| 10,092,310 B2 | 10/2018 | Boudreaux et al. |
| 10,098,527 B2 | 10/2018 | Weisenburgh, II et al. |
| 10,164,466 B2 | 12/2018 | Calderoni |
| 10,166,060 B2 | 1/2019 | Johnson et al. |
| 10,166,080 B2 | 1/2019 | Balicki et al. |
| 10,166,082 B1 | 1/2019 | Hariri et al. |
| 10,172,669 B2 | 1/2019 | Felder et al. |
| 10,172,687 B2 | 1/2019 | Garbus et al. |
| 10,179,413 B2 | 1/2019 | Rockrohr |
| 10,194,976 B2 | 2/2019 | Boudreaux |
| 10,213,266 B2 | 2/2019 | Zemlok et al. |
| 10,231,775 B2 | 3/2019 | Shelton, IV et al. |
| 10,251,672 B2 | 4/2019 | Meglan |
| 10,258,359 B2 | 4/2019 | Kapadia |
| 10,265,118 B2 | 4/2019 | Gerhardt |
| 10,278,721 B2 | 5/2019 | Dietz et al. |
| 10,321,964 B2 | 6/2019 | Grover et al. |
| 10,368,838 B2 | 8/2019 | Williams et al. |
| 10,376,338 B2 | 8/2019 | Taylor et al. |
| 10,390,895 B2 | 8/2019 | Henderson et al. |
| 10,398,517 B2 | 9/2019 | Eckert et al. |
| 10,420,620 B2 | 9/2019 | Rockrohr |
| 10,426,516 B2 | 10/2019 | Racenet et al. |
| 10,463,421 B2 | 11/2019 | Boudreaux et al. |
| 10,470,830 B2 | 11/2019 | Hill et al. |
| 10,507,068 B2 | 12/2019 | Kopp et al. |
| 10,517,686 B2 | 12/2019 | Vokrot et al. |
| 10,537,351 B2 | 1/2020 | Shelton, IV et al. |
| 10,548,504 B2 | 2/2020 | Shelton, IV et al. |
| 10,561,470 B2 | 2/2020 | Hourtash et al. |
| 10,588,706 B2 | 3/2020 | Limon |
| 10,624,691 B2 | 4/2020 | Wiener et al. |
| 10,639,111 B2 | 5/2020 | Kopp |
| 10,653,489 B2 | 5/2020 | Kopp |
| 10,667,877 B2 | 6/2020 | Kapadia |
| 10,675,104 B2 | 6/2020 | Kapadia |
| 10,716,639 B2 | 7/2020 | Kapadia et al. |
| 10,736,219 B2 | 8/2020 | Seow et al. |
| 10,743,872 B2 | 8/2020 | Leimbach et al. |
| 10,751,087 B2 | 8/2020 | Morgan et al. |
| 10,765,484 B2 | 9/2020 | Bonutti et al. |
| 10,772,688 B2 | 9/2020 | Peine et al. |
| 10,779,849 B2 | 9/2020 | Shelton, IV et al. |
| 10,779,897 B2 | 9/2020 | Rockrohr |
| 10,779,900 B2 | 9/2020 | Pedros et al. |
| 10,799,304 B2 | 10/2020 | Kapadia et al. |
| 10,806,454 B2 | 10/2020 | Kopp |
| 10,813,703 B2 | 10/2020 | Swayze et al. |
| 10,849,700 B2 | 12/2020 | Kopp et al. |
| 10,881,399 B2 | 1/2021 | Shelton, IV et al. |
| 10,893,884 B2 | 1/2021 | Stoddard et al. |
| 10,898,280 B2 | 1/2021 | Kopp |
| 10,912,616 B2 | 2/2021 | Dachs et al. |
| 10,932,772 B2 | 3/2021 | Shelton, IV et al. |
| 10,959,788 B2 | 3/2021 | Grover et al. |
| 10,980,610 B2 | 4/2021 | Rosenberg et al. |
| 11,013,563 B2 | 5/2021 | Shelton, IV et al. |
| 11,013,569 B2 | 5/2021 | Shelton, IV et al. |
| 11,026,764 B2 | 6/2021 | Kopp |
| 11,045,265 B2 | 6/2021 | Seow et al. |
| 11,058,504 B2 | 7/2021 | Blanco et al. |
| 11,090,125 B2 | 8/2021 | Peine et al. |
| 11,109,866 B2 | 9/2021 | Shelton, IV et al. |
| 11,160,623 B2 | 11/2021 | Hagn |
| 11,207,146 B2 | 12/2021 | Shelton, IV et al. |
| 11,229,471 B2 | 1/2022 | Shelton, IV et al. |
| 11,278,362 B2 | 3/2022 | Shelton, IV et al. |
| 11,298,128 B2 | 4/2022 | Messerly et al. |
| 11,304,699 B2 | 4/2022 | Shelton, IV et al. |
| 11,364,067 B2 | 6/2022 | Murrell et al. |
| 11,369,443 B2 | 6/2022 | Shelton, IV et al. |
| 11,376,082 B2 | 7/2022 | Shelton, IV et al. |
| 11,376,083 B2 | 7/2022 | Harris et al. |
| 11,389,164 B2 | 7/2022 | Yates et al. |
| 11,399,906 B2 | 8/2022 | Shelton, IV et al. |
| 11,413,102 B2 | 8/2022 | Shelton, IV et al. |
| 11,432,885 B2 | 9/2022 | Shelton, IV et al. |
| 11,510,747 B2 | 11/2022 | Zemlok et al. |
| 11,523,859 B2 | 12/2022 | Shelton, IV et al. |
| 11,547,465 B2 | 1/2023 | Shelton, IV et al. |
| 11,547,468 B2 | 1/2023 | Shelton, IV et al. |
| 11,559,307 B2 | 1/2023 | Shelton, IV et al. |
| 11,559,308 B2 | 1/2023 | Yates et al. |
| 11,576,677 B2 | 2/2023 | Shelton, IV et al. |
| 11,589,888 B2 | 2/2023 | Shelton, IV et al. |
| 11,607,239 B2 | 3/2023 | Swensgard et al. |
| 11,607,278 B2 | 3/2023 | Shelton, IV et al. |
| 11,612,445 B2 | 3/2023 | Shelton, IV et al. |
| 11,659,023 B2 | 5/2023 | Shelton, IV et al. |
| 11,723,729 B2 | 8/2023 | Shelton, IV et al. |
| 11,813,746 B2 | 11/2023 | Overmyer et al. |
| 11,839,420 B2 | 12/2023 | Shelton, IV et al. |
| 2002/0022836 A1 | 2/2002 | Goble et al. |
| 2002/0072736 A1 | 6/2002 | Tierney et al. |
| 2003/0014053 A1 | 1/2003 | Nguyen et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0229344 A1 | 12/2003 | Dycus et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0249374 A1 | 12/2004 | Tetzlaff et al. |
| 2004/0260273 A1 | 12/2004 | Wan |
| 2005/0006432 A1 | 1/2005 | Racenet et al. |
| 2005/0015125 A1 | 1/2005 | Mioduski et al. |
| 2005/0033278 A1 | 2/2005 | McClurken et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0267464 A1 | 12/2005 | Truckai et al. |
| 2006/0064086 A1 | 3/2006 | Odom |
| 2006/0069306 A1 | 3/2006 | Banik et al. |
| 2006/0135978 A1 | 6/2006 | Franer |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0032704 A1 | 2/2007 | Gandini et al. |
| 2007/0073185 A1 | 3/2007 | Nakao |
| 2007/0073341 A1 | 3/2007 | Smith et al. |
| 2007/0078395 A1 | 4/2007 | Valaie |
| 2007/0135826 A1 | 6/2007 | Zaver et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0232926 A1 | 10/2007 | Stulen et al. |
| 2007/0232928 A1 | 10/2007 | Wiener et al. |

(56) References Cited

U.S. PATENT DOCUMENTS

| | | |
|---|---|---|
| 2007/0236213 A1 | 10/2007 | Paden et al. |
| 2007/0260242 A1 | 11/2007 | Dycus et al. |
| 2007/0265613 A1 | 11/2007 | Edelstein et al. |
| 2007/0282358 A1 | 12/2007 | Remiszewski et al. |
| 2008/0015575 A1 | 1/2008 | Odom et al. |
| 2008/0064921 A1 | 3/2008 | Larkin et al. |
| 2008/0071269 A1 | 3/2008 | Hilario et al. |
| 2008/0081948 A1 | 4/2008 | Weisenburgh et al. |
| 2008/0114355 A1 | 5/2008 | Whayne et al. |
| 2008/0125794 A1 | 5/2008 | Brock et al. |
| 2008/0147058 A1 | 6/2008 | Horrell et al. |
| 2008/0147062 A1 | 6/2008 | Truckai et al. |
| 2008/0188755 A1 | 8/2008 | Hart |
| 2008/0281315 A1 | 11/2008 | Gines |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0182327 A1 | 7/2009 | Unger |
| 2009/0182332 A1 | 7/2009 | Long et al. |
| 2009/0248021 A1 | 10/2009 | McKenna |
| 2009/0248037 A1 | 10/2009 | Prisco |
| 2009/0248041 A1 | 10/2009 | Williams et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0168520 A1 | 7/2010 | Poll et al. |
| 2010/0222752 A1 | 9/2010 | Collins, Jr. et al. |
| 2010/0228264 A1 | 9/2010 | Robinson et al. |
| 2010/0274278 A1 | 10/2010 | Fleenor et al. |
| 2011/0028964 A1 | 2/2011 | Edwards |
| 2011/0230719 A1 | 9/2011 | Katakura et al. |
| 2011/0290856 A1 | 12/2011 | Shelton, IV et al. |
| 2011/0295295 A1 | 12/2011 | Shelton, IV et al. |
| 2011/0301414 A1 | 12/2011 | Hotto et al. |
| 2011/0306840 A1 | 12/2011 | Allen et al. |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0109186 A1 | 5/2012 | Parrott et al. |
| 2012/0111920 A1 | 5/2012 | Kostrzewski |
| 2012/0116222 A1 | 5/2012 | Sawada et al. |
| 2012/0116265 A1 | 5/2012 | Houser et al. |
| 2012/0132018 A1 | 5/2012 | Tang et al. |
| 2012/0238827 A1 | 9/2012 | Berry et al. |
| 2012/0303025 A1 | 11/2012 | Garrison |
| 2013/0023915 A1 | 1/2013 | Mueller |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0331730 A1 | 12/2013 | Fenech et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0066944 A1 | 3/2014 | Taylor et al. |
| 2014/0207135 A1 | 7/2014 | Winter |
| 2014/0246477 A1 | 9/2014 | Koch, Jr. et al. |
| 2014/0263552 A1 | 9/2014 | Hall et al. |
| 2014/0276944 A1 | 9/2014 | Farritor et al. |
| 2014/0343569 A1 | 11/2014 | Turner |
| 2014/0371763 A1 | 12/2014 | Poll et al. |
| 2015/0038981 A1 | 2/2015 | Kilroy et al. |
| 2015/0080876 A1 | 3/2015 | Worrell et al. |
| 2015/0114404 A1 | 4/2015 | Czop et al. |
| 2015/0272659 A1 | 10/2015 | Boudreaux et al. |
| 2016/0015261 A1 | 1/2016 | Kishi et al. |
| 2016/0051316 A1 | 2/2016 | Boudreaux |
| 2016/0113728 A1 | 4/2016 | Piron et al. |
| 2016/0175028 A1 | 6/2016 | Trees et al. |
| 2016/0346930 A1 | 12/2016 | Hares |
| 2016/0361122 A1 | 12/2016 | Seeber |
| 2016/0361127 A1 | 12/2016 | Dachs, II et al. |
| 2017/0028562 A1 | 2/2017 | Yamazaki et al. |
| 2017/0079708 A1 | 3/2017 | Gilbert et al. |
| 2017/0079730 A1 | 3/2017 | Azizian et al. |
| 2017/0105785 A1 | 4/2017 | Shelton, IV et al. |
| 2017/0135771 A1 | 5/2017 | Auld et al. |
| 2017/0188802 A1 | 7/2017 | Lawrence et al. |
| 2017/0224428 A1 | 8/2017 | Kopp |
| 2017/0333145 A1 | 11/2017 | Griffiths et al. |
| 2018/0085175 A1 | 3/2018 | Steinle et al. |
| 2018/0192862 A1 | 7/2018 | Ide |
| 2018/0289427 A1 | 10/2018 | Griffiths et al. |
| 2018/0296286 A1 | 10/2018 | Peine et al. |
| 2019/0053866 A1 | 2/2019 | Seow et al. |
| 2019/0059986 A1 | 2/2019 | Shelton, IV et al. |
| 2019/0083182 A1 | 3/2019 | Roach et al. |
| 2019/0094084 A1 | 3/2019 | Swinehart et al. |
| 2019/0104919 A1 | 4/2019 | Shelton, IV et al. |
| 2019/0125457 A1 | 5/2019 | Parihar et al. |
| 2019/0133703 A1 | 5/2019 | Seow et al. |
| 2019/0167267 A1 | 6/2019 | Kobayashi et al. |
| 2019/0183596 A1 | 6/2019 | Dachs, II |
| 2019/0200844 A1 | 7/2019 | Shelton, IV et al. |
| 2019/0200981 A1 | 7/2019 | Harris et al. |
| 2019/0201045 A1 | 7/2019 | Yates et al. |
| 2019/0201135 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0298471 A1 | 10/2019 | Holop |
| 2019/0314107 A1 | 10/2019 | Worrell et al. |
| 2019/0321112 A1 | 10/2019 | Cecil |
| 2019/0328469 A1 | 10/2019 | Ando et al. |
| 2019/0357884 A1 | 11/2019 | Williams et al. |
| 2020/0000536 A1 | 1/2020 | Yakimovich et al. |
| 2020/0054412 A1 | 2/2020 | Fuerst et al. |
| 2020/0078109 A1 | 3/2020 | Steger et al. |
| 2020/0093554 A1* | 3/2020 | Schuh .............. A61B 34/71 |
| 2020/0197108 A1 | 6/2020 | Usui |
| 2020/0214776 A1 | 7/2020 | Hingwe et al. |
| 2020/0246063 A1 | 8/2020 | Shelton, IV et al. |
| 2020/0281675 A1 | 9/2020 | Meglan |
| 2020/0315715 A1 | 10/2020 | Rockrohr et al. |
| 2020/0315721 A1 | 10/2020 | Rabindran et al. |
| 2020/0405401 A1 | 12/2020 | Shelton, IV et al. |
| 2020/0405415 A1 | 12/2020 | Shelton, IV et al. |
| 2020/0405421 A1 | 12/2020 | Luck |
| 2021/0015519 A1 | 1/2021 | Meglan et al. |
| 2021/0059777 A1 | 3/2021 | Overmyer et al. |
| 2021/0068889 A1 | 3/2021 | Shelton, IV et al. |
| 2021/0093409 A1 | 4/2021 | Overmyer et al. |
| 2021/0196356 A1* | 7/2021 | Shelton, IV ........ A61B 17/29 |
| 2021/0212777 A1 | 7/2021 | Cheng |
| 2021/0401524 A1* | 12/2021 | Suresh ............. A61B 34/35 |
| 2022/0031350 A1* | 2/2022 | Witte ............... A61B 17/072 |
| 2022/0054208 A1* | 2/2022 | Cooper ............. A61B 34/35 |
| 2022/0202437 A1 | 6/2022 | Overmyer et al. |
| 2022/0202514 A1 | 6/2022 | Boudreaux |
| 2022/0202517 A1 | 6/2022 | Overmyer et al. |
| 2022/0287782 A1 | 9/2022 | Shelton, IV et al. |
| 2023/0000491 A1 | 1/2023 | Wise et al. |
| 2023/0000542 A1 | 1/2023 | Murrell |
| 2023/0001579 A1 | 1/2023 | Overmyer et al. |
| 2023/0320776 A1 | 10/2023 | Shelton, IV et al. |

FOREIGN PATENT DOCUMENTS

| | | |
|---|---|---|
| DE | 29623113 U1 | 10/1997 |
| DE | 20004812 U1 | 9/2000 |
| DE | 10201569 A1 | 7/2003 |
| EP | 0705571 A1 | 4/1996 |
| EP | 2060238 A1 | 5/2009 |
| EP | 1747761 B1 | 10/2009 |
| JP | H08229050 A | 9/1996 |
| SU | 578972 A1 | 11/1977 |
| WO | WO-8103272 A1 | 11/1981 |

(56) References Cited

FOREIGN PATENT DOCUMENTS

| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-2004078051 A2 | 9/2004 |
| WO | WO-2010104755 A1 | 9/2010 |
| WO | WO-2012044606 A2 | 4/2012 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Heat-induced changes in the mechanics of a collagenous tissue: pseudoelastic behavior at 37° C," Journal of Biomechanics, 31, pp. 211-216 (1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Covidien Brochure, [Value Analysis Brief], LigaSure Advance™ Pistol Grip, dated Rev. Apr. 2010 (7 pages).

Covidien Brochure, LigaSure Atlas™ Hand Switching Instruments, dated Dec. 2008 (2 pages).

Covidien Brochure, LigaSure Impact™ Instrument LF4318, dated Feb. 2013 (3 pages).

Covidien Brochure, The LigaSure Precise™ Instrument, dated Mar. 2011 (2 pages).

Covidien Brochure, The LigaSure™ 5 mm Blunt Tip Sealer/Divider Family, dated Apr. 2013 (2 pages).

Douglas, S.C. "Introduction to Adaptive Filter". Digital Signal Processing Handbook. Ed. Vijay K. Madisetti and Douglas B. Williams. Boca Raton: CRC Press LLC, 1999.

Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Glaser and Subak-Sharpe, Integrated Circuit Engineering, Addison-Wesley Publishing, Reading, MA (1979). (book—not attached).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Henriques. F.C., "Studies in thermal injury V. The predictability and the significance of thermally induced rate processes leading to irreversible epidermal injury." Archives of Pathology, 434, pp. 489-502 (1947).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Humphrey, J.D., "Continuum Thermomechanics and the Clinical Treatment of Disease and Injury," Appl. Mech. Rev., vol. 56, No. 2 pp. 231-260 (Mar. 2003).

IEEE Std 802.Mar. 2012 (Revision of IEEE Std 802.3-2008, published Dec. 28, 2012.

International Preliminary Report on Patentability, Application No. PCT/US2013/046777, dated Dec. 31, 2014 (5 pages).

International Search Report, Application No. PCT/US2013/046777, dated Oct. 1, 2013 (4 pages).

Jang, J. et al. "Neuro-fuzzy and Soft Computing." Prentice Hall, 1997, pp. 13-89, 199-293, 335-393, 453-496, 535-549.

Kurt Gieck & Reiner Gieck, Engineering Formulas § Z.7 (7th ed. 1997).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

National Semiconductors Temperature Sensor Handbook—http://www.national.com/appinfo/tempsensors/files/temphb.pdf; accessed online: Apr. 1, 2011.

Sullivan, "Cost-Constrained Selection of Strand Diameter and No. in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

Wall et al., "Thermal modification of collagen," J Shoulder Elbow Surg, No. 8, pp. 339-344 (Jul./Aug. 1999).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Wright, et al., "Time-Temperature Equivalence of Heat-Induced Changes in Cells and Proteins," Feb. 1998. ASME Journal of Biomechanical Engineering, vol. 120, pp. 22-26.

\* cited by examiner

LINK-DRIVEN ARTICULATION DEVICE FOR A SURGICAL DEVICE

BACKGROUND

The present disclosure relates to surgical devices, including robotic tools and handheld surgical instruments having an articulation joint.

SUMMARY

In one general aspect, the present disclosure provides a robotic surgical tool, comprising an end effector, an elongate shaft defining a longitudinal axis, and an articulation joint. The articulation joint comprises a pivot plate attached to the end effector, a fixed plate attached to the elongate shaft, and a spherical joint coupled to the pivot plate and the fixed plate. The robotic surgical tool further comprises an articulation drive system. The articulation drive system comprises a first rod extending through the elongate shaft and movable along a first axis, wherein the first rod comprises a first distal end, a first mechanical link pivotably coupled to the first distal end and pivotably coupled to the pivot plate, and a second rod extending through the elongate shaft and movable along a second axis, wherein the second rod comprises a second distal end. The articulation drive system further comprises a second mechanical link pivotably coupled to the second distal end and pivotably coupled to the pivot plate, a third rod extending through the elongate shaft and movable along a third axis, wherein translation of the first rod and the third rod generates complementary push-pull forces on the pivot plate, and wherein the third rod comprises a third distal end. The articulation drive system further comprises a third mechanical link pivotably coupled to the third distal end and pivotably coupled to the pivot plate, a fourth rod extending through the elongate shaft and movable along a fourth axis, wherein translation of the second rod and the fourth rod generates complementary push-pull forces on the pivot plate, wherein the fourth rod comprises a fourth distal end. The articulation drive system further comprises a fourth mechanical link pivotably coupled to the fourth distal end and pivotably coupled to the pivot plate. The first rod, the second rod, the third rod, and the fourth rod are equidistantly-positioned radially outward from the longitudinal axis and equidistantly-spaced apart within the elongate shaft.

In another aspect, the present disclosure provides a robotic surgical tool, comprising an end effector comprising a pivot member, an elongate shaft defining a longitudinal axis and comprising a fixed member, and an articulation system. The articulation system comprises a first connection between the end effector and the elongate shaft, wherein the first connection comprises a constant velocity joint coupled between the pivot member and the fixed member. The articulation system further comprises a second connection between the end effector and the elongate shaft, wherein the second connection comprises a first series of linkages. The articulation system further comprises a third connection between the end effector and the elongate shaft, wherein the third connection comprises a second series of linkages. Movement of the first series of linkages and the third series of linkages generate complementary push-pull forces on the end effector. The articulation system further comprises a fourth connection between the end effector and the elongate shaft, wherein the fourth connection comprises a third series of linkages. The articulation system further comprises a fifth connection between the end effector and the elongate shaft, wherein the fifth connection comprises a fourth series of linkages. Movement of the second series of linkages and the fourth series of linkages generate complementary push-pull forces on the end effector.

In another aspect, the present disclosure provides a robotic surgical tool, comprising an end effector comprising a pivot member, an elongate shaft defining a longitudinal axis and comprising a fixed member, an articulation joint comprising a constant velocity joint coupled to the pivot member and the fixed member, and an articulation drive system. The articulation drive system comprises a first push-pull rod extending through the elongate shaft and movable along a first axis, wherein the first push-pull rod comprises first distal end. The articulation drive system further comprises a first mechanical link pivotably coupled to the first distal end and pivotably coupled to the pivot member, and a second push-pull rod extending through the elongate shaft and movable along a second axis, wherein the second push-pull rod comprises a second distal end. The articulation drive system further comprises a second mechanical link pivotably coupled to the second distal end and pivotably coupled to the pivot member, and a third push-pull rod extending through the elongate shaft and movable along a third axis. Translation of the first push-pull rod and the third push-pull rod generates complementary push-pull forces on the pivot member. The third push-pull rod comprises third distal end. The articulation drive system further comprises a third mechanical link pivotably coupled to the third distal end and pivotably coupled to the pivot member, and a fourth push-pull rod extending through the elongate shaft and movable along a fourth axis. Translation of the second push-pull rod and the fourth push-pull rod generates complementary push-pull forces on the pivot member. The fourth push-pull rod comprises a fourth distal end. The articulation drive system further comprises a fourth mechanical link pivotably coupled to the fourth distal end and pivotably coupled to the pivot member. The first push-pull rod, the second push-pull rod, the third push-pull rod, and the fourth push-pull rod are equidistantly-positioned radially outward from the longitudinal axis and equidistantly-spaced apart within the elongate shaft.

BRIEF DESCRIPTION OF THE FIGURES

The novel features of the various aspects are set forth with particularity in the appended claims. The described aspects, however, both as to organization and methods of operation, may be best understood by reference to the following description, taken in conjunction with the accompanying drawings in which:

Corresponding reference characters indicate corresponding parts throughout the several views. The exemplifications set out herein illustrate various aspects of the present disclosure, in one form, and such exemplifications are not to be construed as limiting the scope of the invention in any manner.

DETAILED DESCRIPTION

Figure 1:
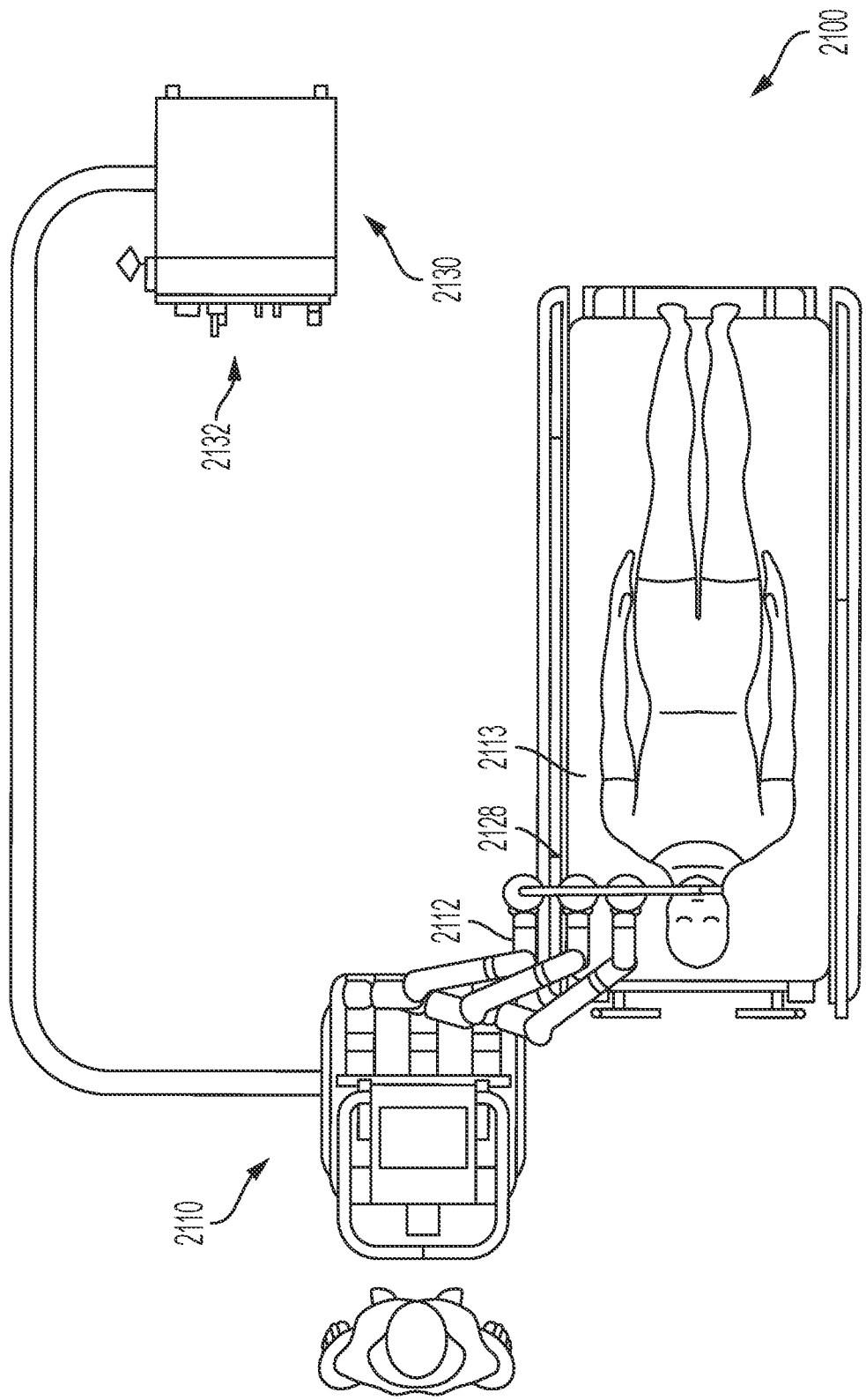
FIG. 1 is a plan view of a surgical procedure depicting a cart-based robotic system arranged for diagnostic and/or therapeutic bronchoscopy procedure(s), in accordance with at least one aspect of the present disclosure.

Applicant of the present application also owns the following U.S. Patent Applications, filed Jun. 30, 2021, each of which is herein incorporated by reference in its entirety:

U.S. patent application Ser. No. 17/363,560, titled GRASPING WORK DETERMINATION AND INDICATIONS THEREOF;

U.S. patent application Ser. No. 17/363,565, titled STAPLE CARTRIDGE REPLACEMENT; and U.S. patent application Ser. No. 17/363,578, titled ELECTROSURGICAL TOOL WITH CAPACITIVE COUPLING MITIGATION SHEATH ASSEMBLY.

Applicant of the present application also owns the following U.S. patent applications, filed Dec. 30, 2020, each of which is herein incorporated by reference in its entirety:

U.S. patent application Ser. No. 17/137,829, titled SURGICAL TOOL WITH TOOL-BASED TRANSLATION AND LOCK FOR THE SAME;

U.S. patent application Ser. No. 17/137,846, titled ROBOTIC SURGICAL TOOLS HAVING DUAL ARTICULATION DRIVES;

U.S. patent application Ser. No. 17/137,852, titled TORQUE-BASED TRANSITION BETWEEN OPERATING GEARS; and U.S. patent application Ser. No. 17/137,857, titled DUAL DRIVING PINION CROSSCHECK.

Applicant of the present application also owns U.S. patent application Ser. No. 16/587,744, filed Sep. 30, 2019, titled COMMUNICATING CLOSURE EFFORT FOR ROBOTIC SURGICAL TOOLS BACKGROUND, which published Apr. 1, 2021 as U.S. Patent Application Publication No. 2021/0093409, which is incorporated by reference herein in its entirety.

Applicant of the present application also owns U.S. patent application Ser. No. 16/553,725, filed Aug. 28, 2019, titled ARTICULATING INCLUDING ANTAGONISTIC CONTROLS FOR ARTICULATION AND CALIBRATION, which published Mar. 4, 2021 as U.S. Patent Application Publication No. 2021/0059777, which is incorporated by reference herein in its entirety.

Applicant of the present application also owns the following U.S. patent applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, which issued May 25, 2021 as U.S. Pat. No. 11,013,563;

U.S. patent application Ser. No. 15/940,676, titled AUTOMATIC TOOL ADJUSTMENTS FOR ROBOT-ASSISTED SURGICAL PLATFORMS, which published Jul. 4, 2019 as U.S. Patent Application Publication No. 2019/0201142; and U.S. patent application Ser. No. 15/940,711, titled SENSING ARRANGEMENTS FOR ROBOT-ASSISTED SURGICAL PLATFORMS, which published Jul. 4, 2019 as U.S. Patent Application Publication No. 2019/0201120.

Applicant of the present application also owns U.S. Provisional patent application Ser. No. 62/611,339, titled ROBOT ASSISTED SURGICAL PLATFORM, filed Dec. 28, 2017, which is incorporated by reference herein in its entirety.

Application of the present application also owns U.S. patent application Ser. No. 13/118,241, titled SURGICAL STAPLING INSTRUMENTS WITH ROTATABLE STAPLE DEPLOYMENT ARRANGEMENTS, filed May 27, 2011, which issued Jul. 7, 2015 as U.S. Pat. No. 9,072,535, which is incorporated by reference herein in its entirety.

U.S. Pat. No. 10,470,830, titled SYSTEM AND METHODS FOR INSTRUMENT BASED INSERTION ARCHI- TECTURES, issued Nov. 12, 2019, is also incorporated by reference herein in its entirety.

Before explaining various aspects of a robotic surgical platforms and surgical devices in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Minimally-invasive surgery (MIS), such as laparoscopic surgery and bronchoscopy, typically involves techniques intended to reduce tissue damage during a surgical procedure. For example, laparoscopic procedures can involve creating a number of small incisions in the patient (e.g., in the abdomen) and introducing one or more surgical tools (e.g., end effectors and an endoscope) through the incisions into the patient. Bronchoscopy can involve passing a bronchoscope through a patient's nose and/or mouth, down the patient's throat, and into the patient's lungs. Surgical procedures may then be performed using the introduced surgical tools and with visualization aid provided by the endoscope, for example.

MIS may provide certain benefits, such as reduced patient scarring, less patient pain, shorter patient recovery periods, and/or lower medical treatment costs associated with patient recovery. Recent technological developments allow robotic systems to perform more MIS procedures. The robotic systems typically include one or more robotic arms for manipulating surgical tools based on commands from a remote operator (e.g. surgeon/clinician). A robotic arm may, for example, support at its distal end various surgical devices such as surgical end effectors, imaging devices, and cannulas for providing access to the patient's body cavity and organs.

Existing robotically-assisted surgical systems typically consist of a surgeon console and a patient-side cart with one or more interactive robotic arms controlled from the console. For example, one robotic arm can support a camera and the other robotic arm(s) can support robotic tools such as scalpels, scissors, graspers, and staplers, for example. Various exemplary robotic tools are further described herein.

A robotic surgical system disclosed herein can be a software-controlled, electro-mechanical system designed for clinicians to perform MIS procedures. The robotic surgical system can be used with an endoscope, compatible endoscopic instruments, and accessories. The system may be used by trained clinicians (e.g. physicians/surgeons) in an operating room environment to assist in the accurate control of compatible endoscopic instruments during robotically-assisted urologic, gynecologic, gastrological, and other laparoscopic surgical procedures. The compatible endoscopic instruments and accessories for use with the surgical system are intended for endoscopic manipulation of tissue including stapling, grasping, cutting, blunt and sharp dissection, approximation, ligation, electrocautery, and suturing, for example.

An exemplary robotic system 2100 is shown in FIG. 1, which depicts a cart-based robotically-enabled system arranged for a diagnostic and/or therapeutic bronchoscopy procedure. During a bronchoscopy, the system 2100 may include a cart 2110 having one or more robotic arms 2112 to deliver a surgical device, such as a steerable endoscope 2113, which may be a procedure-specific bronchoscope for bronchoscopy, to a natural orifice access point (i.e., the mouth of the patient positioned on a table in the present example) to deliver diagnostic and/or therapeutic tools. As shown, the cart 2110 may be positioned proximate to the patient's upper torso in order to provide access to the access point. Similarly, the robotic arms 2112 may be actuated to position the bronchoscope relative to the access point. The arrangement in FIG. 1 may also be utilized when performing a gastro-intestinal (GI) procedure with a gastroscope, a specialized endoscope for GI procedures.

With continued reference to FIG. 1, once the cart 2110 is properly positioned, the robotic arms 2112 may insert the steerable endoscope 2113 into the patient robotically, manually, or a combination thereof. The endoscope 2113 may be directed down the patient's trachea and lungs after insertion using precise commands from the robotic system until reaching the target destination or operative site. For example, the endoscope 2113 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 2113 may endoscopically deliver tools to resect the potentially cancerous tissue. In some instances, diagnostic and therapeutic treatments can be delivered in separate procedures. In those circumstances, the endoscope 2113 may also be used to deliver a fiducial to "mark" the location of the target nodule as well. In other instances, diagnostic and therapeutic treatments may be delivered during the same procedure.

The system 2100 may also include a movable tower 2130, which may be connected via support cables to the cart 2110 to provide support for controls, electronics, fluidics, optics, sensors, and/or power to the cart 2110. Placing such functionality in the tower 2130 allows for a smaller form factor cart 2110 that may be more easily adjusted and/or re-positioned by an operating clinician (e.g. surgeon) and his/her staff. Additionally, the division of functionality between the cart/table and the tower 2130 reduces operating room clutter and facilitates improving clinical workflow. While the cart 2110 may be positioned close to the patient, the tower 2130 may be stowed in a remote location to stay out of the way during a procedure.

In support of the robotic systems described above, the tower 2130 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 2130 or the cart 2110, may control the entire system or sub-system(s) thereof. For example, when executed by a processor of the computer system, the instructions may cause the components of the robotics system to actuate the relevant carriages and arm mounts, actuate the robotics arms, and control the robotic surgical tools. For example, in response to receiving the control signal, the motors in the joints of the robotics arms may position the arms into a certain posture.

The tower 2130 may also include a pump, flow meter, valve control, and/or fluid access in order to provide controlled irrigation and aspiration capabilities to the system that may be deployed through the endoscope 2113. These components may also be controlled using the computer system of tower 2130. In some aspects, irrigation and aspiration capabilities may be delivered directly to the endoscope 2113 through separate cable(s).

The tower 2130 may include a voltage and surge protector designed to provide filtered and protected electrical power to the cart 2110, thereby avoiding placement of a power transformer and other auxiliary power components in the cart 2110, resulting in a smaller, more moveable cart 2110.

The tower 2130 may also include support equipment for the sensors deployed throughout the robotic system 2100. For example, the tower 2130 may include opto-electronics equipment for detecting, receiving, and processing data received from the optical sensors or cameras throughout the robotic system 2100. In combination with the control system, such opto-electronics equipment may be used to generate real-time images for display in any number of consoles deployed throughout the system, including in the tower 2130. Similarly, the tower 2130 may also include an electronic subsystem for receiving and processing signals received from deployed electromagnetic (EM) sensors. The tower 2130 may also be used to house and position an EM field generator for detection by EM sensors in or on the robotic surgical tool. The tower 2130 can also house an electrosurgical generator for supplying RF current to a robotic surgical tool, such as monopolar scissors, for example.

The tower 2130 may also include a console 2132 in addition to other consoles available in the rest of the system, e.g., a console mounted on top of the cart 2110. The console 2132 may include a user interface and a display screen, such as a touchscreen, for the clinician. Consoles in the system 2100 are generally designed to provide both robotic controls as well as pre-operative and real-time information of the procedure, such as navigational and localization information of the endoscope 2113. When the console 2132 is not the only console available to the clinician, it may be used by a second clinician, such as a nurse, for example, to monitor the health or vitals of the patient and the operation of system, as well as provide procedure-specific data, such as navigational and localization information. In other aspects, the console 2132 is housed in a body that is separate from the tower 2130.

The tower 2130 may be coupled to the cart 2110 and endoscope 2113 through one or more cables or connections. In some aspects, the support functionality from the tower 2130 may be provided through a single cable to the cart 2110, simplifying and de-cluttering the operating room. In other aspects, specific functionality may be coupled in separate cabling and connections. For example, while power may be provided through a single power cable to the cart, the support for controls, optics, fluidics, and/or navigation may be provided through one or more separate cables.

Figure 2:
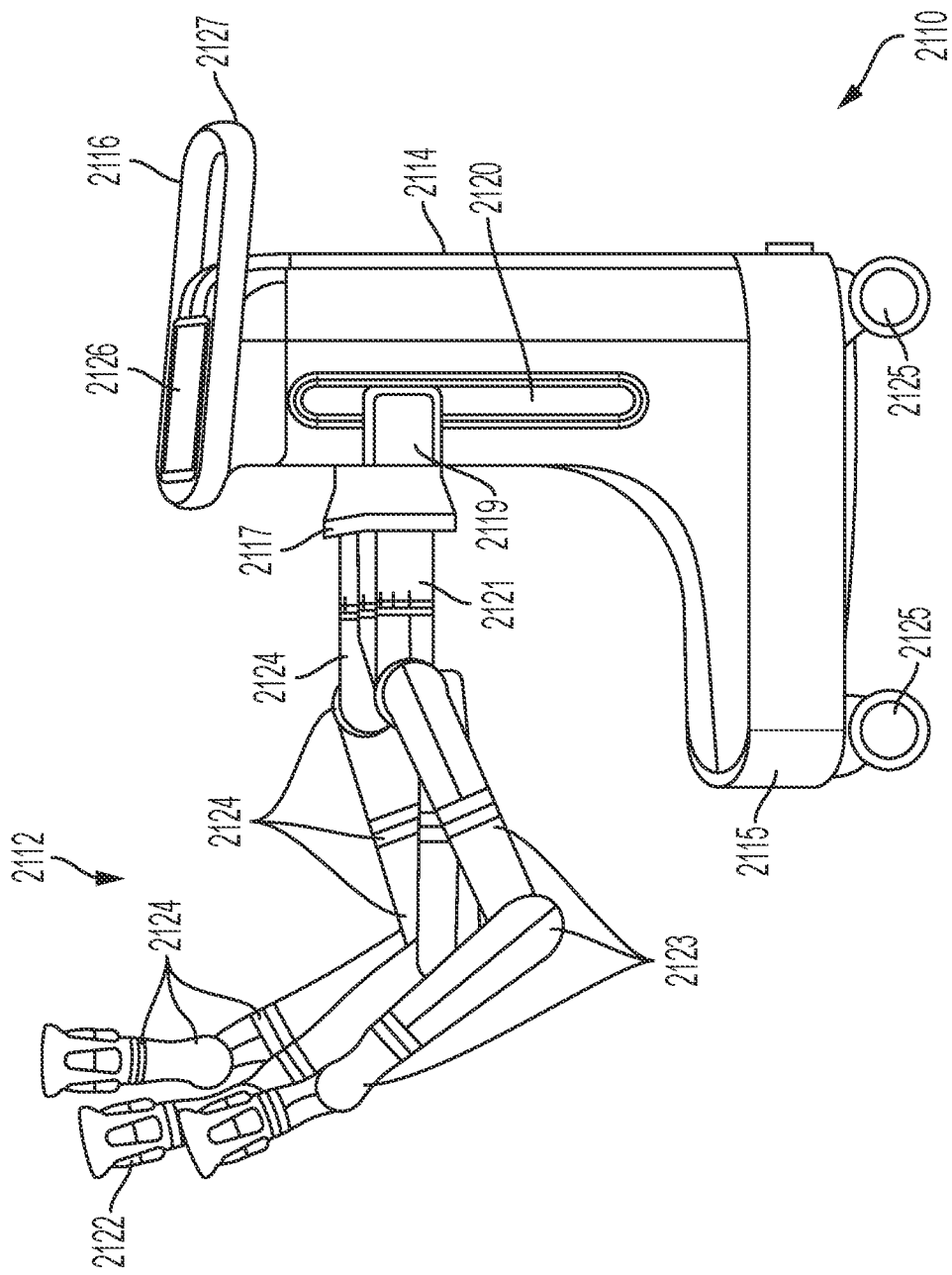
FIG. 2 is a perspective view of a robotic arm cart of the cart-based robotic system of FIG. 1, in accordance with at least one aspect of the present disclosure.

FIG. 2 depicts the cart 2110 from the cart-based robotically-enabled system 2100 shown in FIG. 1. The cart 2110 generally includes an elongated support structure 2114 (often referred to as a "column"), a cart base 2115, and a console 2116 at the top of the elongated support structure 2114. The elongated support structure 2114 may include one or more carriages, such as a carriage 2117 (alternatively "arm support") for supporting the deployment of one or more robotic arms 2112 (three shown in FIG. 2). The carriage 2117 may include individually configurable arm mounts that rotate along a perpendicular axis to adjust the base of the robotic arms 2112 for better positioning relative to the patient. The carriage 2117 also includes a carriage interface 2119 that allows the carriage 2117 to vertically translate along the elongated support structure 2114.

The carriage interface 2119 is connected to the elongated support structure 2114 through slots, such as slot 2120, that are positioned on opposite sides of the elongated support structure 2114 to guide the vertical translation of the carriage 2117. The slot 2120 contains a vertical translation interface to position and hold the carriage at various vertical heights relative to the cart base 2115. Vertical translation of the carriage 2117 allows the cart 2110 to adjust the reach of the robotic arms 2112 to meet a variety of table heights, patient sizes, and physician preferences. Similarly, the individually configurable arm mounts on the carriage 2117 allow the robotic arm base 2121 of robotic arms 2112 to be angled in a variety of configurations.

The elongated support structure 2114 may include internal mechanisms, such as gears and motors, that are designed to use a vertically aligned lead screw to translate the carriage 2117 in a mechanized fashion in response to control signals generated in response to user inputs, e.g., inputs from the console 2116.

The robotic arms 2112 may generally include robotic arm bases 2121 and tool drivers 2122, separated by a series of linkages 2123 that are connected by a series of joints 2124, each joint including an independent actuator, each actuator including an independently controllable motor. Each independently controllable joint represents an independent degree of freedom available to the robotic arm. Each of the arms 2112 have seven joints, and thus provide seven degrees of freedom. A multitude of joints result in a multitude of degrees of freedom, allowing for "redundant" degrees of freedom. Redundant degrees of freedom allow the robotic arms 2112 to position their respective tool drivers 2122 at a specific position, orientation, and trajectory in space using different linkage positions and joint angles. This allows for the system to position and direct a robotic surgical tool from a desired point in space while allowing the clinician to move the arm joints into a clinically advantageous position away from the patient to create greater access while avoiding arm collisions.

The cart base 2115 balances the weight of the elongated support structure 2114, carriage 2117, and arms 2112 over the floor. Accordingly, the cart base 2115 houses heavier components, such as electronics, motors, power supply, as well as components that either enable movement and/or immobilize the cart. For example, the cart base 2115 includes rollable wheel-shaped casters 2125 that allow for the cart 2110 to easily move around the room prior to a procedure. After reaching the appropriate position, the casters 2125 may be immobilized using wheel locks to hold the cart 2110 in place during the procedure.

Positioned at a vertical end of elongated support structure 2114, the console 2116 allows for both a user interface for receiving user input and a display screen (or a dual-purpose device such as, for example, a touchscreen 2126) to provide the clinician with both pre-operative and intra-operative data. Potential pre-operative data on the touchscreen 2126 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 2116 may be positioned and tilted to allow a clinician to access the console from the side of the elongated support structure 2114 opposite carriage 2117. From this position, the clinician may view the console 2116, robotic arms 2112, and patient while operating the console 2116 from behind the cart 2110. As shown, the console 2116 also includes a handle 2127 to assist with maneuvering and stabilizing cart 2110.

The distal end of the system's robotic arms include the tool driver 2122 (alternatively referred to as "instrument drive mechanism" or "instrument device manipulator" (IDM)) that incorporate electro-mechanical means for actuating the robotic tool. A removable or detachable robotic tool can be releasably mounted to the tool driver 2122. The robotic tool can be devoid of any electro-mechanical components, such as motors. This dichotomy may be driven by the need to sterilize robotic surgical tools used in medical procedures, and the inability to adequately sterilize expensive capital equipment due to their intricate mechanical assemblies and sensitive electronics. Accordingly, the robotic surgical tools may be designed to be detached, removed, and interchanged from the instrument driver (and thus the system) for individual sterilization or disposal by the clinician or the clinician's staff. In contrast, the instrument drivers need not be changed or sterilized, and may be draped for protection.

Figure 3:
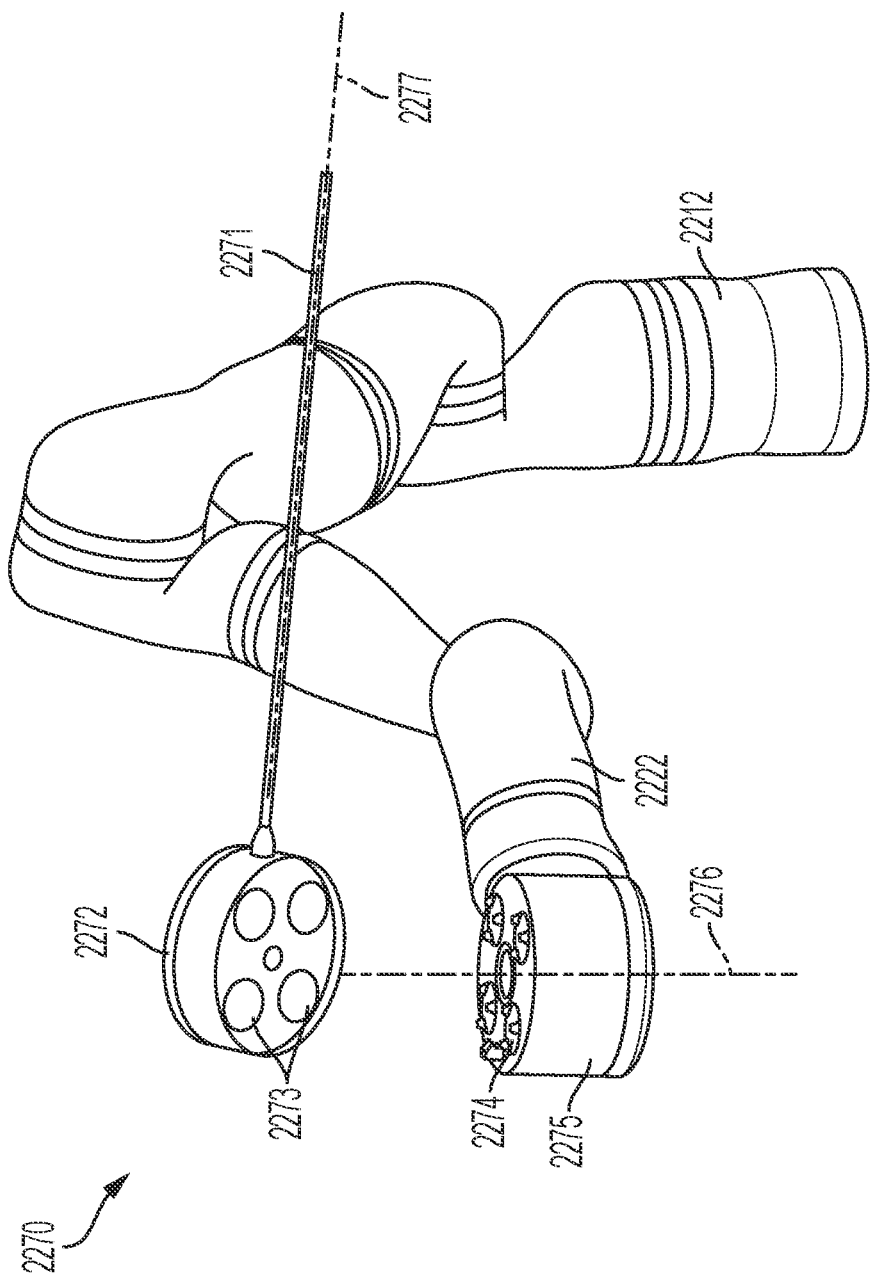
FIG. 3 is a perspective view of a robotic arm having a tool driver and a paired robotic tool detached from the tool driver, in accordance with at least one aspect of the present disclosure.
Figure 4:
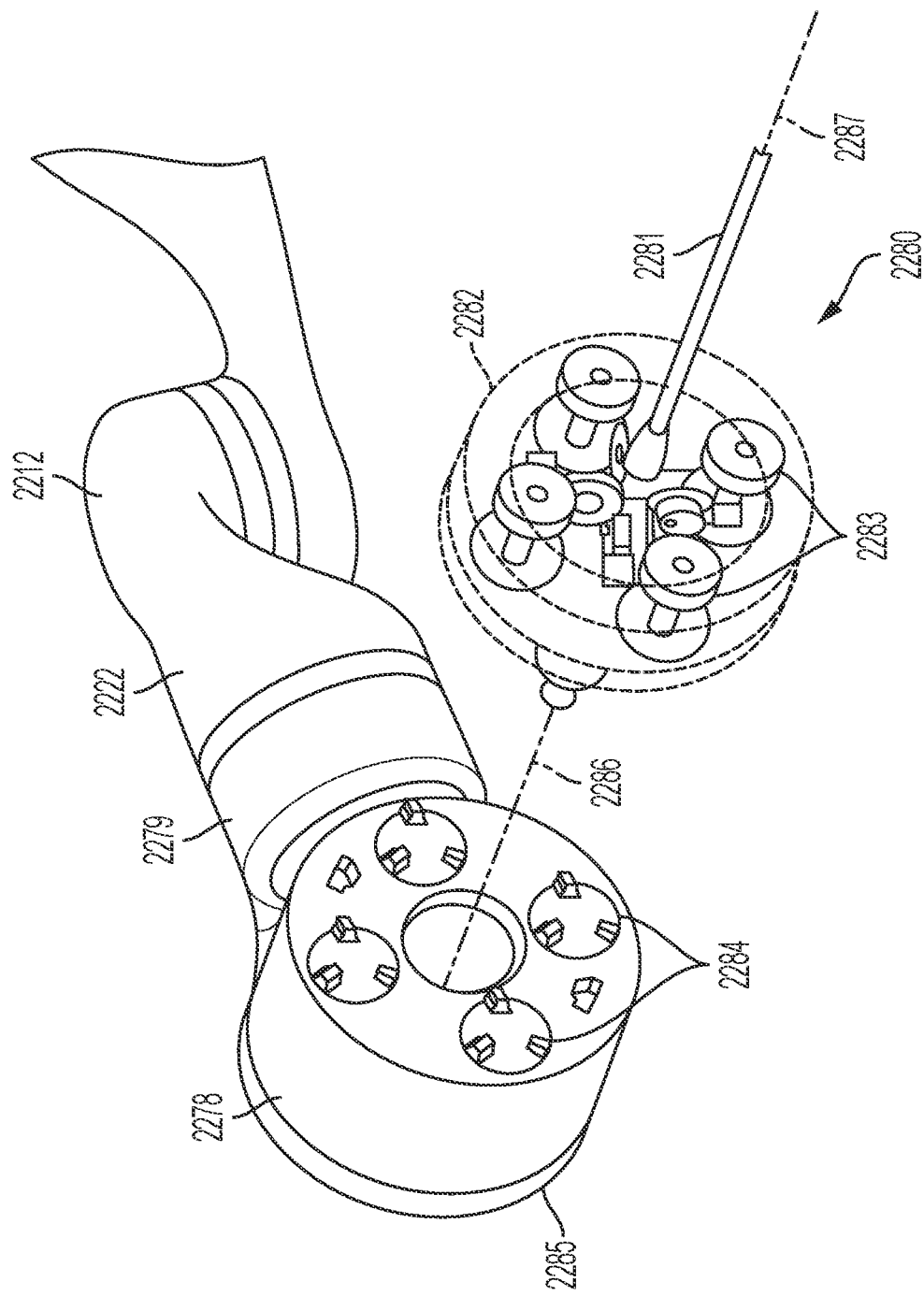
FIG. 4 is another perspective view of the robotic arm of FIG. 3 having a tool driver and a paired robotic tool detached from the tool driver, in accordance with at least one aspect of the present disclosure.

FIGS. 3 and 4 illustrate an example tool driver paired with a robotic surgical tool. The tool drivers are positioned at the distal end 2222 of a robotic arm 2212, which can be similar in many aspects to the robotic arms 2112. Positioned at the distal end 2222 of the robotic arm 2212, the tool drivers comprises one or more drive units arranged with parallel axes to provide controlled torque to a robotic surgical tool via drive shafts. Each drive unit includes an individual drive shaft for interacting with the instrument, a gear head for converting the motor shaft rotation to a desired torque, a motor for generating the drive torque, an encoder to measure the speed of the motor shaft and provide feedback to the control circuitry, and control circuitry for receiving control signals and actuating the drive unit. Each drive unit being independently controlled and motorized, the tool driver may provide multiple (four as shown in FIGS. 3 and 4) independent drive outputs to the robotic surgical tool. In operation, the control circuitry can receive a control signal, transmit a motor signal to the motor, compare the resulting motor speed as measured by the encoder with the desired speed, and modulate the motor signal to generate the desired torque, for example.

For procedures that require a sterile environment, the robotic system may incorporate a drive interface, such as a sterile adapter connected to a sterile drape, that sits between the tool driver and the robotic surgical tool. The chief purpose of the sterile adapter is to transfer angular motion from the drive shafts of the tool driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the tool driver and drive inputs on the instrument. Connected to the sterile adapter, the sterile drape, comprised of a thin, flexible material such as transparent or translucent plastic, is designed to cover the capital equipment, such as the tool driver, the robotic arm, and the cart (in a cart-based system) or table (in a table-based system). Use of the drape would allow the capital equipment to be positioned proximate to the patient while still being located in an area not requiring sterilization (i.e., non-sterile field). On the other side of the sterile drape, the robotic surgical tool may interface with the patient in an area requiring sterilization (i.e., sterile field).

Robotic surgical platforms like the robotic surgical system 2100 are further described in U.S. Patent Application Publication No. 2021/0059777, titled ARTICULATING INCLUDING ANTAGONISTIC CONTROLS FOR ARTICULATION AND CALIBRATION, published Mar. 4, 2021. U.S. Patent Application Publication No. 2021/0059777, titled ARTICULATING INCLUDING ANTAGONISTIC CONTROLS FOR ARTICULATION AND CALIBRATION, published Mar. 4, 2021 is incorporated by reference herein in its entirety.

FIG. 3 depicts a robotic surgical tool 2270 with a paired tool driver 2275. The tool driver 2275 can be coupled to a distal end 2222 of the robotic arm 2212. Like other surgical tools designed for use with a robotic system, the robotic surgical tool 2270 includes an elongated shaft 2271 (or elongate body) and a housing (or base) 2272. The housing 2272, can also be referred to as an "instrument handle" due to its intended design for manual interaction by the clinician when attaching or coupling the surgical tool 2270 to the tool driver 2275 on the robotic arm 2212. The housing 2272 includes rotatable drive inputs 2273, e.g., receptacles, pulleys or spools, that are designed to be mated with drive outputs 2274 that extend through a drive interface on tool driver 2275 at the distal end 2222 of the robotic arm 2212. When physically connected, latched, and/or coupled, the mated drive inputs 2273 of housing 2272 may share axes of rotation with the drive outputs 2274 in the tool driver 2275 to allow the transfer of torque from drive outputs 2274 to drive inputs 2273. In some instances, the drive outputs 2274 may include splines that are designed to mate with receptacles on the drive inputs 2273. The drive outputs 2274 (and drive inputs 2273 when drivingly coupled thereto) are configured to rotate about axes parallel with a central axis 2276 defined through the tool driver 2275.

The elongated shaft 2271 is designed to be delivered through either an anatomical opening or lumen, e.g., as in endoscopy, or a minimally invasive incision, e.g., as in laparoscopy. The elongated shaft 2271 may be either flexible (e.g., having properties similar to an endoscope) or rigid (e.g., having properties similar to a laparoscope) or contain a customized combination of both flexible and rigid portions. In an unflexed configuration, the elongated shaft 2271 extends along a longitudinal axis 2277, which is transverse to the central axis 2276 of the tool driver 2275. When designed for laparoscopy, the distal end of a rigid elongated shaft may be connected to an end effector extending from a jointed wrist formed from a clevis with at least one degree of freedom and a surgical tool or robotic surgical tool, such as, for example, a grasper, scissors, a stapler, or other surgical device. The end effector can be actuated based on force from the tendons as the drive inputs 2273 rotate in response to torque received from the drive outputs 2274 of the tool driver 2275. Various highly articulatable robotic surgical tools are further described herein. When designed for endoscopy, the distal end of a flexible elongated shaft may include a steerable or controllable bending section that may be articulated and bent based on torque received from the drive outputs 2274 of the tool driver 2275.

Torque from the tool driver 2275 is transmitted down the elongated shaft 2271 using tendons along the shaft 2271. These individual tendons, such as pull wires, may be individually anchored to individual drive inputs 2273 within the housing 2272. From the housing 2272, the tendons are directed down one or more pull lumens along the elongated shaft 2271 and anchored at the distal portion of the elongated shaft 2271 or in the wrist at the distal portion of the elongated shaft 2271. During a surgical procedure, such as a laparoscopic, endoscopic or hybrid procedure, these tendons may be coupled to a distally mounted end effector, such as a grasper or scissors, for example. Under such an arrangement, torque exerted on drive inputs 2273 would transfer tension to the tendon, thereby causing the end effector to actuate in some way. In some instances, during a surgical procedure, the tendon may cause a joint to rotate about an axis, thereby causing the end effector to move in one direction or another. Alternatively, the tendon may be connected to one or more jaws of a grasper at distal end of the elongated shaft 2271, where tension from the tendon cause the grasper to close.

In endoscopy, the tendons may be coupled to a bending or articulating section positioned along the elongated shaft 2271 (e.g., at the distal end) via adhesive, a control ring, or other mechanical fixation. When fixedly attached to the distal end of a bending section, torque exerted on drive inputs 2273 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 2271 to allow for controlled articulation in the desired bending or articulable sections.

In endoscopy, the elongated shaft 2271 houses a number of components to assist with the robotic procedure. The shaft may include a working channel for deploying surgical tools (or robotic surgical tools), irrigation, and/or aspiration to the operative region at the distal end of the shaft 2271. The shaft 2271 may also accommodate wires and/or optical fibers to transfer signals to/from an optical assembly at the distal tip, which may include an optical camera. The shaft 2271 may also accommodate optical fibers to carry light from proximally-located light sources, such as light emitting diodes, to the distal end of the shaft. In various instances, an RF electrode can extend through the elongated shaft 2271 and can be configured to deliver RF energy to a distal end effector of the robotic surgical tool 2270.

At the distal end of the robotic surgical tool 2270, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

Referring still to FIG. 3, the drive shaft axes, and thus the drive input axes, are parallel to the central axis 2276 of the tool driver 2275 and orthogonal to the longitudinal axis 2277 of the elongated shaft. This arrangement, however, can complicate roll capabilities for the elongated shaft 2271 in certain instances. Rolling the elongated shaft 2271 along its longitudinal axis 2277 while keeping the drive inputs 2273 static may result in undesirable tangling of the tendons as they extend off the drive inputs 2273 and enter pull lumens within the elongated shaft 2271. The resulting entanglement of such tendons may disrupt any control algorithms intended to predict movement of the flexible elongated shaft during an endoscopic procedure.

FIG. 4 illustrates another tool driver 2285 and a paired robotic surgical tool 2280 where the axes of the drive units are parallel to an axis defined by an elongated shaft 2281 of the surgical tool 2280. As shown, a circular tool driver 2285 comprises four drive units with their drive outputs 2284 aligned in parallel at the end of the robotic arm 2212. The drive units, and their respective drive outputs 2284, are housed in a rotational assembly 2278 of the tool driver 2285 that is driven by one of the drive units within the rotational assembly 2278. In response to torque provided by the rotational drive unit, the rotational assembly 2278 rotates along a circular bearing that connects the rotational assembly 2278 to a non-rotational portion 2279 of the tool driver 2285. Power and controls signals may be communicated from the non-rotational portion 2279 of the tool driver 2285 to the rotational assembly 2278 through electrical contacts, which can be maintained through rotation by a brushed slip ring connection. In other aspects of the present disclosure, the rotational assembly 2278 may be responsive to a separate drive unit that is integrated into the non-rotational portion 2279, and thus not in parallel to the other drive units. The rotational assembly 2278 allows the tool driver 2285 to rotate the drive units, and their respective drive outputs 2284, as a single unit around a tool driver axis 2286.

Similar to the robotic surgical tool 2270, the robotic surgical tool 2280 includes an elongated shaft portion 2281 and a housing 2282 (shown as transparent in FIG. 4 for illustrative purposes) including a plurality of drive inputs 2283 (such as receptacles, pulleys, and spools) that are configured to receive the drive outputs 2284 in the tool driver 2285. Shaft 2281 extends from the center of the housing 2282 along a longitudinal axis 2287 substantially parallel to the axes of the drive inputs 2283, rather than orthogonal thereto as in the arrangement shown in FIG. 3.

When coupled to the rotational assembly 2278 of the tool driver 2285, the robotic surgical tool 2280, comprising the housing 2282 and shaft 2281, rotates in combination with the rotational assembly 2278 about a central axis 2286 defined through the tool driver 2285. Since the shaft 2281 is positioned at the center of the housing 2282, the shaft 2281 is coaxial with tool driver's central axis 2286 when attached. Thus, rotation of the rotational assembly 2278 causes the shaft 2281 to rotate about its own longitudinal axis 2287. Moreover, as the rotational assembly 2278 rotates with the shaft 2281, any tendons connected to the drive inputs 2283 in the housing 2282 are not tangled during rotation. Accordingly, the parallelism of the axes of the drive outputs 2284, drive inputs 2283, and shaft 2281 allows for the shaft rotation without tangling any control tendons.

In other instances, the tool drives may include a different configuration of actuated drives. For example, U.S. Patent Application Publication No. 2019/0201111, titled DRIVE ARRANGEMENTS FOR ROBOTIC-ASSISTED SURGICAL PLATFORMS, which published on Jul. 4, 2019, describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, also describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, and U.S. Patent Application Publication No. 2019/0201111, titled DRIVE ARRANGEMENTS FOR ROBOTIC-ASSISTED SURGICAL PLATFORMS, which published on Jul. 4, 2019, are incorporated by reference herein in their respective entireties. Alternative drive arrangements are further described herein.

Figure 5:
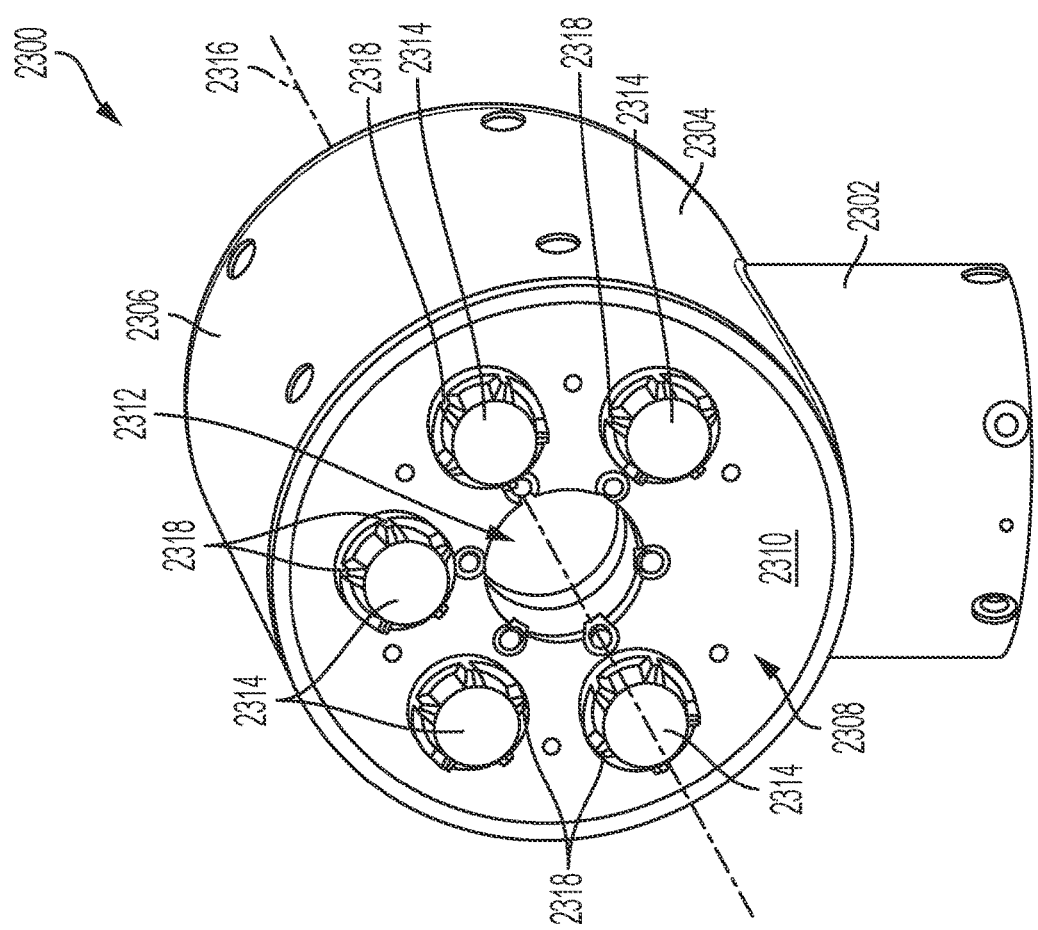
FIG. 5 is a perspective view of a tool driver, in accordance with at least one aspect of the present disclosure.

FIG. 5 depicts a perspective view of another tool driver 2300, which is also referred to herein as an IDM. The tool driver 2300 is similar in many aspects to the tool drivers 2285; however, the tool driver 2300 includes five rotary outputs. Various aspects of the tool driver 2300 are further described in U.S. Pat. No. 10,470,830, titled SYSTEM AND METHODS FOR INSTRUMENT BASED INSERTION ARCHITECTURES, issued Nov. 12, 2019, for example.

The tool driver 2300 can be used with the robotic surgical system 2100 and with the robotic arms 2212, for example. The tool driver 2300 is configured to attach a surgical tool to a robotic arm in a manner that allows the surgical tool to be continuously rotated, or "rolled", about a longitudinal axis of the surgical tool. The tool driver 2300 includes a base 2302 and a surgical tool holder assembly 2304 coupled to the base 2302. The surgical tool holder assembly 2304 serves as a tool holder for holding a robotic surgical tool.

Figure 6:
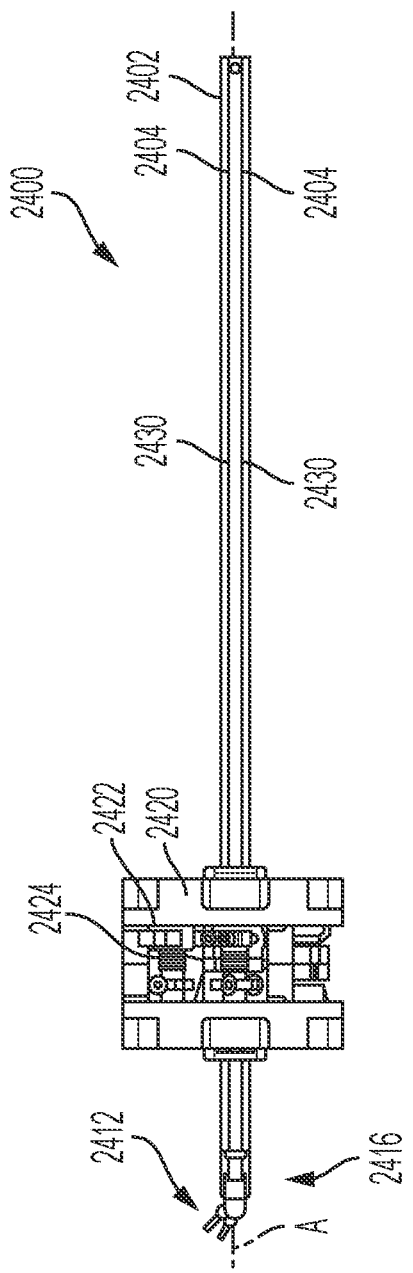
FIG. 6 is an elevation view of a surgical tool for use with the tool driver of FIG. 5, in accordance with at least one aspect of the present disclosure.

The surgical tool holder assembly 2304 further includes an outer housing 2306, a surgical tool holder 2308, an attachment interface 2310, a passage 2312, and a plurality of torque couplers 2314 that have splines 2318. The passage 2312 comprises a through-bore that extends from one face of the tool driver 2300 to an opposing face of the tool driver 2300 along a central axis 2316, which is collinear with a longitudinal axis of the surgical tool coupled thereto. The tool driver 2300 can be used with a variety of surgical tools, which may include a handle, or housing, and an elongated body, or shaft, and which may be for a laparoscope, an endoscope, or other types of surgical tools, such as electrosurgical tools including monopolar RF scissors, for example. An exemplary surgical tool 2400 is shown in FIG. 6, for example.

The base 2302 removably or fixedly mounts the tool driver 2300 to a robotic surgical arm of a robotic surgical system. In FIG. 5, the base 2302 is fixedly attached to the outer housing 2306 of the surgical tool holder assembly 2304. In alternative instances, the base 2302 is structured to include a platform, which is adapted to rotatably receive the surgical tool holder 2308 on the face opposite from the attachment interface 2310. The platform may include a passage aligned with the passage 2312 to receive the elongated body of the surgical tool and, in some instances, an additional elongated body of a second surgical tool mounted coaxially with the first surgical tool. One or more motors can be housed in the base 2302. For example, the surgical tool holder 2308 can include multiple motors, which are configured to drive, i.e. rotate output drives, also referred to herein as torque drivers and torque couplers, 2314 with a torque and rotary velocity, which can be controlled by the controller, for example.

The surgical tool holder assembly 2304 is configured to secure a surgical tool to the tool driver 2300 and rotate the surgical tool relative to the base 2302. Mechanical and electrical connections are provided from the surgical arm to the base 2302 and then to the surgical tool holder assembly 2304 to rotate the surgical tool holder 2308 relative to the outer housing 2306 and to manipulate and/or deliver power and/or signals from the surgical arm to the surgical tool holder 2308 and ultimately to the surgical tool. Signals may include signals for pneumatic pressure, electrical power, electrical signals, and/or optical signals.

The attachment interface 2310 is a face of the surgical tool holder 2308 that attaches to the surgical tool. The attachment interface 2310 includes a first portion of an attachment mechanism that reciprocally mates with a second portion of the attachment mechanism located on the surgical tool. The attachment interface 2310 is further described in U.S. Pat. No. 10,470,830, titled SYSTEM AND METHODS FOR INSTRUMENT BASED INSERTION ARCHITECTURES, issued Nov. 12, 2019, for example.

Various tools can attach to the tool driver 2300, including tools used for laparoscopic, endoscopic and endoluminal surgery. Tools can include tool-based insertion architectures that reduce the reliance on robotic arms for insertion. In other words, insertion of a surgical tool (e.g., towards a surgical site) can be facilitated by the design and architecture of the surgical tool. For example, in some instances, wherein a tool comprises an elongated shaft and a handle, the architecture of the tool enables the elongated shaft to translate longitudinally relative to the handle along an axis of insertion. Various advantages of tool-based insertion architectures are further described in U.S. Pat. No. 10,470,830, titled SYSTEM AND METHODS FOR INSTRUMENT BASED INSERTION ARCHITECTURES, issued Nov. 12, 2019, which is incorporated by reference herein its entirety.

A surgical tool 2400 having a tool-based insertion architecture is shown in FIG. 6. Various aspects of the surgical tool 2400 are further described in U.S. Pat. No. 10,470,830, titled SYSTEM AND METHODS FOR INSTRUMENT BASED INSERTION ARCHITECTURES, issued Nov. 12, 2019, for example.

The surgical tool 2400 enables a translation of the surgical tool 2400 (e.g., translation of its shaft 2402 and end effector 2412 relative to a tool driver and/or distal end of the robotic arm) along an insertion axis. In such instances, the surgical tool 2400 can be moved along the insertion axis without reliance—or with less reliance—on movement of a robotic arm. The surgical tool 2400 includes an elongated shaft 2402, an end effector 2412 connected to the shaft 2402, and a handle 2420, which may also be referred to as an instrument housing or base, coupled to the shaft 2402. The elongated shaft 2402 comprises a tubular member and includes one or more channels or grooves 2404 along its outer surface. The grooves 2404 are configured to receive one or more wires or cables 2430 therethrough. The cables 2430 run along an outer surface of the elongated shaft 2402. In other aspects of the present disclosure, certain cables 2430 can run through the shaft 2402 and may not be exposed. Manipulation of the cables 2430 (e.g., via the tool driver 2300) results in actuation of the end effector 2412, for example.

The end effector 2412 can include laparoscopic, endoscopic, or endoluminal components, for example, and can be designed to provide an effect to a surgical site. For example, the end effector 2412 can comprise a wrist, grasper, tines, forceps, scissors, clamp, knife, and/or fasteners. Exemplary surgical end effectors are further described herein. The cables 2430 that extend along the grooves on the outer surface of the shaft 2402 can actuate the end effector 2412. The cables 2430 extend from a proximal portion of the shaft 2402, through the handle 2420, and toward a distal portion of the shaft 2402, where they actuate the end effector 2412.

The instrument housing 2420 includes an attachment interface 2422 having one or more mechanical inputs 2424, e.g., receptacles, pulleys or spools, that are designed to be reciprocally mated with one or more torque couplers 2314

(FIG. 5) on the attachment interface 2310 of the tool driver 2300. The attachment interface 2422 is capable of attaching to the tool driver 2300 via a front-mount, back-mount and/or top mount. When physically connected, latched, and/or coupled together, the mated mechanical inputs 2424 of the instrument handle 2420 may share axes of rotation with the torque couplers 2314 of the tool driver 2300, thereby allowing the transfer of torque from the motors in the tool driver 2300 to the instrument handle 2420. In some instances, the torque couplers 2314 may comprise splines that are designed to mate with receptacles on the mechanical inputs. Cables 2430 that actuate the end effector 2412 engage the receptacles, pulleys, or spools of the handle 2420, such that the transfer of torque from the tool driver 2300 to the instrument handle 2420 results in actuation of the end effector 2412.

The surgical tool 2400 can include a first actuation mechanism that controls actuation of the end effector 2412. The surgical tool 2400 can also include a second actuation mechanism that enables the shaft 2402 to translate relative to the handle 2420 along an axis of insertion A. One or more additional actuation mechanism can effect articulation of the end effector 2412 relative to the shaft 2402. For example, the surgical tool 2400 can include an articulation joint 2416, which can allow articulation of the end effector 2412 relative to the shaft 2402 about one or more axes.

In various instances, an actuation mechanism can include one or more pulleys mounted on a rotary axis to change relative cable length and, in other instances, mounting a pulley on a lever, gear or track-based system to adjust its location. Additionally or alternatively, ball spline rotary shafts that travel down a length of a tool can also be used to transmit forces in a mechanically-remote way. Various actuation mechanisms are further described in U.S. Pat. No. 10,470,830, titled SYSTEM AND METHODS FOR INSTRUMENT BASED INSERTION ARCHITECTURES, issued Nov. 12, 2019, for example.

In various instances, the surgical tool 2400 can be a surgical stapler, disposable loading unit, or stapling assembly for cutting and stapling tissue. The surgical stapler can integrally include or be adapted to receive one or more staple cartridges (e.g. a replaceable staple cartridge) therein. A staple cartridge can include multiple longitudinal rows of staple cavities and a longitudinal knife slot, in certain instances. Staples are contained within the staple cavities and are configured to be sequentially fired during a firing stroke (e.g. a proximal-to-distal firing stroke) of a firing member (e.g. an E-beam or I-beam) through the staple cartridge. In various instances, a rotary drive shaft can transmit the firing forces to the firing member. For example, rotation of the rotary drive shaft in the end effector can move the firing member during the firing stroke to engage a sled, staple drivers, and/or staple drivers and to drive the staples into tissue.

Figure 7:
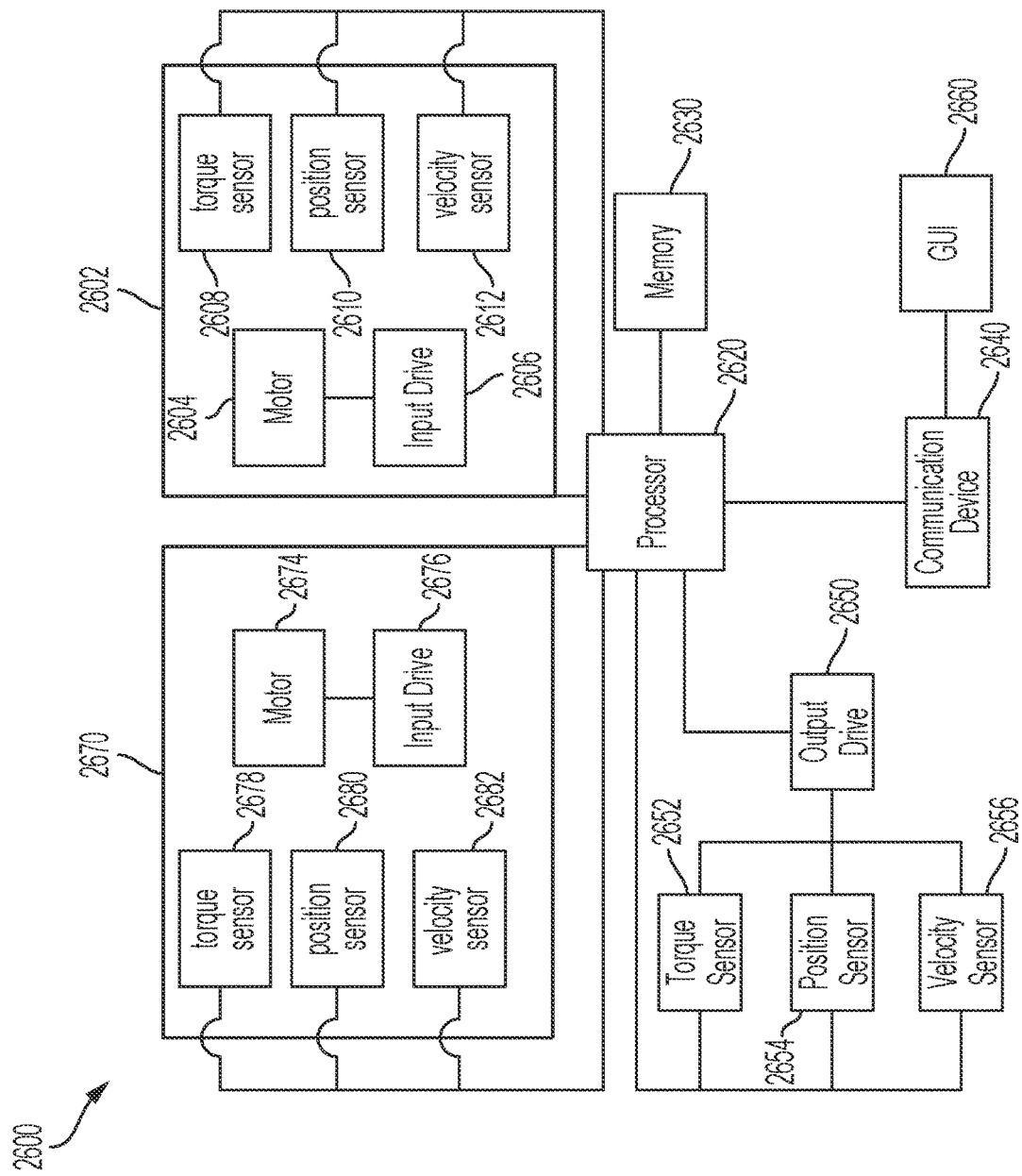
FIG. 7 is a schematic of a control circuit including two input drives, in accordance with at least one aspect of the present disclosure.

A robotic surgical tool (e.g. the robotic surgical tool 2400) can be controlled by a control circuit, such as the control circuit 2600 in FIG. 7, and can be used in conjunction with a robotic surgical system. In such instances, the torque sensor(s) and/or rotary encoder(s) and/or velocity sensor(s) can be monitoring devices, which are configured to monitor operational parameters of the robotic surgical tool 2400. The torque sensors, for instance, can be configured to monitor torque, the rotary encoders can be configured to monitor motion (rotational or linear), and the velocity sensors can be configured to monitor speed (rotational or linear). The torque sensors, the rotary encoders, and the velocity sensors can be incorporated into the motors of some or all of the drivers. Additionally or alternatively, the torque sensors and/or the rotary encoders and/or velocity sensors can be operatively coupled to one or more of the rotary output drives (e.g. output drives 2274 on the tool driver 2275). The torque sensors can be configured to measure the real-time torque loading on the motors, which corresponds to the torque loading by the drivers, and/or the drive inputs, in various instances. The rotary encoders can measure the rotational motion or output of the motors, which corresponds to the rotational motion of the drivers and/or the drive inputs. The velocity sensors can measure the rotational velocity of the motors, which corresponds to the rotational velocity of the drivers and/or the drive inputs. Monitoring torque loading, rotational motion, and rotational velocity of the motors can help determine if the robotic surgical tool 2400 is operating in accordance with the commands provided by the control circuit.

The control circuit 2600 includes two input drives and two motors for controlling articulation of the end effector. For example, articulation drive motors can be positioned in the tool base (e.g. tool driver 2275) for driving articulation of an end effector, for example. The control circuit 2600 includes a processor 2620 in signal communication with a memory 2630 and with a communication device 2640. The communication device can be connected to a graphical user interface (GUI) 2660, where a user can receive information from the processor and provide inputs. A first drive system 2602 and a second drive system 2670 are in signal communication with the processor 2620. The first drive system 2602 includes a motor 2604 (e.g. a pitch articulation motor), an input drive 2606 coupled to the motor 2604, a torque sensor 2608, a rotary encoder/position sensor 2610, and a velocity sensor 2612. The input drive 2606 can correspond to one of the drive outputs 2274, for example. The second drive system 2670 includes a motor 2674 (e.g. a yaw articulation motor), an input drive 2676 coupled to the motor 2674, a torque sensor 2678, a rotary encoder/position sensor 2680, and a velocity sensor 2682. The input drive 2676 can correspond to one of the drive outputs 2274, for example.

In some instances, the torque sensors 2608, 2678 can determine the torque on the motors 2604, 2674, respectively. Moreover, the position sensors 2610, 2680 can determine the angular position of the motors 2604, 2674, respectively, and the velocity sensors 2612, 2682 can determine the angular velocity of the motors 2604, 2674, respectively.

The control circuit 2600 can also include an output drive 2650, a torque sensor 2652, a rotary encoder/position sensor 2654, and a velocity sensor 2656. The output drive 2650 can correspond to any movable joint or actuation of the surgical tool, for example. For example, the torque sensor 2652 can determine the output torque applied to an articulation joint, the position sensor 2654 can determine the angular position of the articulation joint, and the velocity sensor can determine the angular velocity of the articulation joint.

There are many ways to drive an articulation joint in a surgical tool. One common method is using cables to drive the articulation joint. In some instances, cable-driven articulation systems can result in stretching of the cables when articulating under heavy loads, such as the loads produced during certain firing strokes with a surgical stapler, for example. To prevent the potential stretching, or over stretching, of cables, an articulation joint system can utilize mechanical links instead or, or in addition to, cables. By using mechanical links, the articulation system may be configured to withstand heavier loads without damaging the articulation system in certain instances.

Figure 8:
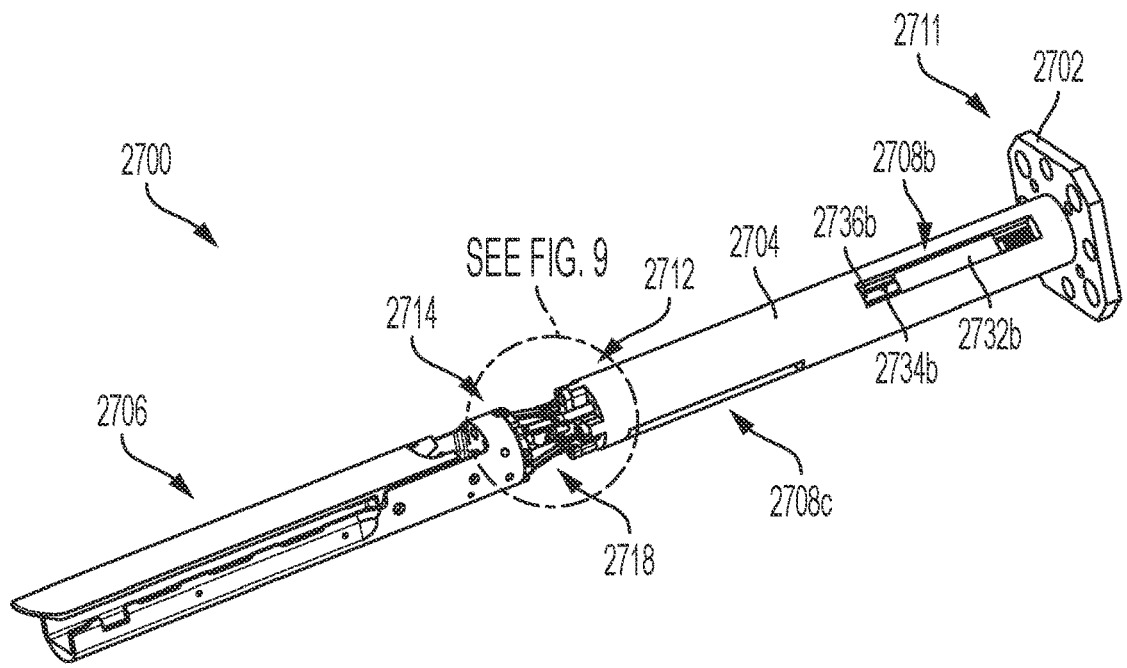
FIG. 8 is a perspective view of part of a surgical tool showing an end effector, a shaft, and an articulation joint, in accordance with at least one aspect of the present disclosure.
Figure 22:
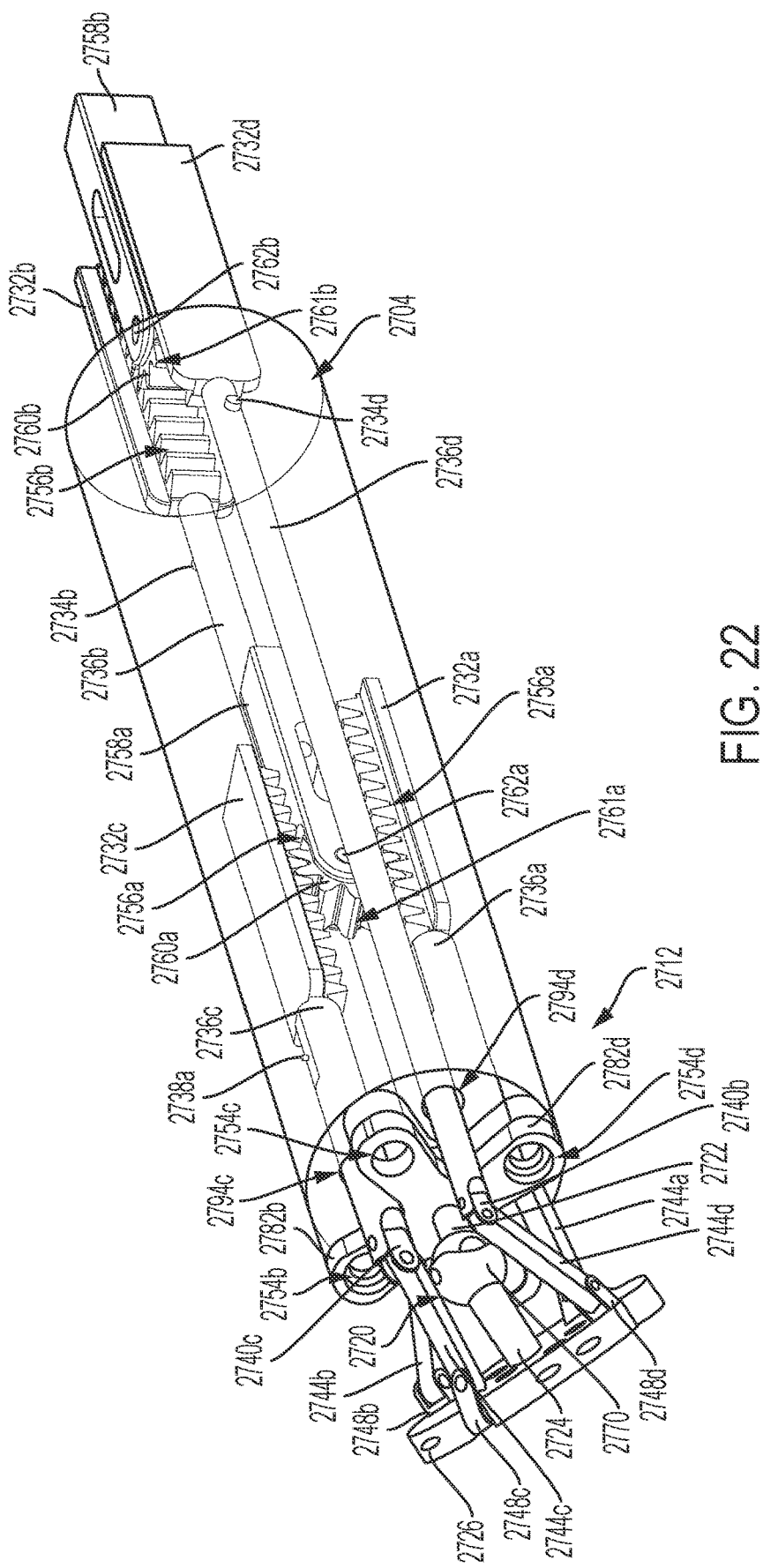
FIG. 22 is an isometric view of the articulation system for the surgical tool, shown in FIG. 8, in an articulated position, in accordance with at least one aspect of the present disclosure.
Figure 23:
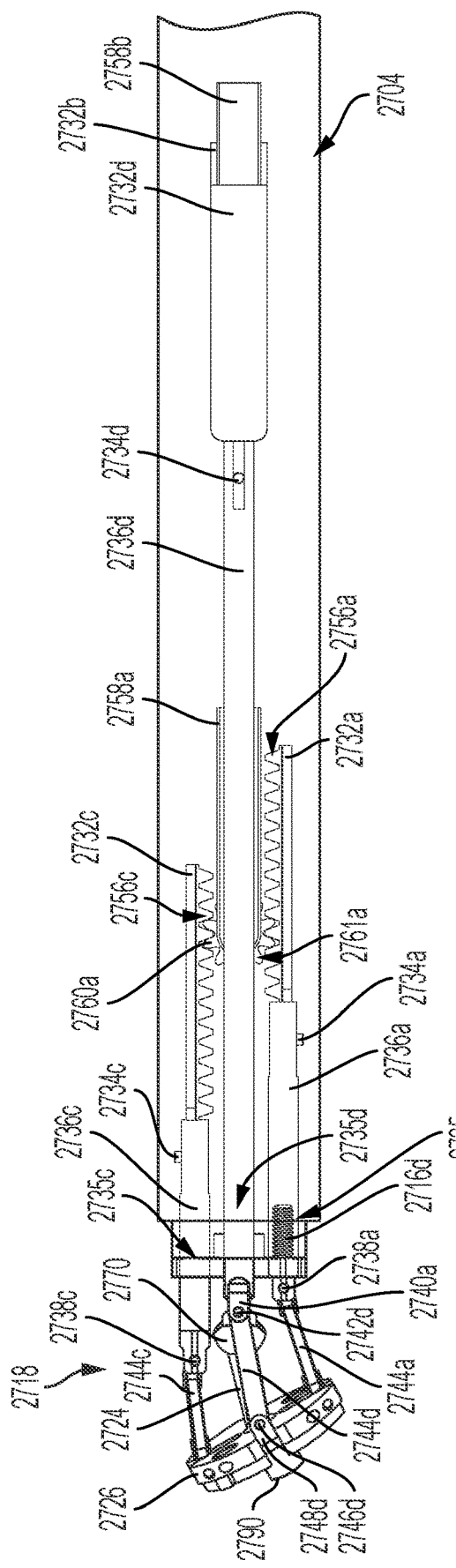
FIG. 23 is a top view of the articulation system shown in FIG. 22, in accordance with at least one aspect of the present disclosure.
Figure 24:
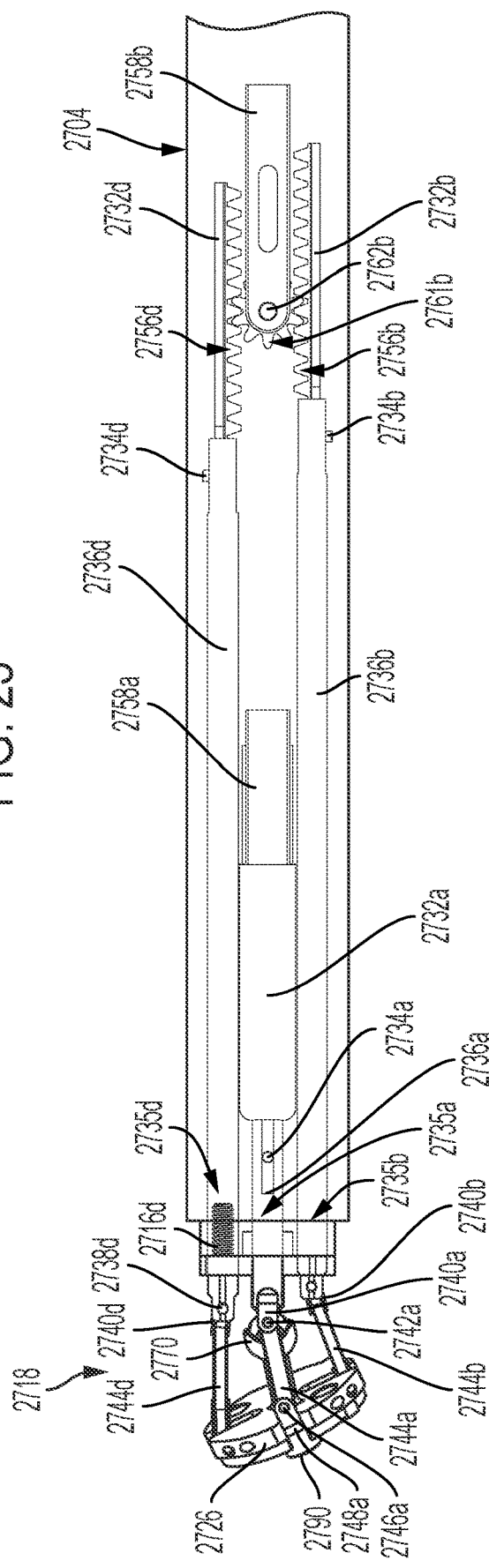
FIG. 24 is a side view of the articulation system shown in FIG. 22, in accordance with at least one aspect of the present disclosure.

FIGS. 8-24 depict an articulation system that is driven by a series of mechanical links. FIGS. 8-21 show the articulation system in an unarticulated position, and FIGS. 22-24 show the articulation system in an articulated position. Referring primarily to FIG. 8, a surgical tool 2700 includes an end effector 2706, an articulation joint 2718, and a shaft 2704. The shaft 2704 has a proximal end 2711 and a distal end 2712 and defines a longitudinal axis along the center of the shaft between the proximal end 2711 and the distal end 2712. The proximal end 2711 of the shaft 2704 is attached to a base 2702, which can be coupled to a tool housing and/or instrument handle, for example. The distal end 2712 is attached to the articulation joint 2718. The end effector 2706 includes a proximal end 2714 that attaches to the articulation joint 2718. Four openings 2708a-d are spaced circumferentially along the side of the shaft 2704. The openings 2708a-d are shown in FIGS. 10-13. The openings 2708b and 2708d are more proximal on the shaft than openings 2708a and 2708c. The openings 2708a-d are spaced-equidistantly around the circumference of the shaft 2704, and the drive racks 2732a-d may be accessible through the openings 2708a-d in certain instances.

Figure 9:
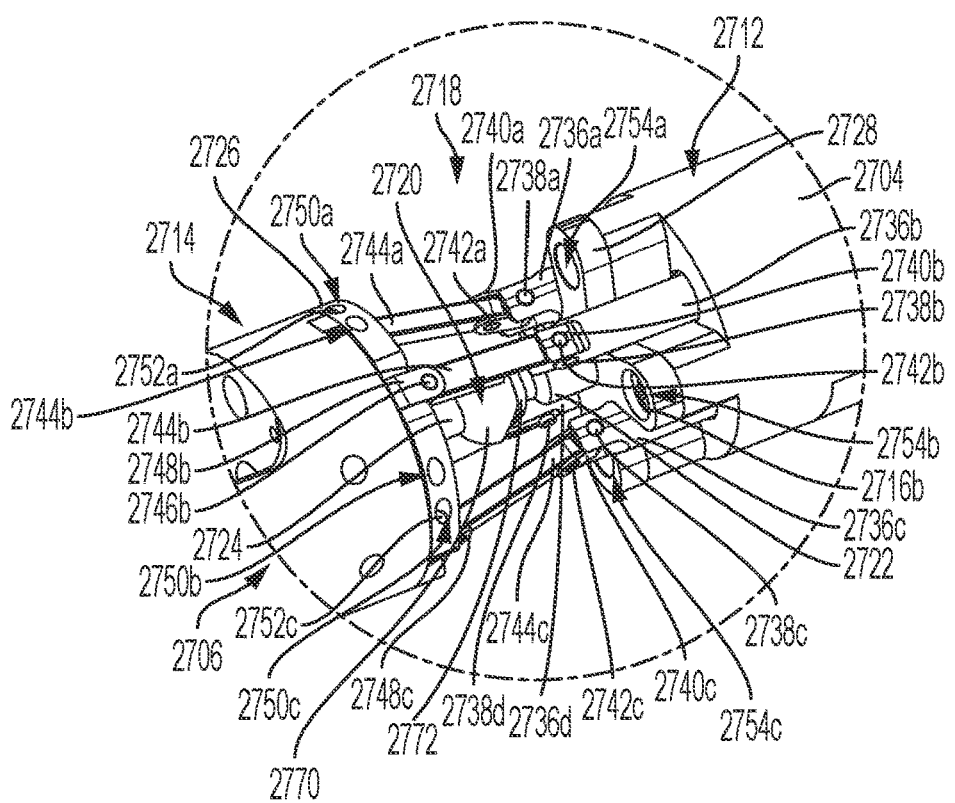
FIG. 9 is a detailed view of the articulation joint of the surgical tool of FIG. 8, in accordance with at least one aspect of the present disclosure.

FIG. 9 is a detailed view of the articulation joint 2718. The articulation system comprises five connections between the shaft and the end effector. The first connection includes a wrist joint 2720 positioned between a fixed member 2728 and a pivot member 2726. In some instances, the wrist joint 2720 can be a ball/spherical joint or a universal joint, which provides pivoting motion in a pitch plane and a yaw plane, as further described herein. In other instances, it can be a torque transfer joint, such as a constant velocity joint, for example.

Figure 10:
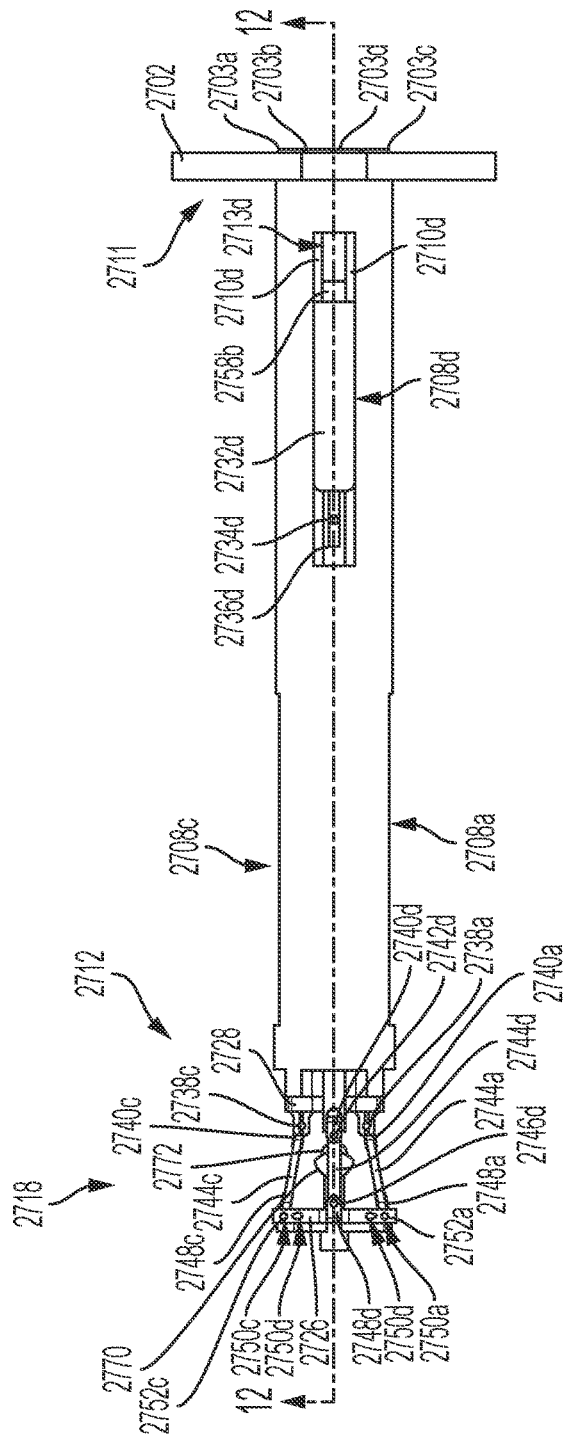
FIG. 10 is a bottom view of the surgical tool shown in FIG. 8 with the end effector removed, in accordance with at least one aspect of the present disclosure.
Figure 11:
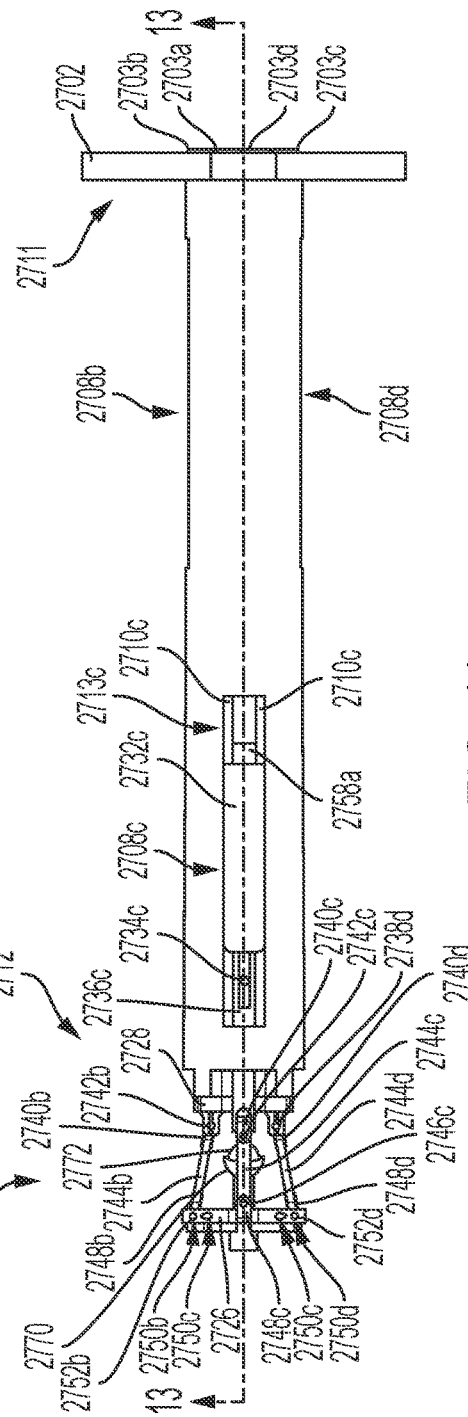
FIG. 11 is a side view of the surgical tool shown in FIG. 8 with the end effector removed, in accordance with at least one aspect of the present disclosure.

The second connection between the end effector 2706 and the shaft 2704 is the "a" series of mechanical links. The "a" series of links includes a rod 2736a, two coupling links 2740a, 2748a, and a mechanical link 2744a. A drive rack 2732a is coupled to a proximal end of the rod 2736a and selectively effects translation of the rod 2736a. The third connection between the end effector 2706 and the shaft 2704 is the "b" series of mechanical links. The "b" series of links includes a rod 2736b, two coupling links 2740b, 2748b, and a mechanical link 2744b. A drive rack 2732b is coupled to a proximal end of the rod 2736b and selectively effects translation of the rod 2736b. The fourth connection between the end effector 2706 and the shaft 2704 is the "c" series of mechanical links. The "c" series of links includes a rod 2736c, two coupling links 2740c, 2748c, and a mechanical link 2744c. A drive rack 2732c is coupled to a proximal end of the rod 2736c and selectively effects translation of the rod 2736c. The fifth connection between the end effector 2706 and the shaft 2704 is the "d" series of mechanical links. The "d" series of links includes a rod 2736d, two coupling links 2740d, 2748d, and a mechanical link 2744d. A drive rack 2732d is coupled to a proximal end of the rod 2736d and selectively effects translation of the rod 2736d. The rods 2736a-d and the drive racks 2732a-d are positioned within the shaft 2704 through the corresponding channels 2735a-d (FIGS. 10 and 11). The rods 2736a-d are equidistantly-positioned radially-outward from the center of the shaft 2704 and equidistantly-spaced apart within the shaft 2704.

Figure 13:
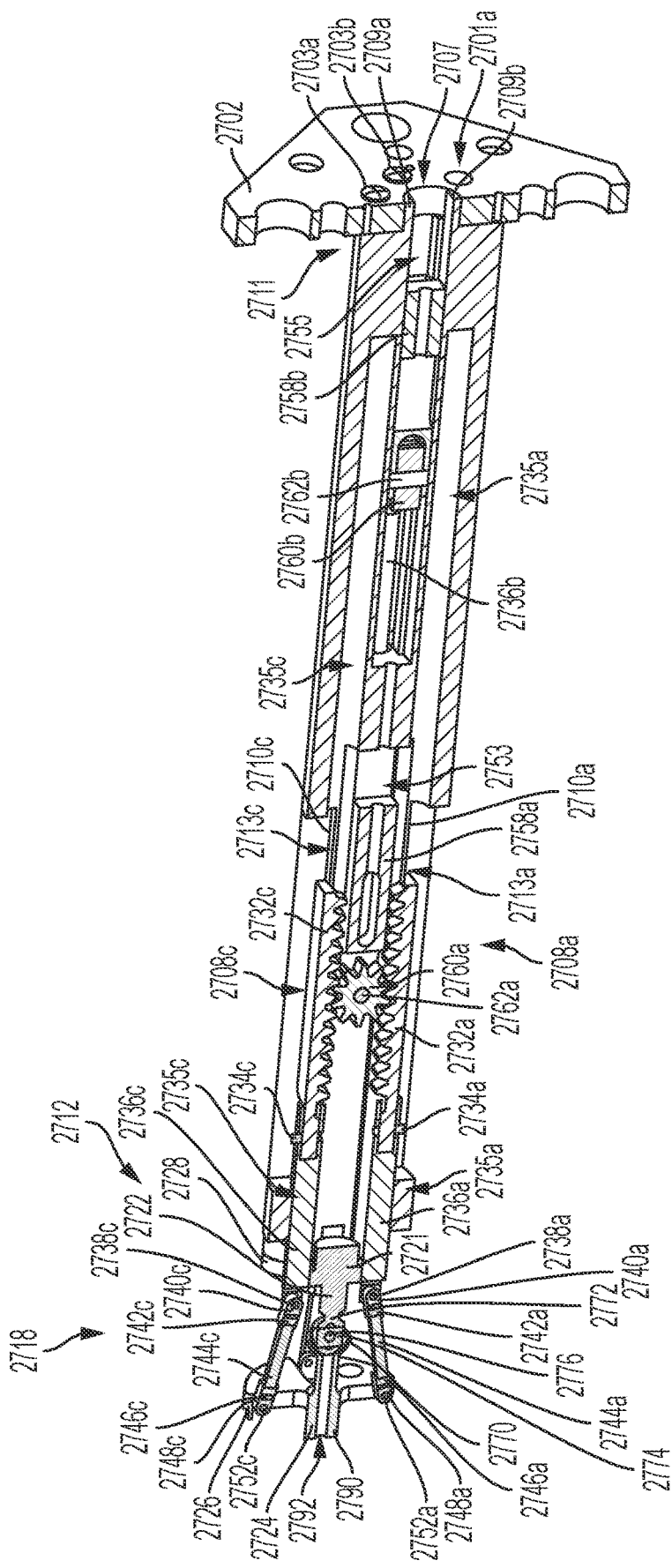
FIG. 13 is a cross-sectional view along the cross-section line indicated in FIG. 11, in accordance with at least one aspect of the present disclosure.
Figure 15:
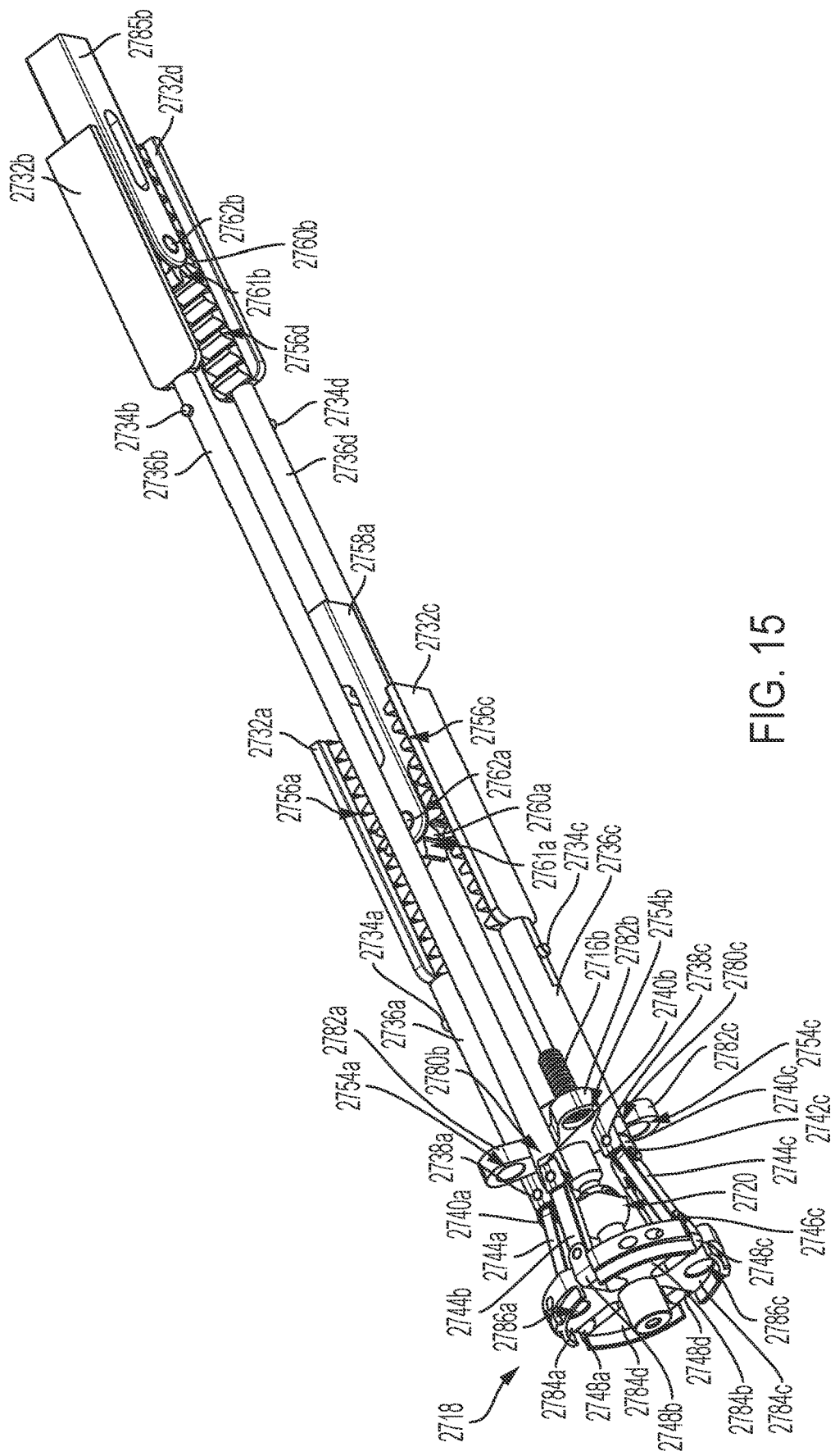
FIG. 15 is a perspective view of an articulation system for the surgical tool of FIG. 8 in an unarticulated position, in accordance with at least one aspect of the present disclosure.
Figure 16:
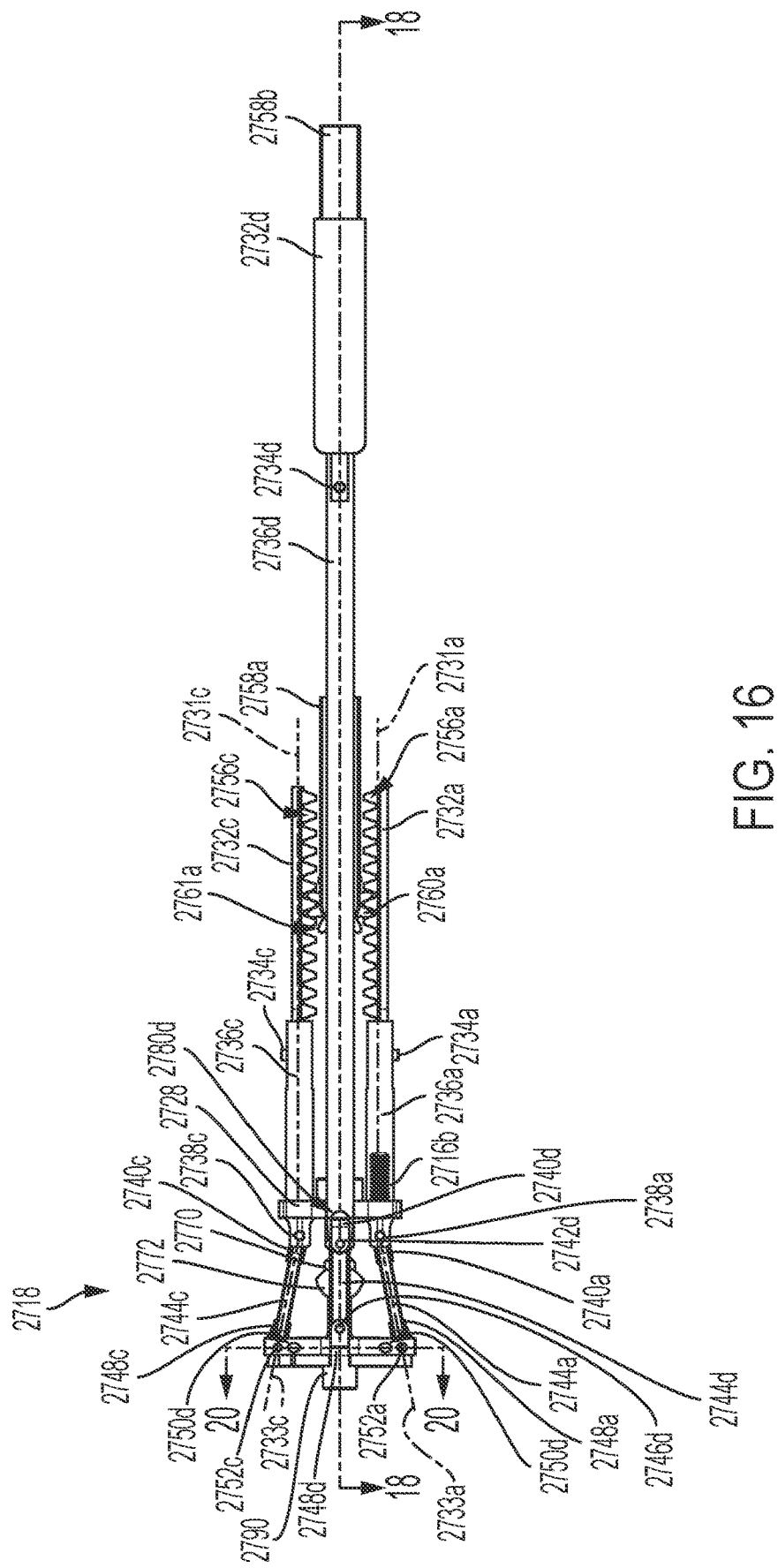
FIG. 16 is a top view of the articulation system shown in FIG. 13, in accordance with at least one aspect of the present disclosure.
Figure 17:
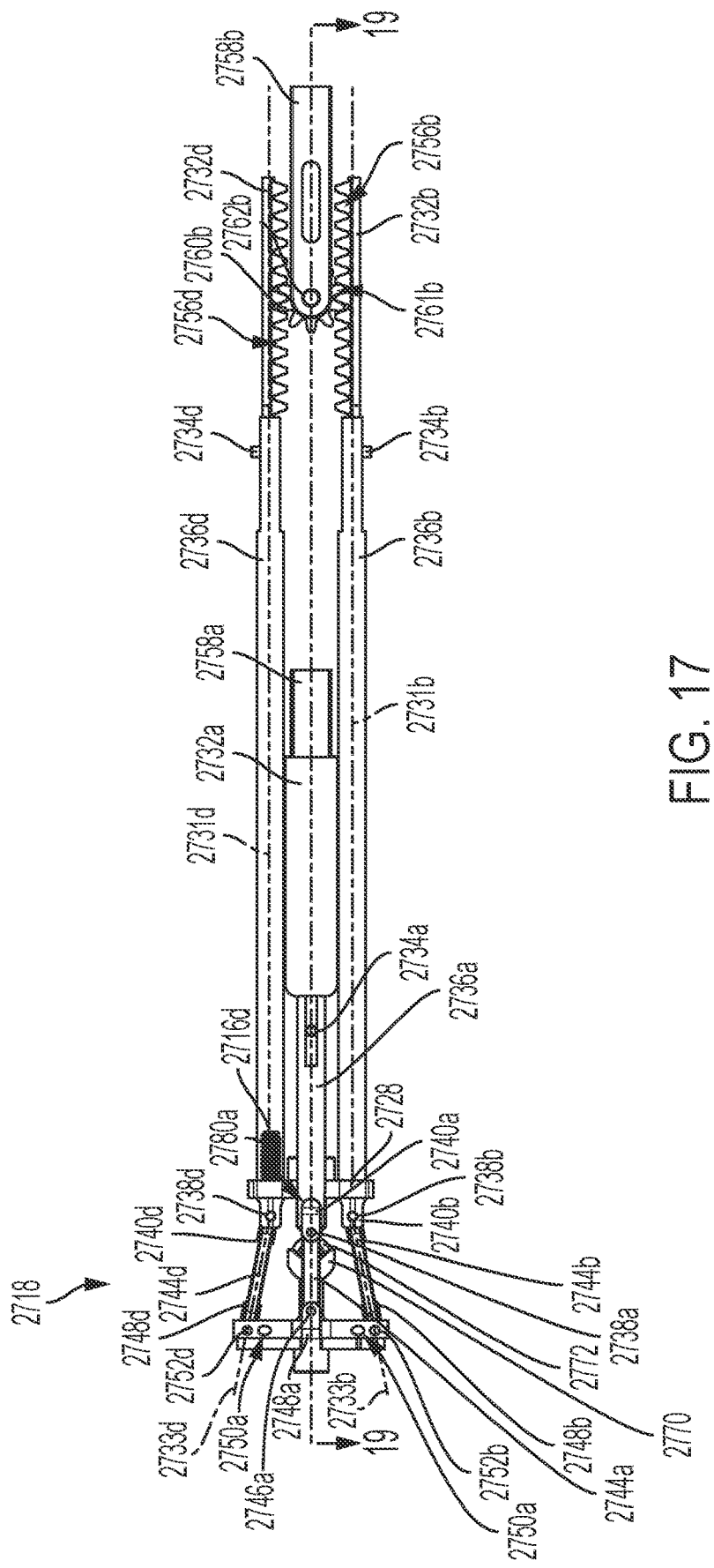
FIG. 17 is a side view of the articulation system shown in FIG. 13, in accordance with at least one aspect of the present disclosure.

Still referring to FIG. 9, the fixed member 2728 is attached to the distal end 2712 of the shaft 2704. The attachment could be made by any means that allows the fixed member 2728 to remain fixed against the distal end 2712 of the shaft 2704. In some instances, the fixed member 2728 can be bolted to the distal end 2712 of the shaft 2704 by bolts 2716b and 2716d (FIGS. 16 and 17). Referring primarily to FIG. 15, the fixed member 2728 can be shaped to comprise four lobes 2782a-d extending radially from the center of the fixed member 2728. Each of the lobes 2782a-d can include a corresponding hole 2754a-d. The holes 2754b, 2754d can be used to bolt the fixed member 2728 to the shaft 2704 with bolts 2716b, 2716d. In some instances, the bolts 2716b, 2716d can be placed in holes that are on opposite sides (e.g. catty-corner/diagonally-opposite) of the shaft 2704. The rods 2736a-d extend past the fixed member 2728 in the space between the lobes 2782a-d and move within the space when driving an articulation motion. Referring to FIG. 13, the fixed member 2728 can include a proximal extending portion 2721 that extends proximally into the shaft in channel 2753.

The proximal end of the end effector 2706 is attached to the pivot member 2726. The fixed member 2728 is attached to the distal end of the shaft 2704. The pivot member 2726 pivots relative to the fixed member 2728 as the end effector 2706 articulates relative to the shaft 2704. The wrist joint 2720 is positioned within the articulation joint 2718 between the fixed member 2728 and the pivot member 2726. The wrist joint 2720 includes a proximal portion 2772 and a distal portion 2770, where the distal portion 2770 rotates around the proximal portion 2772. Referring again to FIG. 9, the fixed member 2728 includes a distally-extending central shaft 2722 extending to the wrist joint 2720. The central shaft 2722 connects to the proximal portion 2772 of the wrist joint 2720. The pivot member 2726 includes a proximally-extending central shaft 2724 extending to the wrist joint 2720 and connecting to the distal portion 2770.

Figure 18:
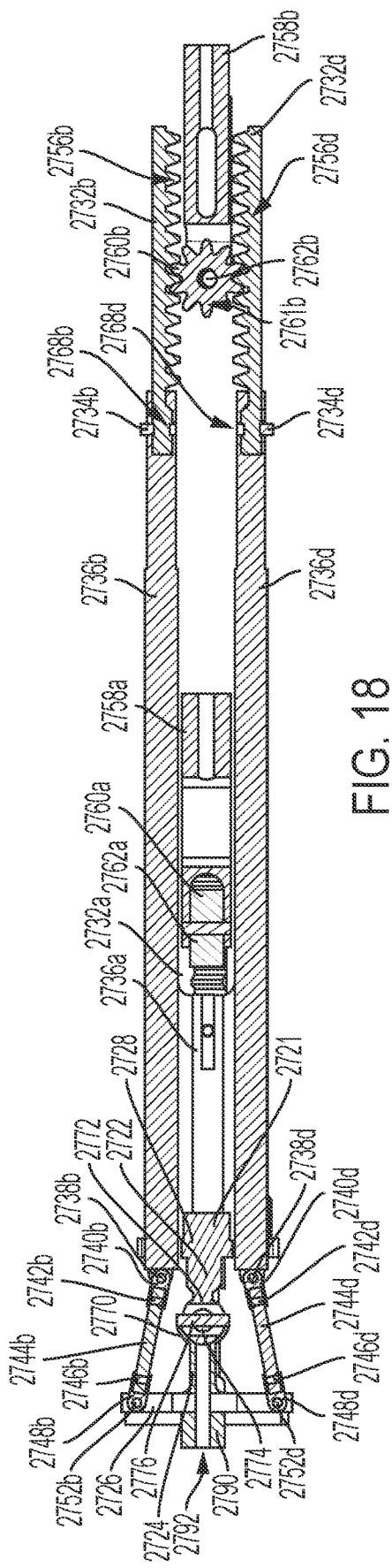
FIG. 18 is a cross-sectional view along the cross-section line indicated on FIG. 16, in accordance with at least one aspect of the present disclosure.
Figure 19:
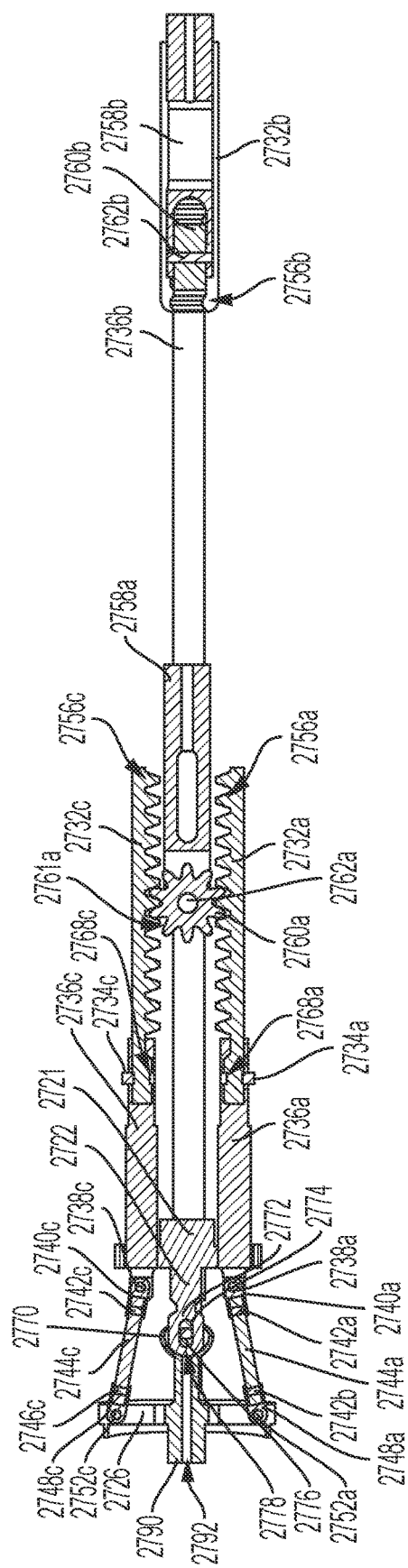
FIG. 19 is a cross-sectional view along the cross-section line indicated on FIG. 17, in accordance with at least one aspect of the present disclosure.

Referring now to FIGS. 18 and 19, the proximal portion 2772 is substantially spherical and hollow and has a pair of opposing flat external sides. A through-hole extends through the flat sides of the proximal portion 2772. The distal portion 2770 is a substantially cylindrical and is sized and configured to be inserted into the hollow, spherical portion of the proximal portion 2772. The distal portion 2770 is configured to pivot within the proximal portion 2772. Movement of the distal portion 2770 relative to the proximal portion 2772 can be constrained by a cross-member forming two pivot axes along a pin 2774 and a pin 2776, which are orthogonal. For example, the pin 2774 can extend into the through-hole between the flat external sides of the proximal portion 2772 and the pin 2776 can extend through a pinhole through the distal portion 2770. The pin 2776 extends through a through-slot 2778 in the proximal portion 2772. As the wrist joint 2720 rotates about the pin 2774, the pin 2776 moves in the through-slot 2778. The dual-pin connections allows the wrist joint 2720 to pivot about two axes that are transverse to each other.

Alternative wrist joints are also contemplated including one or more universal joints and/or one or more ball bearings combined with a torque transfer joint, such as a constant velocity joint. The arrangement of linkages and, more specifically, the arrangement of linkages maintaining a space within the articulation joint 2718 for housing a fifth connection can allow a torque coupling arrangement to be incorporated into the articulation joint. In such instances, the articulation joint can provide a robust articulation joint and means for transmitting torque through the shaft 2704 to the end effector 2706, such as the torque required to drive a firing member, lift staples, and cut tissue, for example. Moreover, in such instances, regardless of the orientation of the end effector 2706 relative to the shaft 2704 as the articulation joint 2718 is articulated, the distal portion of the torque transfer joint (e.g. a constant velocity joint) can remain in driving connection with the proximal portion.

Referring to FIGS. 10 and 11, the proximal end 2711 of the shaft 2704 is attached to the base 2702. In some instances, the shaft 2704 can be attached to the base 2702 by bolts 2703a-d (FIGS. 10-13). The base 2702 can be connected to the housing of the surgical tool 2700, which include house drive inputs (e.g. rotary inputs) that drive actuations of the surgical tool 2700. The base 2702 has multiple openings that can be used to connect the base 2702 to the housing. In other instances, the base 2702 can be a part of the housing. In other instances, the shaft 2704 can attach directly to the housing. Referring primarily to FIG. 13, the shaft 2704 also includes connectors, or protrusions, 2709a, 2709b that extend into a central through-hole 2707 in the base 2702.

In various instances, the surgical tool 2700 can define longitudinal access channels from the base 2702, through the shaft 2704, through the articulation joint 2718, and into the end effector 2706. The access channels can provide a pathway for actuators, cables, wires, and/or conductors for extending between the tool housing and the end effector 2706. For example, the base 2702 includes a through-hole 2701a (FIG. 13) and another through-hole 2701c (FIG. 12), which are aligned with access channels or open space(s) in the shaft 2704. The through-hole 2701c in the base 2702 is aligned with a hole 2754c in the fixed member 2728 such that an access channel extends from the base 2702 to the fixed member 2728 along a longitudinal axis 2785c (FIG. 21). The through-hole 2701a is aligned with a hole 2754a in the fixed member 2728 such that another access channel extends from the base 2702 to the fixed member 2728 along the longitudinal axis 2785a (FIG. 21). In certain instances, the first access channel can provide an electrically-isolated pathway for providing current to the end effector, and the second access channel can provide an electrically-isolated pathway for returning current to the housing, for example.

Figure 14:
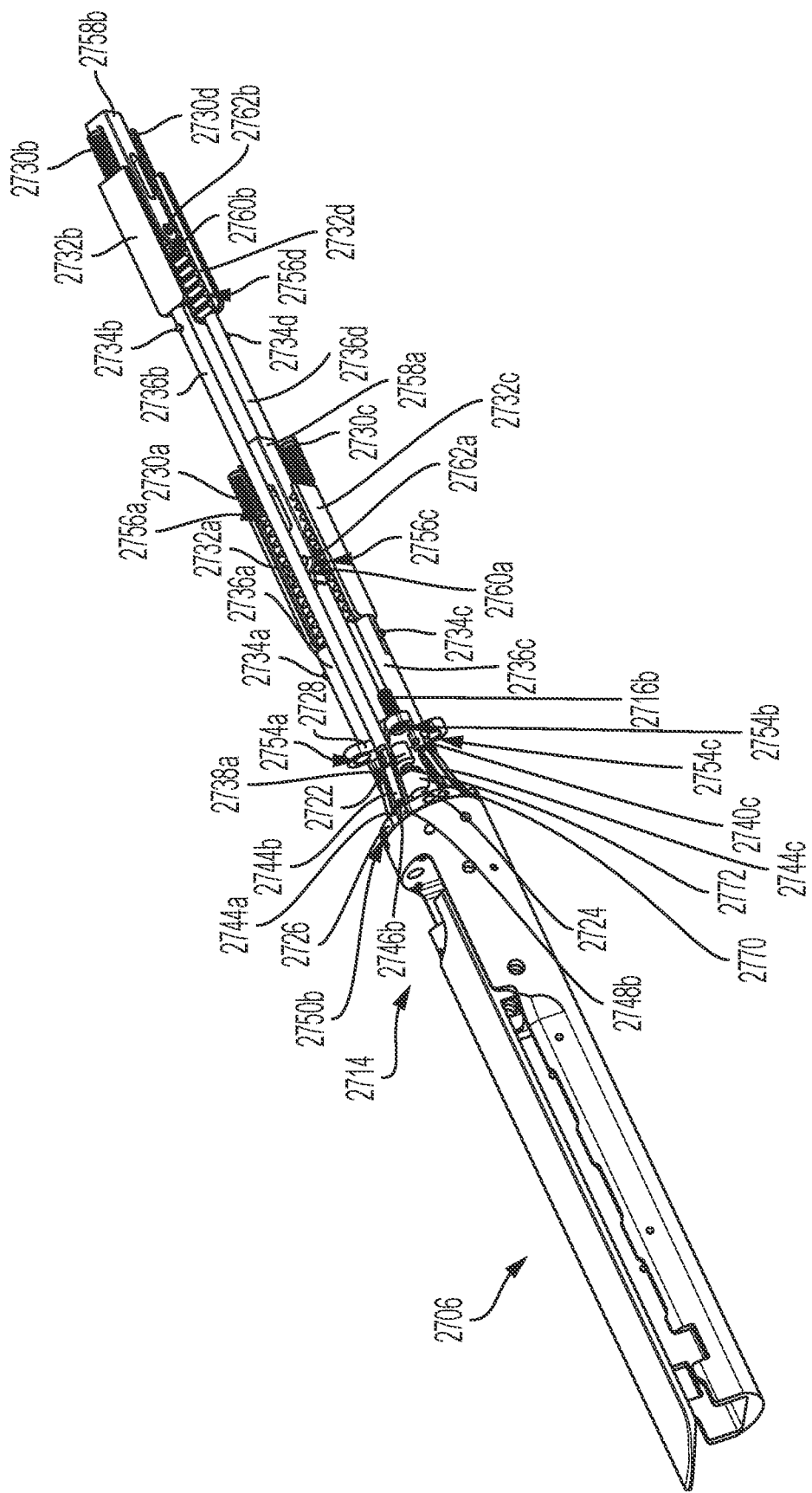
FIG. 14 is a perspective view of the surgical tool shown in FIG. 8 with some components removed, in accordance with at least one aspect of the present disclosure.

Referring primarily to FIG. 14, the drive system includes four series of links as described above (i.e. the "a", "b", "c", and "d" series of links). Each series of links can be coupled to the shaft 2704 by a spring. In other instances, each paired series of links can be coupled to the shaft 2704 by a spring (e.g. the carriers 2758a, 2758b can be motivated in a particular position by one or more springs). The four series of links are equally spaced circumferentially around the shaft 2704. The four series of links work together with pushing and pulling forces that drive the articulation joint to articulate the end effector. Each series of links is substantially similar and is configured to exert complementary forces to articulate the end effector 2706 relative to the shaft 2704 and, more specifically, to articulate the pivot member 2726 relative to the fixed member 2728.

Referring now to FIGS. 14 and 15, the "a" series of links includes a spring 2730a attached to a proximal end of the drive rack 2732a. The spring 2730a is also coupled to the shaft 2704. In various instances, the spring 2730a can be configured to bias the drive rack 2732a into a particular position relative to the shaft 2704 that corresponds to a particular orientation of the articulation joint 2718. For example, the spring 2730a can bias the articulation joint 2718 into an unarticulated, or straight/linear, configuration in certain instances.

The distal end of the drive rack 2732a is attached to the rod 2736a. In some instances, the distal end of the drive rack 2732a is inserted into/embedded in the proximal end of the rod 2736a or vice versa. Referring now to FIG. 19, in certain instances, the attachment can be made by a pin 2734a that extends through the rod 2736a and into a groove 2768a in the distal end of the drive rack 2732a. In such instances, the drive rack 2732a is fixed to the rod 2736a and displacement of the drive rack 2732a in a proximal or distal direction results in a corresponding displacement of the rod 2736a. The rod 2736a extends distally within the shaft 2704 in the channel 2735a (FIG. 13) and through the distal end 2712 of the shaft 2704 into driving engagement with the articulation joint 2718.

Referring primarily to FIG. 19, the distal end of the rod 2736a is pivotably coupled to the proximal end of the coupling link 2740a. For example, a pivot coupling can be made by a pin 2738a, which extends through aligned through-holes in a proximal end of the coupling link 2740a and a distal end of the rod 2736a. In some instances, a channel 2780a (FIG. 17) is defined into the distal end of the rod 2736a and the coupling link 2740a, or at least a proximal portion thereof, can be inserted into the channel 2780a (FIG. 17) and then pivotably coupled to the rod 2736a. The channel 2780a (FIG. 17) can be sufficiently deep to allow the coupling link 2740a to rotate about the pin 2738a after it is pivotably coupled to the rod 2736a.

The distal end of the coupling link 2740a is pivotably coupled to the proximal end of the mechanical link 2744a. For example, a pivot coupling can be made by a pin 2742a, which extends through aligned through-holes in a proximal end of the mechanical link 2744a and a distal end of the coupling link 2740a. The mechanical link 2744a is configured to rotate relative to the coupling link 2740a about the pin 2742a. In the depicted articulation joint 2718, the pins 2738a and 2742a are oriented in orthogonal directions and the coupling link 2740a rotates relative to the rod 2736a about a first axis (defined by the pin 2738a), and the mechanical link 2744a rotates relative to the coupling link 2740a about a second axis (defined by the pin 2742a) that is transverse to the first axis. In such instances, the coupling link 2740a provides two degrees of freedom for the mechanical link 2744a.

Referring still to FIG. 19, the distal end of the mechanical link 2744a is pivotably coupled to a proximal end of a coupling link 2748a. For example, a pivot coupling can be made by a pin 2746a, which extends through aligned through-holes in the distal end of the mechanical link 2744a and the proximal end of the coupling link 2748a. The coupling link 2748a is configured to rotate relative to the mechanical link 2744a about the pin 2746a.

Figure 20:
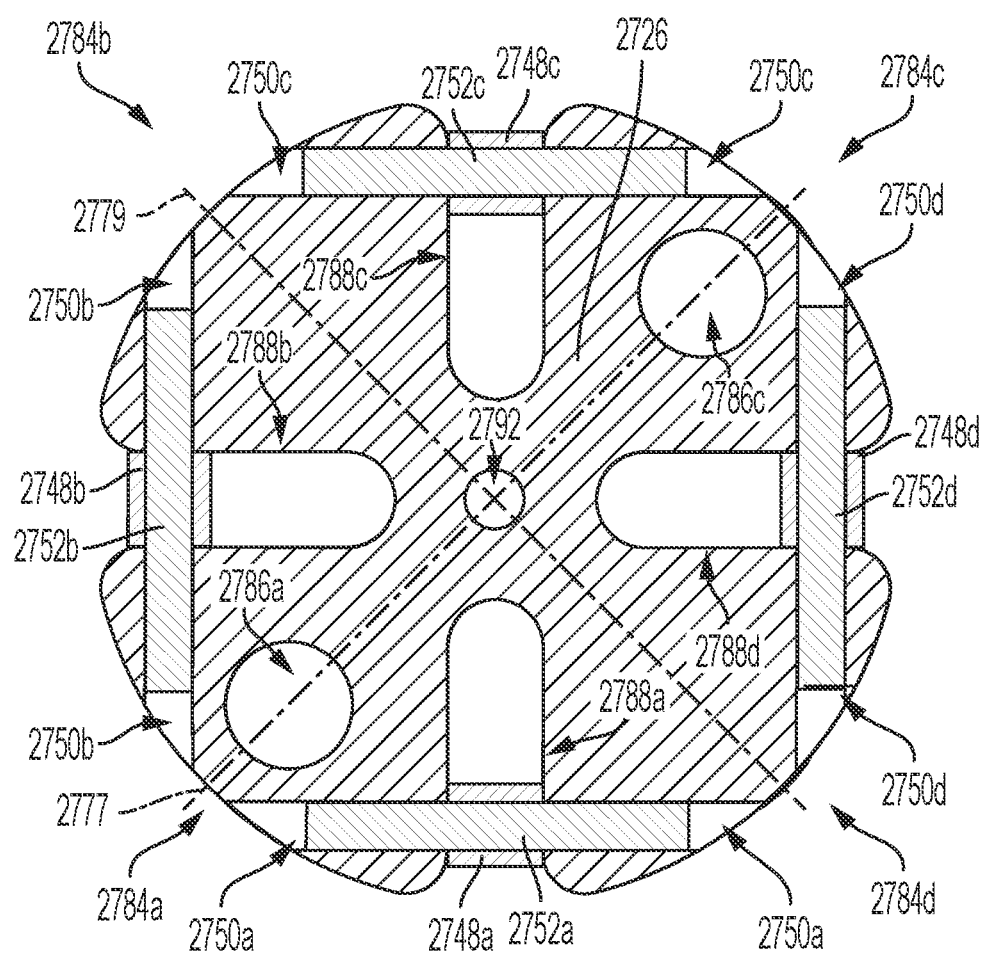
FIG. 20 is a cross-sectional view along the cross-section line indicated on FIG. 16, in accordance with at least one aspect of the present disclosure.
Figure 21:
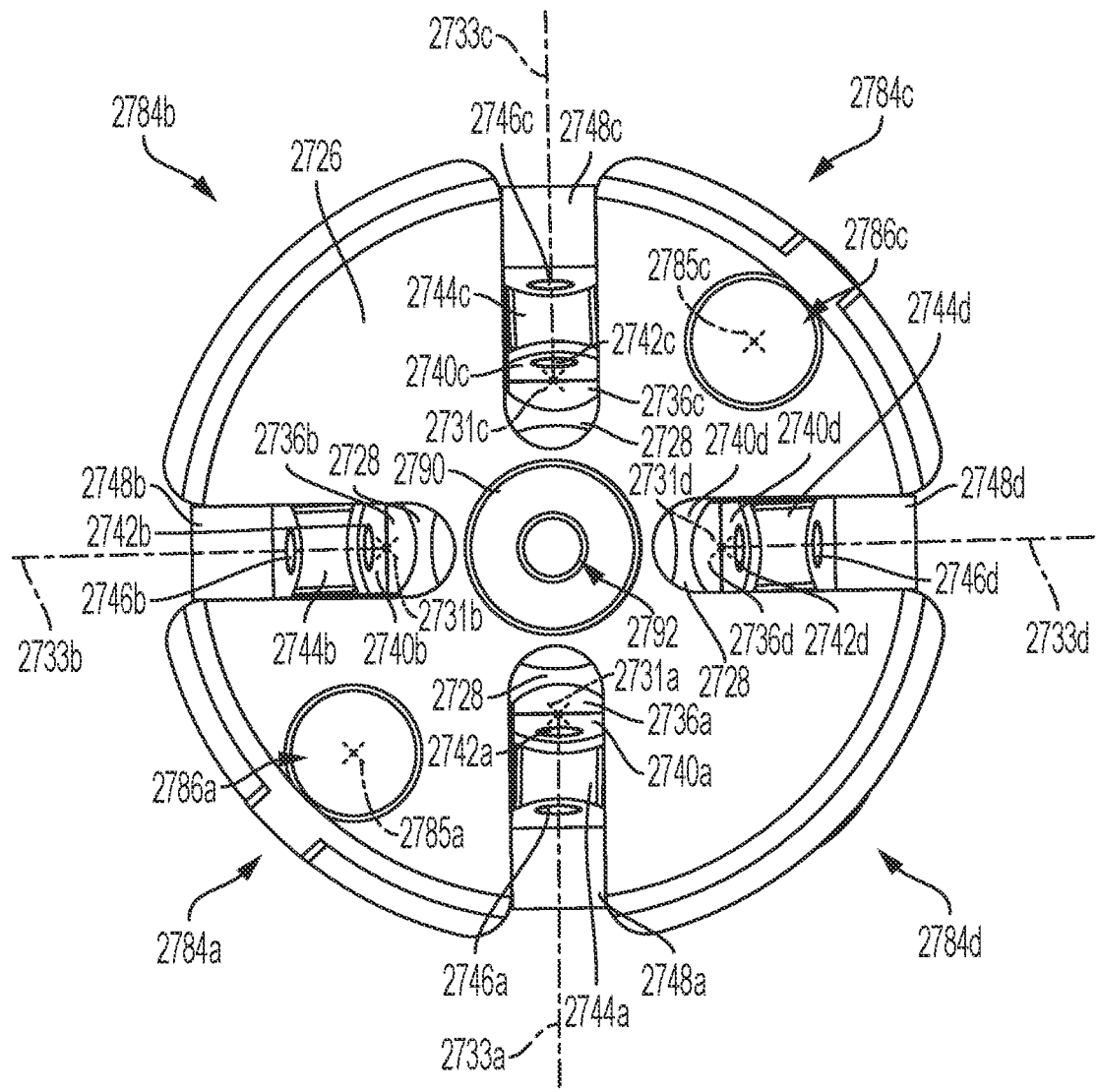
FIG. 21 is a front view of the articulation system shown in FIG. 13, in accordance with at least one aspect of the present disclosure.

Referring primarily to FIGS. 20 and 21, the coupling link 2748a is pivotably coupled to the pivot member 2726. For example, the distal end of the coupling link 2748a can be positioned in the space between adjacent lobes 2784a and 2784d so that a through-hole 2750a (FIG. 21) in the pivot member 2726 is aligned with a through-hole in the coupling link 2748a and a pin 2752a extends therethrough to pivotably couple the coupling link 2748a to the pivot member 2726. The coupling link 2748a is configured to rotate about an axis defined by the pin 2752a.

In the depicted articulation joint 2718, the pins 2746a and 2752a are oriented in orthogonal directions and the coupling link 2748a rotates relative to the mechanical link 2744a about a third axis (defined by the pin 2746a), and the pivot member 2726 rotates relative to the coupling link 2748a about a fourth axis (defined by the pin 2752a) that is transverse to the third axis. In such instances, the coupling link 2748a provides two degrees of freedom for the pivot plate 2726. Pivotal displacement of the "a" series of links is further constrained by the other mechanical links between the fixed member 2728 and the pivot member 2726 further described herein.

Referring now to FIGS. 14 and 15, the "b" series of links includes a spring 2730b attached to a proximal end of the drive rack 2732b. The spring 2730b is also coupled to the shaft 2704. In various instances, the spring 2730*b* can be configured to bias the drive rack 2732*b* into a particular position relative to the shaft 2704 that corresponds to a particular orientation of the articulation joint 2718. For example, the spring 2730*b* can bias the articulation joint 2718 into an unarticulated, or straight/linear, configuration in certain instances.

The distal end of the drive rack 2732*b* is attached to the rod 2736*b*. In some instances, the distal end of the drive rack 2732*b* is inserted into/embedded in the proximal end of the rod 2736*b* or vice versa. Referring now to FIG. 18, in certain instances, the attachment can be made by a pin 2734*b* that extends through the rod 2736*b* and into a groove 2768*b* in the distal end of the drive rack 2732*b*. In such instances, the drive rack 2732*b* is fixed to the rod 2736*b* and displacement of the drive rack 2732*b* in a proximal or distal direction results in a corresponding displacement of the rod 2736*b*. The rod 2736*b* extends distally within the shaft 2704 in the channel 2735*b* (FIG. 12) and through the distal end 2712 of the shaft 2704 into driving engagement with the articulation joint 2718.

Referring primarily to FIG. 18, the distal end of the rod 2736*b* is pivotably coupled to the proximal end of the coupling link 2740*b*. For example, a pivot coupling can be made by a pin 2738*b*, which extends through aligned through-holes in a proximal end of the coupling link 2740*b* and a distal end of the rod 2736*b*. In some instances, a channel 2780*b* (FIG. 15) is defined into the distal end of the rod 2736*b* and the coupling link 2740*b*, or at least a proximal portion thereof, can be inserted into the channel 2780*b* (FIG. 15) and then pivotably coupled to the rod 2736*b*. The channel 2780*b* (FIG. 15) can be sufficiently deep to allow the coupling link 2740*b* to rotate about the pin 2738*b* after it is pivotably coupled to the rod 2736*b*.

The distal end of the coupling link 2740*b* is pivotably coupled to the proximal end of the mechanical link 2744*b*. For example, a pivot coupling can be made by a pin 2742*b*, which extends through aligned through-holes in a proximal end of the mechanical link 2744*b* and a distal end of the coupling link 2740*b*. The mechanical link 2744*b* is configured to rotate relative to the coupling link 2740*b* about the pin 2742*b*. In the depicted articulation joint 2718, the pins 2738*b* and 2742*b* are oriented in orthogonal directions and the coupling link 2740*b* rotates relative to the rod 2736*b* about a first axis (defined by the pin 2738*b*), and the mechanical link 2744*b* rotates relative to the coupling link 2740*b* about a second axis (defined by the pin 2742*b*) that is transverse to the first axis. In such instances, the coupling link 2740*b* provides two degrees of freedom for the mechanical link 2744*b*.

Referring still to FIG. 18, the distal end of the mechanical link 2744*b* is pivotably coupled to a proximal end of a coupling link 2748*b*. For example, a pivot coupling can be made by a pin 2746*b*, which extends through aligned through-holes in the distal end of the mechanical link 2744*b* and the proximal end of the coupling link 2748*b*. The coupling link 2748*b* is configured to rotate relative to the mechanical link 2744*b* about the pin 2746*b*.

Referring primarily to FIGS. 20 and 21, the coupling link 2748*b* is pivotably coupled to the pivot member 2726. For example, the distal end of the coupling link 2748*b* can be positioned in the space between adjacent lobes 2784*a* and 2784*b* so that a through-hole 2750*b* in the pivot member 2726 is aligned with a through-hole in the coupling link 2748*b* and a pin 2752*b* extends therethrough to pivotably couple the coupling link 2748*b* to the pivot member 2726. The coupling link 2748*b* is configured to rotate about an axis defined by the pin 2752*b*.

In the depicted articulation joint 2718, the pins 2746*b* and 2752*b* are oriented in orthogonal directions and the coupling link 2748*b* rotates relative to the mechanical link 2744*b* about a third axis (defined by the pin 2746*b*), and pivot member 2726 rotates relative to the coupling link 2748*b* about a fourth axis (defined by the pin 2752*b*) that is transverse to the first and third. In such instances, the coupling link 2748*b* provides two degrees of freedom for the pivot plate 2726. Pivotal displacement of the "b" series of links is further constrained by the other mechanical links between the fixed member 2728 and the pivot member 2726 further described herein.

Referring now to FIGS. 14 and 15, the "c" series of links includes a spring 2730*c* attached to a proximal end of the drive rack 2732*c*. The spring 2730*c* is also coupled to the shaft 2704. In various instances, the spring 2730*c* can be configured to bias the drive rack 2732*c* into a particular position relative to the shaft 2704 that corresponds to a particular orientation of the articulation joint 2718. For example, the spring 2730*c* can bias the articulation joint 2718 into an unarticulated, or straight/linear, configuration in certain instances.

The distal end of the drive rack 2732*c* is attached to the rod 2736*c*. In some instances, the distal end of the drive rack 2732*c* is inserted into/embedded in the proximal end of the rod 2736*c* or vice versa. Referring now to FIG. 19, in certain instances, the attachment can be made by a pin 2734*c* that extends through the rod 2736*c* and into a groove 2768*c* in the distal end of the drive rack 2732*c*. In such instances, the drive rack 2732*c* is fixed to the rod 2736*c* and displacement of the drive rack 2732*c* in a proximal or distal direction results in a corresponding displacement of the rod 2736*c*. The rod 2736*c* extends distally within the shaft 2704 in the channel 2735*c* (FIG. 13) and through the distal end 2712 of the shaft 2704 into driving engagement with the articulation joint 2718.

Referring primarily to FIG. 19, the distal end of the rod 2736*c* is pivotably coupled to the proximal end of the coupling link 2740*c*. For example, a pivot coupling can be made by a pin 2738*c*, which extends through aligned through-holes in a proximal end of the coupling link 2740*c* and a distal end of the rod 2736*c*. In some instances, a channel 2780*c* (FIG. 15) is defined into the distal end of the rod 2736*c* and the coupling link 2740*c*, or at least a proximal portion thereof, can be inserted into the channel 2780*c* (FIG. 15) and then pivotably coupled to the rod 2736*c*. The channel 2780*c* (FIG. 15) can be sufficiently deep to allow the coupling link 2740*c* to rotate about the pin 2738*c* after it is pivotably coupled to the rod 2736*c*.

The distal end of the coupling link 2740*c* is pivotably coupled to the proximal end of the mechanical link 2744*c*. For example, a pivot coupling can be made by a pin 2742*c*, which extends through aligned through-holes in a proximal end of the mechanical link 2744*c* and a distal end of the coupling link 2740*c*. The mechanical link 2744*c* is configured to rotate relative to the coupling link 2740*c* about the pin 2742*c*. In the depicted articulation joint 2718, the pins 2738*c* and 2742*c* are oriented in orthogonal directions and the coupling link 2740*c* rotates relative to the rod 2736*c* about a first axis (defined by the pin 2738*c*), and the mechanical link 2744*c* rotates relative to the coupling link 2740*c* about a second axis (defined by the pin 2742*c*) that is transverse to the first axis. In such instances, the coupling link 2740c provides two degrees of freedom for the mechanical link 2744c.

Referring still to FIG. 19, the distal end of the mechanical link 2744c is pivotably coupled to a proximal end of a coupling link 2748c. For example, a pivot coupling can be made by a pin 2746c, which extends through aligned through-holes in the distal end of the mechanical link 2744c and the proximal end of the coupling link 2748c. The coupling link 2748c is configured to rotate relative to the mechanical link 2744c about the pin 2746c.

Referring primarily to FIGS. 20 and 21, the coupling link 2748c is pivotably coupled to the pivot member 2726. For example, the distal end of the coupling link 2748c can be positioned in the space between adjacent lobes 2784b and 2784c so that a through-hole 2750c (FIG. 21) in the pivot member 2726 is aligned with a through-hole in the coupling link 2748c and a pin 2752c extends therethrough to pivotably couple the coupling link 2748c to the pivot member 2726. The coupling link 2748c is configured to rotate about an axis defined by the pin 2752c.

In the depicted articulation joint 2718, the pins 2746c and 2752c are oriented in orthogonal directions and the coupling link 2748c rotates relative to the mechanical link 2744c about a third axis (defined by the pin 2746c), and pivot member 2726 rotates relative to the coupling link 2748c about a fourth axis (defined by the pin 2752c) that is transverse to the first and third. In such instances, the coupling link 2748c provides two degrees of freedom for the pivot plate 2726. Pivotal displacement of the "c" series of links is further constrained by the other mechanical links between the fixed member 2728 and the pivot member 2726 further described herein.

Referring now to FIGS. 14 and 15, the "d" series of links includes a spring 2730d attached to a proximal end of the drive rack 2732d. The spring 2730d is also coupled to the shaft 2704. In various instances, the spring 2730d can be configured to bias the drive rack 2732d into a particular position relative to the shaft 2704 that corresponds to a particular orientation of the articulation joint 2718. For example, the spring 2730d can bias the articulation joint 2718 into an unarticulated, or straight/linear, configuration in certain instances.

The distal end of the drive rack 2732d is attached to the rod 2736d. In some instances, the distal end of the drive rack 2732d is inserted into/embedded in the proximal end of the rod 2736d or vice versa. Referring now to FIG. 18, in certain instances, the attachment can be made by a pin 2734d that extends through the rod 2736d and into a groove 2768d in the distal end of the drive rack 2732d. In such instances, the drive rack 2732d is fixed to the rod 2736d and displacement of the drive rack 2732d in a proximal or distal direction results in a corresponding displacement of the rod 2736d. The rod 2736d extends distally within the shaft 2704 in the channel 2735d (FIG. 12) and through the distal end 2712 of the shaft 2704 into driving engagement with the articulation joint 2718.

Referring primarily to FIG. 18, the distal end of the rod 2736d is pivotably coupled to the proximal end of the coupling link 2740d. For example, a pivot coupling can be made by a pin 2738d, which extends through aligned through-holes in a proximal end of the coupling link 2740d and a distal end of the rod 2736d. In some instances, a channel 2780d (FIG. 16) is defined into the distal end of the rod 2736d and the coupling link 2740d, or at least a proximal portion thereof, can be inserted into the channel 2780d (FIG. 16) and then pivotably coupled to the rod 2736d. The channel 2780d (FIG. 16) can be sufficiently deep to allow the coupling link 2740d to rotate about the pin 2738d after it is pivotably coupled to the rod 2736d.

The distal end of the coupling link 2740d is pivotably coupled to the proximal end of the mechanical link 2744d. For example, a pivot coupling can be made by a pin 2742d, which extends through aligned through-holes in a proximal end of the mechanical link 2744d and a distal end of the coupling link 2740d. The mechanical link 2744d is configured to rotate relative to the coupling link 2740d about the pin 2742d. In the depicted articulation joint 2718, the pins 2738d and 2742d are oriented in orthogonal directions and the coupling link 2740d rotates relative to the rod 2736d about a first axis (defined by the pin 2738d), and the mechanical link 2744d rotates relative to the coupling link 2740d about a second axis (defined by the pin 2742d) that is transverse to the first axis. In such instances, the coupling link 2740d provides two degrees of freedom for the mechanical link 2744d.

Referring still to FIG. 18, the distal end of the mechanical link 2744d is pivotably coupled to a proximal end of a coupling link 2748d. For example, a pivot coupling can be made by a pin 2746d, which extends through aligned through-holes in the distal end of the mechanical link 2744d and the proximal end of the coupling link 2748d. The coupling link 2748d is configured to rotate relative to the mechanical link 2744d about the pin 2746b.

Referring primarily to FIGS. 20 and 21, the coupling link 2748d is pivotably coupled to the pivot member 2726. For example, the distal end of the coupling link 2748d can be positioned in the space between adjacent lobes 2784c and 2784d so that a through-hole 2750d in the pivot member 2726 is aligned with a through-hole in the coupling link 2748d and a pin 2752d extends therethrough to pivotably couple the coupling link 2748d to the pivot member 2726. The coupling link 2748d is configured to rotate about an axis defined by the pin 2752d.

In the depicted articulation joint 2718, the pins 2746d and 2752d are oriented in orthogonal directions and the coupling link 2748d rotates relative to the mechanical link 2744d about a third axis (defined by the pin 2746d), and pivot member 2726 rotates relative to the coupling link 2748d about a fourth axis (defined by the pin 2752d) that is transverse to the first and third. In such instances, the coupling link 2748d provides two degrees of freedom for the pivot plate 2726. Pivotal displacement of the "d" series of links is further constrained by the other mechanical links between the fixed member 2728 and the pivot member 2726 further described herein.

Referring primarily to FIGS. 16 and 17, the mechanical links 2744a-d are angled radially outward in a distal direction, i.e. the mechanical links 2744a-d extend distally away from a longitudinal centerline of the shaft 2704 along one of axes 2733a-d. For example, the mechanical link 2744a extends along axis 2733a, the mechanical link 2744b extends along axis 2733b, the mechanical link 2744c extends along axis 2733c, and the mechanical link 2744d extends along axis 2733d. Stated another way, the mechanical links 2744a-d are respectively coupled to the distal ends of rods 2736a-d at a first radial distance from the center of the shaft 2704 and the mechanical links 2744a-d are coupled to the pivot member 2726 at a second radial distance from center of the shaft 2704, and the second radial distance is greater than the first radial distance.

Referring primarily to FIG. 21, the pivot member 2726 includes four lobes 2784a-d that extend radially outward from the center of the pivot member 2726. The lobes 2784*a-d* are symmetrically arranged about a central opening 2792 through the pivot member 2726. More specifically, the pivot member 2726 is radially symmetric with the exception of the through-holes 2786*a*, 2786*c* through two of the four lobes 2784*a-d*. The pivot member 2726 is symmetric about a diagonal centerline 2777 through the lobes 2784*a* and 2784*c* and also symmetric about a second diagonal centerline 2779 through the lobes 2784*b* and 2784*d*. The lobes 2784*a-d* and the channels 2788*a-d* between adjacent lobes 2784*a-d* form a flower-like shape around the central opening 2792.

The lobe 2784*a* extends radially between the adjacent coupling links 2748*a*, 2748*d*; the lobe 2784*b* extends radially between the adjacent coupling links 2748*a*, 2748*b*; the lobe 2784*c* extends radially between the adjacent coupling links 2748*b*, 2748*c*; and the lobe 2784*d* extends radially between the adjacent coupling links 2748*c*, 2748*d*. In the unarticulated position, the "a", "b", "c", and "d" series of links are aligned with the space between the lobes 2784*a-d* where the coupling links 2748*a-d* are pivotably attached. More specifically, each rod 2736*a-d* extends along a longitudinal axis 2731*a-d* (see FIGS. 16 and 17), respectively, along which the rods 2736*a* are configured to translate. When in the unarticulated configuration, the longitudinal axes 2731*a-d* are symmetrically aligned within the spaces between the adjacent lobes 2784*a-d*. When the articulation system is actuated and moved toward an articulation configuration, the pivot member 2726 is pivoted or twisted relative to the fixed plate 2728 and the longitudinal axes 2731*a-d* may move out of alignment with the spaces between the adjacent lobes 2784*a-d*.

The pivot member 2726 also includes through-holes 2786*a* and 2786*c*. The through-hole 2786*a* is aligned with the through-hole 2754*a* in the fixed member 2728 when the articulation joint 2718 is in an unarticulated configuration. As described above, the through-hole 2754*a* in the fixed member 2728 is aligned with an access channel that goes through the entire shaft 2704 and base 2702 along longitudinal axis 2785*a* (FIG. 21). Thus, the through-hole 2786*a* provides an access pathway that goes from the base 2702 and into the end effector 2706. The through-hole 2786*c* is aligned with the through-hole 2754*c* in the fixed member 2728 when the articulation joint 2718 is in an unarticulated configuration. As described above, the through-hole 2754*c* in the fixed member 2728 is aligned with an access channel that goes through the entire shaft 2704 and base 2702 along longitudinal axis 2785*c* (FIG. 21). Thus, the through-hole 2786*a* provides a second access pathway that goes from the base 2702 and into the end effector 2706.

In various instances, the pivot member 2726 can also include a distally-extending portion 2790 that extends distally from the center of the pivot member 2726. In some instances, the distally-extending portion 2790 can have a central through-hole 1792. In certain instances, the distally-extending portion 2790 can be used to align and connect the pivot member 2726 with the end effector 2706 in certain instances.

Referring primarily now to FIG. 20, the space between the lobes 2784*a-d* of pivot member 2726 can be considered channels 2788*a-d*. In these channels 2788*a-d*, the coupling links 2748*a-d* are pivotably attached. For example, coupling link 2748*a* is pivotably coupled to pivot member 2726 in the channel 2788*a*. A through-hole 2750*a* extends between the lobe 2784*a* and the lobe 2784*d*, and the coupling link 2748*a* is positioned so that a through-hole in the coupling link 2748*a* is aligned with the through-hole 2750*a*. A pin 2752*a* extends through the through-hole 2750*a* to pivotably couple the coupling link 2748*a* to the pivot member 2726 in the channel 2788*a*. In various instances, the coupling link 2748*b* is pivotably coupled to the pivot member 2726 in the channel 2788*b*. A through-hole 2750*b* extends between the lobe 2784*a* and the lobe 2784*b*, and the coupling link 2748*b* is positioned so that a through-hole in the coupling link 2748*b* is aligned with the through-hole 2750*b*. A pin 2752*b* extends through the through-hole 2750*b* to pivotably couple the coupling link 2748*b* to the pivot member 2726 in the channel 2788*b*. In various instances, the coupling link 2748*c* is pivotably coupled to the pivot member 2726 in the channel 2788*c*. A through-hole 2750*c* extends between the lobe 2784*b* and the lobe 2784*c*, and the coupling link 2748*c* is positioned so that a through-hole in the coupling link 2748*c* is aligned with the through-hole 2750*c*. A pin 2752*c* extends through the through-hole 2750*c* to pivotably couple the coupling link 2748*c* to the pivot member 2726 in the channel 2788*c*. In various instances, the coupling link 2748*d* is pivotably coupled to the pivot member 2726 in the channel 2788*d*. A through-hole 2750*d* extends between the lobe 2784*c* and the lobe 2784*d*, and the coupling link 2748*d* is positioned so that a through-hole in the coupling link 2748*d* is aligned with the through-hole 2750*d*. A pin 2752*d* extends through the through-hole 2750*d* to pivotably couple the coupling link 2748*d* to the pivot member 2726 in the channel 2788*d*.

To move the articulation joint 2718 from the unarticulated position to an articulated position (FIGS. 22-24), at least two of the rods 2736*a-d* are displaced along their corresponding axes 2731 *a-d*. Referring to FIG. 16, the rods 2736*a*, 2736*c* are configured to move together with the rod 2736*a* moving in the opposite direction of the rod 2736*c*. For example, if the rod 2736*a* moves distally along the axis 2731*a*, then the rod 2736*c* moves proximally along the axis 2731*c*. Movement of the rods 2736*a*, 2736*c* create a pushing force with one rod and a pulling force with the other that are complementary to articulate the articulation joint in a first direction, for example, the pitch direction. These forces translate along their corresponding series of links to generate complementary pushing and pulling forces on the pivot member 2726, which pivots to articulate the articulation joint 2718 in the first direction.

Referring to FIG. 17, in various instances, the rods 2736*b*, 2736*d* are configured to move together with the rod 2736*b* moving in the opposite direction of the rod 2736*d*. For example, if the rod 2736*b* moves distally along the axis 2731*b*, the rod 2736*d* moves proximally along the axis 2731*d*. Movement of the rods 2736*b*, 2736*d* create a pushing force with one rod and a pulling force with the other that are complementary to articulate the articulation joint in a second direction transverse to the first direction, for example, the yaw direction. For example, these forces translate along their corresponding series of links to generate complementary pushing and pulling forces on the pivot member 2726, which pivots the articulation joint 2718 in the second direction. When all four rods 2736*a-d* are moved, the articulation is a combination of the articulation in the first direction due to actuation of the rods 2736*a,c* and articulation in the second direction due to actuation of the rods 2736*b,d*.

Referring to FIG. 19, each pair of articulation rods and drive racks is coupled to a drive gear 2760*a*, 2760*b* and a carrier 2758*a*, 2758*b*. More specifically, the rod 2736*a* is driven by the drive rack 2732*a*, which includes teeth 2756*a* that mate with teeth 2761*a* of the drive gear 2760*a*. The rod 2736*c* is driven by the drive rack 2732*c*, which includes teeth 2756*c* that also mate with the teeth 2761*a* of drive gear

2760a. The drive gear 2760a is attached to the carrier 2758a and, for example, can be attached to the carrier 2758a by a pin 2762a. The drive gear 2760a is able to rotate freely about the pin 2762a. Movement of the carrier 2758a in the proximal direction causes the drive rack 2732a to move in the distal direction along the axis 2731a (FIG. 16) and the drive rack 2732c to move in the proximal direction along axis 2731c (FIG. 16). Movement of the carrier 2758a in the distal direction causes the drive rack 2732a to move in the proximal direction along the axis 2731a and the drive rack 2732c to move in the distal direction along axis 2731c. In such instances, movement of the carrier 2758a results in complementary push-pull forces being applied to the pivot member 2726 by the mechanical links 2744a and 2744c. In various instances, the carrier 2758a can be coupled to a motor in the tool housing (e.g. the first motor 2604 in control circuit 2600 in FIG. 7), which can selectively control actuation of the carrier 2758a.

Referring primarily now to FIG. 13, the carrier 2758a is configured to translate in the channel 2753 in the proximal direction or the distal direction. The drive rack 2732a rests against the bottom 2710a of the opening 2708a, and the teeth 2756a of the drive rack 2732a extend through a slot 2713a in the bottom 2710a of the opening 2708a to mate with the teeth 2761a of the gear 2760a. The drive rack 2732c rests against the bottom 2710c of the opening 2708c, and the teeth 2756c of the drive rack 2732c extend through a slot 2713c in the bottom 2710c of the opening 2708c to also mate with the teeth 2761a of the gear 2760a. Movement of the carrier 2758a in the channel 2753 causes the drive racks 2732a,c to move along the slots 2713a,c to drive the rods 2736a,c in the channels 2735a,c, respectively.

Referring to FIG. 18, the rod 2736b is driven by the drive rack 2732b, which includes teeth 2756b that mate with teeth 2761b of drive gear 2760b. The rod 2736d is driven by the drive rack 2732d, which includes teeth 2756d that also mate with the teeth 2761b of drive gear 2760b. The drive gear 2760b can be attached to a carrier 2758b by a pin 2762b. The drive gear 2760b is able to rotate freely about the pin 2762b. Movement of the carrier 2758b in the proximal direction causes the drive rack 2732b to move in the distal direction along the axis 2731b (FIG. 17) and the drive rack 2732d to move in the proximal direction along the axis 2731d (FIG. 17). Movement of the carrier 2758b in the distal direction causes the drive rack 2732b to move in the proximal direction along the axis 2731b and the drive rack 2732d to move in the distal direction along the axis 2731d. In such instances, movement of the carrier 2758b results in complementary push-pull forces being applied to the pivot member 2726 by the mechanical links 2744b and 2744d. In various instances, the carrier 2758c can be coupled to a motor in the tool housing (e.g. the second motor 2674 in control circuit 2600 in FIG. 7), which can selectively control actuation of the carrier 2758b.

Figure 12:
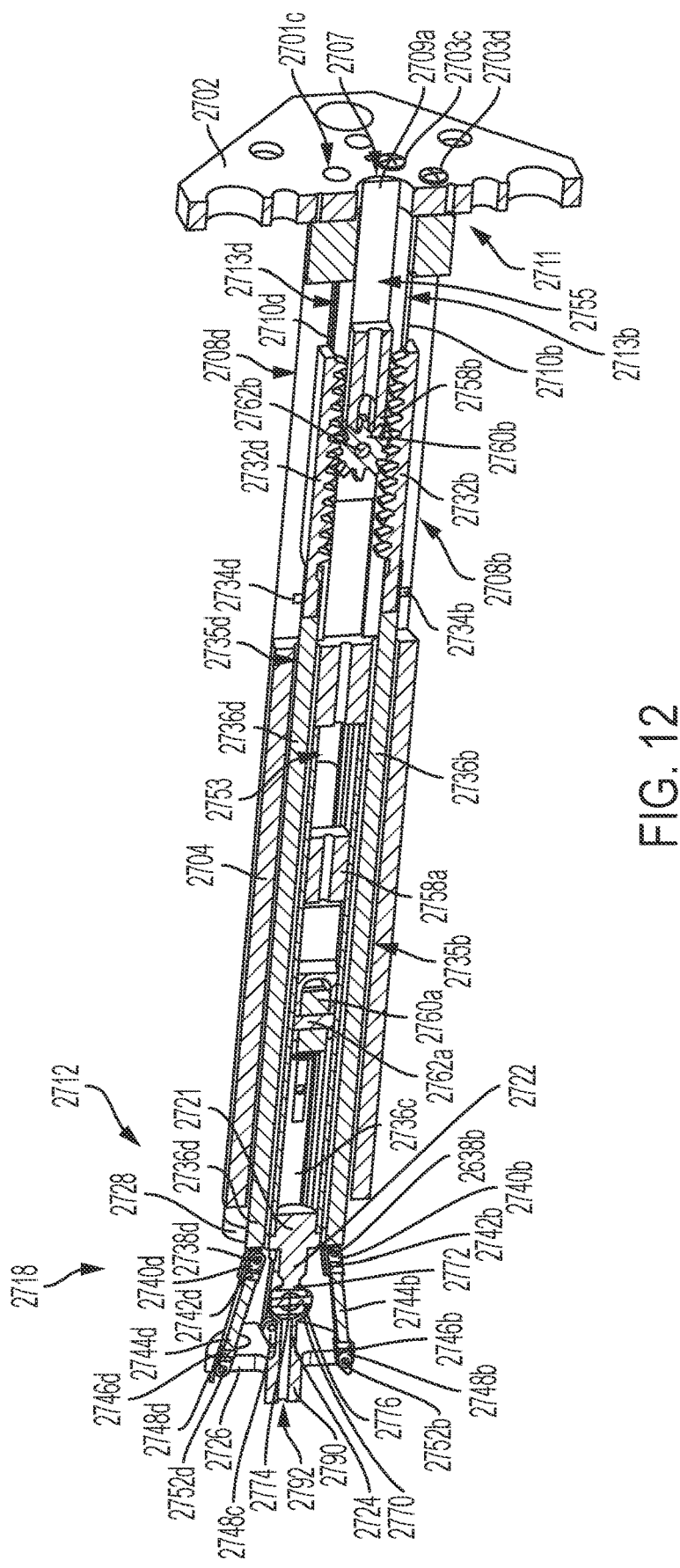
FIG. 12 is a cross-sectional view along the cross-section line indicated in FIG. 10, in accordance with at least one aspect of the present disclosure.

Referring primarily now to FIG. 12, the carrier 2758b can translate in the channel 2755 in the proximal direction or the distal direction. The drive rack 2732b rests against the bottom 2710b of the opening 2708b. The teeth 2756b of the drive rack 2732b extend through a slot 2713b in the bottom 2710b of the opening 2708b to mate with the teeth 2761b of the gear 2760b. The drive rack 2732d rests against the bottom 2710d of the opening 2708d. The teeth 2756d of the drive rack 2732d extend through a slot 2713d in the bottom 2710d of the opening 2708d to also mate with the teeth 2761b of the gear 2760b. Movement of the carrier 2758b in the channel 2753 causes the drive racks 2732b,d to move along the slots 2713b,d and drive the rods 2736b,d to translate in the channels 2735b,d, respectively.

FIGS. 22-24 show the articulation joint 2718 in one of any possible articulated configurations. The articulation joint 2718 can be pivoted by cooperative movement of all four rods 2736a-d. Referring to FIG. 23, the rod 2736c is more distal than the rod 2736a causing the end effector 2706 to articulate towards the rod 2736a. In this example position, the rod 2736c is generating a pushing force at the articulation joint 2718, and the rod 2736a is generating a complementary pulling force at the articulation joint 2718. Referring to FIG. 24, the rod 2736d is more distal than the rod 2736b causing the end effector 2706 to articulate towards the rod 2736b. In this example position, the rod 2736d is generating a pushing force at the articulation joint 2718 and the rod 2736b is generating a complementary pulling force at the articulation joint 2718. The end effector 2706 can be articulated in any direction by the translation of all four rods 2736a-d.

Examples

Various aspects of the subject matter described herein are set out in the following numbered examples.

Example 1—A robotic surgical tool, comprising an end effector, an elongate shaft defining a longitudinal axis, and an articulation joint. The articulation joint comprises a pivot plate attached to the end effector, a fixed plate attached to the elongate shaft, and a spherical joint coupled to the pivot plate and the fixed plate. The robotic surgical tool further comprises an articulation drive system. The articulation drive system comprises a first rod extending through the elongate shaft and movable along a first axis, wherein the first rod comprises a first distal end, a first mechanical link pivotably coupled to the first distal end and pivotably coupled to the pivot plate, and a second rod extending through the elongate shaft and movable along a second axis, wherein the second rod comprises a second distal end. The articulation drive system further comprises a second mechanical link pivotably coupled to the second distal end and pivotably coupled to the pivot plate, a third rod extending through the elongate shaft and movable along a third axis, wherein translation of the first rod and the third rod generates complementary push-pull forces on the pivot plate, and wherein the third rod comprises a third distal end. The articulation drive system further comprises a third mechanical link pivotably coupled to the third distal end and pivotably coupled to the pivot plate, a fourth rod extending through the elongate shaft and movable along a fourth axis, wherein translation of the second rod and the fourth rod generates complementary push-pull forces on the pivot plate, wherein the fourth rod comprises a fourth distal end. The articulation drive system further comprises a fourth mechanical link pivotably coupled to the fourth distal end and pivotably coupled to the pivot plate. The first rod, the second rod, the third rod, and the fourth rod are equidistantly-positioned radially outward from the longitudinal axis and equidistantly-spaced apart within the elongate shaft.

Example 2—The robotic surgical tool of Example 1, wherein the spherical joint comprises a constant velocity joint.

Example 3—The robotic surgical tool of Examples 1 or 2, wherein the pivot plate comprises a first lobe that extends radially between the first axis and the second axis when the articulation joint is in an unarticulated position, a second lobe that extends radially between the second axis and the third axis when the articulation joint is in the unarticulated position, a third lobe that extends radially between the third axis and the fourth axis when the articulation joint is in the unarticulated position, and a fourth lobe that extends radially between the fourth axis and the first axis when the articulation joint is the unarticulated position.

Example 4—The robotic surgical tool of Examples 1, 2, or 3, wherein the pivot plate further comprises a proximally-extending central shaft, and wherein the proximally-extending central shaft supports a distal portion of the spherical joint.

Example 5—The robotic surgical tool of Examples 1, 2, 3, or 4, wherein the fixed plate comprises a distally-extending central shaft, and wherein the distally-extending central shaft supports a proximal portion of the spherical joint.

Example 6—The robotic surgical tool of Examples 1, 2, 3, 4, or 5, wherein the first mechanical link, the second mechanical link, the third mechanical link, and the fourth mechanical link are respectively coupled to the first distal end, the second distal end, the third distal end, and the fourth distal end at a first radial distance from the longitudinal axis, and wherein the first mechanical link, the second mechanical link, the third mechanical link, and the fourth mechanical link are coupled to the pivot plate at a second radial distance from the longitudinal axis, and wherein the second radial distance is greater than the first radial distance.

Example 7—The robotic surgical tool of Examples 1, 2, 3, 4, 5, or 6, wherein the first rod further comprises a first proximal end, wherein the second rod further comprises a second proximal end, wherein the third rod further comprises a third proximal end, and wherein the fourth rod further comprises a fourth proximal end. The articulation drive system further comprises a first drive rack coupled to the first proximal end, a second drive rack coupled to the second proximal end, and a third drive rack coupled to the third proximal end. The articulation drive system further comprises a first gear mechanically coupled to the first and third drive racks, a first carrier coupled to the first gear, wherein translation of the first carrier causes the first and third rods to translate, wherein the first rod translates in the opposite direction of the third rod. The articulation drive system further comprises a fourth drive rack coupled to the fourth proximal end, a second gear mechanically coupled to the second and fourth drive racks, and a second carrier coupled to the second gear. Translation of the second carrier causes the second and fourth rods to translate, wherein the second rod translates in the opposite direction of the fourth rod.

Example 8—The robotic surgical tool of Example 7, wherein the articulation drive system further comprises a first spring mechanically coupled between the first drive rack and the elongated shaft, a second spring mechanically coupled between the second drive rack and the elongated shaft, a third spring mechanically coupled between the third drive rack and the elongated shaft, and a fourth spring mechanically coupled between the fourth drive rack and the elongated shaft.

Example 9—A robotic surgical tool, comprising an end effector comprising a pivot member, an elongate shaft defining a longitudinal axis and comprising a fixed member, and an articulation system. The articulation system comprises a first connection between the end effector and the elongate shaft, wherein the first connection comprises a constant velocity joint coupled between the pivot member and the fixed member. The articulation system further comprises a second connection between the end effector and the elongate shaft, wherein the second connection comprises a first series of linkages. The articulation system further comprises a third connection between the end effector and the elongate shaft, wherein the third connection comprises a second series of linkages. Movement of the first series of linkages and the third series of linkages generate complementary push-pull forces on the end effector. The articulation system further comprises a fourth connection between the end effector and the elongate shaft, wherein the fourth connection comprises a third series of linkages. The articulation system further comprises a fifth connection between the end effector and the elongate shaft, wherein the fifth connection comprises a fourth series of linkages. Movement of the second series of linkages and the fourth series of linkages generate complementary push-pull forces on the end effector.

Example 10—The robotic surgical tool of Example 9, wherein the first series of linkages comprises a first rod extending through the elongate shaft and movable along a first axis, wherein the first rod comprises a first distal end, and a first mechanical link pivotably coupled to the first distal end and pivotably coupled to the end effector. The second series of linkages comprises a second rod extending through the elongate shaft and movable along a second axis, wherein the second rod comprises a second distal end, and a second mechanical link pivotably coupled to the second distal end and pivotably coupled to the end effector. The third series of linkages comprises a third rod extending through the elongate shaft and movable along a third axis. Movement of the first series of linkages and the third series of linkages is generated by translation of the first rod and the third rod, and wherein the third push-pull rod comprises a third distal end. The third series of linkages further comprises a third mechanical link pivotably coupled to the third distal end and pivotably coupled to the end effector. The fourth series of linkages comprises a fourth rod extending through the elongate shaft and movable along a fourth axis. Movement of the first series of linkages and the third series of linkages is generated by translation of the second rod and the fourth rod, and wherein the fourth rod comprises a fourth distal end. The fourth series of linkages further comprises a fourth mechanical link pivotably coupled to the fourth distal end and pivotably coupled to the end effector. The first rod, the second rod, the third rod, and the fourth rod are equidistantly-positioned radially outward from the longitudinal axis and equidistantly-spaced apart within the elongate shaft.

Example 11—The robotic surgical tool of Example 10, wherein the pivot member comprises a first lobe that extends radially between the first axis and the second axis when the articulation system is in an unarticulated position, a second lobe that extends radially between the second axis and the third axis when the articulation system is in the unarticulated position, a third lobe that extends radially between the third axis and the fourth axis when the articulation system is in the unarticulated position, and a fourth lobe that extends radially between the fourth axis and the first axis when the articulation system is in the unarticulated position.

Example 12—The robotic surgical tool of Examples 9, 10, or 11, wherein the pivot member comprises a proximally-extending central shaft, and wherein the proximally-extending central shaft supports a distal portion of the constant velocity joint.

Example 13—The robotic surgical tool of Examples 9, 10, 11, or 12, wherein the fixed member further comprises a distally-extending central shaft, and wherein the distally-extending central shaft supports a proximal portion of the constant velocity joint.

Example 14—The robotic surgical tool of Examples 10, 11, 12, or 13, wherein the first mechanical link, the second mechanical link, the third mechanical link, and the fourth mechanical link are respectively coupled to the first distal end, the second distal end, the third distal end, and the fourth distal end at a first radial distance from the longitudinal axis, and wherein the first mechanical link, the second mechanical link, the third mechanical link, and the fourth mechanical link are coupled to the pivot plate at a second radial distance from the longitudinal axis, and wherein the second radial distance is greater than the first radial distance.

Example 15—The robotic surgical tool of Examples 10, 11, 12, 13, or 14, wherein the first rod further comprises a first proximal end, wherein the second rod further comprises a second proximal end, wherein the third rod further comprises a third proximal end, and wherein the fourth rod further comprises a fourth proximal end. The articulation drive system further comprises a first drive rack coupled to the first proximal end, a second drive rack coupled to the second proximal end, and a third drive rack coupled to the third proximal end. The articulation drive system further comprises a first gear mechanically coupled to the first and third drive racks, and a first carrier coupled to the first gear. Translation of the first carrier causes the first and third rods to translate, wherein the first rod translates in the opposite direction of the third rod. The articulation drive system further comprises a fourth drive rack coupled to the fourth proximal end, a second gear mechanically coupled to the second and fourth drive racks, and a second carrier coupled to the second gear. Translation of the second carrier causes the second and fourth rods to translate, wherein the second rod translates in the opposite direction of the fourth rod.

Example 16—The robotic surgical tool of Example 15, wherein the articulation drive system further comprises a first spring mechanically coupled between the first drive rack and the elongated shaft, a second spring mechanically coupled between the second drive rack and the elongated shaft, a third spring mechanically coupled between the third drive rack and the elongated shaft, and a fourth spring mechanically coupled between the fourth drive rack and the elongated shaft.

Example 17—A robotic surgical tool, comprising an end effector comprising a pivot member, an elongate shaft defining a longitudinal axis and comprising a fixed member, an articulation joint comprising a constant velocity joint coupled to the pivot member and the fixed member, and an articulation drive system. The articulation drive system comprises a first push-pull rod extending through the elongate shaft and movable along a first axis, wherein the first push-pull rod comprises first distal end. The articulation drive system further comprises a first mechanical link pivotably coupled to the first distal end and pivotably coupled to the pivot member, and a second push-pull rod extending through the elongate shaft and movable along a second axis, wherein the second push-pull rod comprises a second distal end. The articulation drive system further comprises a second mechanical link pivotably coupled to the second distal end and pivotably coupled to the pivot member, and a third push-pull rod extending through the elongate shaft and movable along a third axis. Translation of the first push-pull rod and the third push-pull rod generates complementary push-pull forces on the pivot member. The third push-pull rod comprises third distal end. The articulation drive system further comprises a third mechanical link pivotably coupled to the third distal end and pivotably coupled to the pivot member, and a fourth push-pull rod extending through the elongate shaft and movable along a fourth axis. Translation of the second push-pull rod and the fourth push-pull rod generates complementary push-pull forces on the pivot member. The fourth push-pull rod comprises a fourth distal end. The articulation drive system further comprises a fourth mechanical link pivotably coupled to the fourth distal end and pivotably coupled to the pivot member. The first push-pull rod, the second push-pull rod, the third push-pull rod, and the fourth push-pull rod are equidistantly-positioned radially outward from the longitudinal axis and equidistantly-spaced apart within the elongate shaft.

Example 18—The robotic surgical tool of Example 17, wherein the first mechanical link, the second mechanical link, the third mechanical link, and the fourth mechanical link are respectively coupled to the first distal end, the second distal end, the third distal end, and the fourth distal end at a first radial distance from the longitudinal axis, and wherein the first mechanical link, the second mechanical link, the third mechanical link, and the fourth mechanical link are coupled to the pivot plate at a second radial distance from the longitudinal axis, and wherein the second radial distance is greater than the first radial distance.

Example 19—The robotic surgical tool of Examples 17 or 18, wherein the pivot member comprises a first lobe that extends radially between the first axis and the second axis when the articulation joint is in an unarticulated position, a second lobe that extends radially between the second axis and the third axis when the articulation joint is in the unarticulated position, a third lobe that extends radially between the third axis and the fourth axis when the articulation joint is in the unarticulated position, and a fourth lobe that extends radially between the fourth axis and the first axis when the articulation joint is in the unarticulated position.

Example 20—The robotic surgical tool of Examples 17, 18, or 19, wherein the first push-pull rod further comprises a first proximal end, wherein the second push-pull rod further comprises a second proximal end, wherein the third push-pull rod further comprises a third proximal end, and wherein the fourth push-pull rod further comprises a fourth proximal end. The articulation drive system further comprises a first drive rack coupled to the first proximal end, a second drive rack coupled to the second proximal end, and a third drive rack coupled to the third proximal end. The articulation drive system further comprises a first gear mechanically coupled to the first and third drive racks, and a first carrier coupled to the first gear. Translation of the first carrier causes the first and third push-pull rods to translate, wherein the first push-pull rod translates in the opposite direction of the third rod. The articulation drive system further comprises a fourth drive rack coupled to the fourth proximal end, a second gear mechanically coupled to the second and fourth drive racks, and a second carrier coupled to the second gear. Translation of the second carrier causes the second and fourth push-pull rods to translate, wherein the second push-pull rod translates in the opposite direction of the fourth push-pull rod. The articulation drive system further comprises a first spring mechanically coupled between the first drive rack and the elongated shaft, a second spring mechanically coupled between the second drive rack and the elongated shaft, a third spring mechanically coupled between the third drive rack and the elongated shaft, and a fourth spring mechanically coupled between the fourth drive rack and the elongated shaft.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A robotic surgical tool, comprising:
   an end effector;
   an elongate shaft defining a longitudinal axis;
   an articulation joint comprising:
      a pivot plate attached to the end effector;
      a fixed plate attached to the elongate shaft; and
      a spherical joint coupled to the pivot plate and the fixed plate; and
   an articulation drive system, comprising:
      a first rod extending through the elongate shaft and movable along a first axis, wherein the first rod comprises a first distal end;
      a first mechanical link pivotably coupled to the first distal end and pivotably coupled to the pivot plate;
      a second rod extending through the elongate shaft and movable along a second axis, wherein the second rod comprises a second distal end;
      a second mechanical link pivotably coupled to the second distal end and pivotably coupled to the pivot plate;
      a third rod extending through the elongate shaft and movable along a third axis, wherein translation of the first rod and the third rod generates complementary push-pull forces on the pivot plate, and wherein the third rod comprises a third distal end;
      a third mechanical link pivotably coupled to the third distal end and pivotably coupled to the pivot plate;
      a fourth rod extending through the elongate shaft and movable along a fourth axis, wherein translation of the second rod and the fourth rod generates complementary push-pull forces on the pivot plate, wherein the fourth rod comprises a fourth distal end; and
      a fourth mechanical link pivotably coupled to the fourth distal end and pivotably coupled to the pivot plate.

2. The robotic surgical tool of claim 1, wherein the first rod, the second rod, the third rod, and the fourth rod are equidistantly-positioned radially outward from the longitudinal axis and equidistantly-spaced apart within the elongate shaft, and wherein the spherical joint comprises a constant velocity joint.

3. The robotic surgical tool of claim 1, wherein the pivot plate comprises:
   a first lobe that extends radially between the first axis and the second axis when the articulation joint is in an unarticulated position;
   a second lobe that extends radially between the second axis and the third axis when the articulation joint is in the unarticulated position;
   a third lobe that extends radially between the third axis and the fourth axis when the articulation joint is in the unarticulated position; and
   a fourth lobe that extends radially between the fourth axis and the first axis when the articulation joint is the unarticulated position.

4. The robotic surgical tool of claim 3, wherein the pivot plate further comprises a proximally-extending central shaft, and wherein the proximally-extending central shaft supports a distal portion of the spherical joint.

5. The robotic surgical tool of claim 4, wherein the fixed plate comprises a distally-extending central shaft, and wherein the distally-extending central shaft supports a proximal portion of the spherical joint.

6. The robotic surgical tool of claim 1, wherein the first mechanical link, the second mechanical link, the third mechanical link, and the fourth mechanical link are respectively coupled to the first distal end, the second distal end, the third distal end, and the fourth distal end at a first radial distance from the longitudinal axis, and wherein the first mechanical link, the second mechanical link, the third mechanical link, and the fourth mechanical link are coupled to the pivot plate at a second radial distance from the longitudinal axis, and wherein the second radial distance is greater than the first radial distance.

7. The robotic surgical tool of claim 1, wherein the first rod further comprises a first proximal end, wherein the second rod further comprises a second proximal end, wherein the third rod further comprises a third proximal end, wherein the fourth rod further comprises a fourth proximal end, and wherein the articulation drive system further comprises:
   a first drive rack coupled to the first proximal end;
   a second drive rack coupled to the second proximal end;
   a third drive rack coupled to the third proximal end;
   a first gear mechanically coupled to the first and third drive racks;
   a first carrier coupled to the first gear, wherein translation of the first carrier causes the first and third rods to translate, wherein the first rod translates in the opposite direction of the third rod;
   a fourth drive rack coupled to the fourth proximal end;
   a second gear mechanically coupled to the second and fourth drive racks; and
   a second carrier coupled to the second gear, wherein translation of the second carrier causes the second and fourth rods to translate, wherein the second rod translates in the opposite direction of the fourth rod.

8. The robotic surgical tool of claim 7, wherein the articulation drive system further comprises:
   a first spring mechanically coupled between the first drive rack and the elongated shaft;
   a second spring mechanically coupled between the second drive rack and the elongated shaft;
   a third spring mechanically coupled between the third drive rack and the elongated shaft; and
   a fourth spring mechanically coupled between the fourth drive rack and the elongated shaft.

9. A robotic surgical tool, comprising:
   an end effector comprising a pivot member;
   an elongate shaft defining a longitudinal axis and comprising a fixed member; and
   an articulation system, comprising:

a first connection between the end effector and the elongate shaft, wherein the first connection comprises a constant velocity joint coupled between the pivot member and the fixed member;

a second connection between the end effector and the elongate shaft, wherein the second connection comprises a first series of linkages;

a third connection between the end effector and the elongate shaft, wherein the third connection comprises a second series of linkages, and wherein movement of the first series of linkages and the second series of linkages generates complementary push-pull forces on the end effector;

a fourth connection between the end effector and the elongate shaft, wherein the fourth connection comprises a third series of linkages; and a fifth connection between the end effector and the elongate shaft, wherein the fifth connection comprises a fourth series of linkages, and wherein movement of the third series of linkages and the fourth series of linkages generates complementary push-pull forces on the end effector.

10. The robotic surgical tool of claim 9, wherein the first series of linkages comprises:
a first rod extending through the elongate shaft and movable along a first axis, wherein the first rod comprises a first distal end; and
a first mechanical link pivotably coupled to the first distal end and pivotably coupled to the end effector;
wherein the second series of linkages comprises:
a second rod extending through the elongate shaft and movable along a second axis, wherein the second rod comprises a second distal end; and
a second mechanical link pivotably coupled to the second distal end and pivotably coupled to the end effector;
wherein the third series of linkages comprises:
a third rod extending through the elongate shaft and movable along a third axis, wherein movement of the first series of linkages and the third series of linkages is generated by translation of the first rod and the third rod, and wherein the third rod comprises a third distal end; and
a third mechanical link pivotably coupled to the third distal end and pivotably coupled to the end effector; and
wherein the fourth series of linkages comprises:
a fourth rod extending through the elongate shaft and movable along a fourth axis, wherein movement of the second series of linkages and the fourth series of linkages is generated by translation of the second rod and the fourth rod, and wherein the fourth rod comprises a fourth distal end; and
a fourth mechanical link pivotably coupled to the fourth distal end and pivotably coupled to the end effector;
wherein the first rod, the second rod, the third rod, and the fourth rod are equidistantly-positioned radially outward from the longitudinal axis and equidistantly-spaced apart within the elongate shaft.

11. The robotic surgical tool of claim 10, wherein the pivot member comprises:
a first lobe that extends radially between the first axis and the second axis when the articulation system is in an unarticulated position;
a second lobe that extends radially between the second axis and the third axis when the articulation system is in the unarticulated position;
a third lobe that extends radially between the third axis and the fourth axis when the articulation system is in the unarticulated position; and
a fourth lobe that extends radially between the fourth axis and the first axis when the articulation system is in the unarticulated position.

12. The robotic surgical tool of claim 11, wherein the pivot member comprises a proximally-extending central shaft, and wherein the proximally-extending central shaft supports a distal portion of the constant velocity joint.

13. The robotic surgical tool of claim 12, wherein the fixed member further comprises a distally-extending central shaft, and wherein the distally-extending central shaft supports a proximal portion of the constant velocity joint.

14. The robotic surgical tool of claim 10, wherein the first mechanical link, the second mechanical link, the third mechanical link, and the fourth mechanical link are respectively coupled to the first distal end, the second distal end, the third distal end, and the fourth distal end at a first radial distance from the longitudinal axis, and wherein the first mechanical link, the second mechanical link, the third mechanical link, and the fourth mechanical link are coupled to the pivot member at a second radial distance from the longitudinal axis, and wherein the second radial distance is greater than the first radial distance.

15. The robotic surgical tool of claim 10, wherein the first rod further comprises a first proximal end, wherein the second rod further comprises a second proximal end, wherein the third rod further comprises a third proximal end, wherein the fourth rod further comprises a fourth proximal end, and wherein the articulation system further comprises:
a first drive rack coupled to the first proximal end;
a second drive rack coupled to the second proximal end;
a third drive rack coupled to the third proximal end;
a first gear mechanically coupled to the first and second drive racks;
a first carrier coupled to the first gear, wherein translation of the first carrier causes the first and second rods to translate, wherein the first rod translates in the opposite direction of the second rod;
a fourth drive rack coupled to the fourth proximal end;
a second gear mechanically coupled to the third and fourth drive racks; and
a second carrier coupled to the second gear, wherein translation of the second carrier causes the third and fourth rods to translate, wherein the third rod translates in the opposite direction of the fourth rod.

16. The robotic surgical tool of claim 15, wherein the articulation system further comprises:
a first spring mechanically coupled between the first drive rack and the elongated shaft;
a second spring mechanically coupled between the second drive rack and the elongated shaft;
a third spring mechanically coupled between the third drive rack and the elongated shaft; and
a fourth spring mechanically coupled between the fourth drive rack and the elongated shaft.

17. A robotic surgical tool, comprising:
an end effector comprising a pivot member;
an elongate shaft defining a longitudinal axis and comprising a fixed member;
an articulation joint comprising a constant velocity joint coupled to the pivot member and the fixed member; and
an articulation drive system, comprising:
a first push-pull rod extending through the elongate shaft and movable along a first axis, wherein the first push-pull rod comprises a first distal end;

a first mechanical link pivotably coupled to the first distal end and pivotably coupled to the pivot member;
a second push-pull rod extending through the elongate shaft and movable along a second axis, wherein the second push-pull rod comprises a second distal end;
a second mechanical link pivotably coupled to the second distal end and pivotably coupled to the pivot member;
a third push-pull rod extending through the elongate shaft and movable along a third axis, wherein translation of the first push-pull rod and the third push-pull rod generates complementary push-pull forces on the pivot member, and wherein the third push-pull rod comprises a third distal end;
a third mechanical link pivotably coupled to the third distal end and pivotably coupled to the pivot member;
a fourth push-pull rod extending through the elongate shaft and movable along a fourth axis, wherein translation of the second push-pull rod and the fourth push-pull rod generates complementary push-pull forces on the pivot member, wherein the fourth push-pull rod comprises a fourth distal end; and
a fourth mechanical link pivotably coupled to the fourth distal end and pivotably coupled to the pivot member.

18. The robotic surgical tool of claim 17, wherein the first push-pull rod, the second push-pull rod, the third push-pull rod, and the fourth push-pull rod are equidistantly-positioned radially outward from the longitudinal axis and equidistantly-spaced apart within the elongate shaft, wherein the first mechanical link, the second mechanical link, the third mechanical link, and the fourth mechanical link are respectively coupled to the first distal end, the second distal end, the third distal end, and the fourth distal end at a first radial distance from the longitudinal axis, and wherein the first mechanical link, the second mechanical link, the third mechanical link, and the fourth mechanical link are coupled to the pivot member at a second radial distance from the longitudinal axis, and wherein the second radial distance is greater than the first radial distance.

19. The robotic surgical tool of claim 17, wherein the pivot member comprises:

a first lobe that extends radially between the first axis and the second axis when the articulation joint is in an unarticulated position;
a second lobe that extends radially between the second axis and the third axis when the articulation joint is in the unarticulated position;
a third lobe that extends radially between the third axis and the fourth axis when the articulation joint is in the unarticulated position; and
a fourth lobe that extends radially between the fourth axis and the first axis when the articulation joint is in the unarticulated position.

20. The robotic surgical tool of claim 17, wherein the first push-pull rod further comprises a first proximal end, wherein the second push-pull rod further comprises a second proximal end, wherein the third push-pull rod further comprises a third proximal end, wherein the fourth push-pull rod further comprises a fourth proximal end, and wherein the articulation drive system further comprises:

a first drive rack coupled to the first proximal end;
a second drive rack coupled to the second proximal end;
a third drive rack coupled to the third proximal end;
a first gear mechanically coupled to the first and third drive racks;
a first carrier coupled to the first gear, wherein translation of the first carrier causes the first and third push-pull rods to translate, wherein the first push-pull rod translates in the opposite direction of the third push-pull rod;
a fourth drive rack coupled to the fourth proximal end;
a second gear mechanically coupled to the second and fourth drive racks;
a second carrier coupled to the second gear, wherein translation of the second carrier causes the second and fourth push-pull rods to translate, wherein the second push-pull rod translates in the opposite direction of the fourth push-pull rod;
a first spring mechanically coupled between the first drive rack and the elongated shaft;
a second spring mechanically coupled between the second drive rack and the elongated shaft;
a third spring mechanically coupled between the third drive rack and the elongated shaft; and
a fourth spring mechanically coupled between the fourth drive rack and the elongated shaft.

* * * * *